(12) United States Patent
Beer et al.

(10) Patent No.: US 8,936,919 B2
(45) Date of Patent: Jan. 20, 2015

(54) METHOD FOR THE DETECTION AND DIAGNOSIS OF CANCER INVOLVING PRIMERS AND PROBES FOR THE SPECIFIC DETECTION OF THE MAGE-A3-MARKER

(75) Inventors: Gabriele Annemarie Beer, Penzberg (DE); Thierry Coche, Rixensart (BE); Olivier Gruselle, Rixensart (BE); Dennis Salonga, Research Triangle Park, NC (US); Craig Lawrence Stephens, Research Triangle Park, NC (US)

(73) Assignee: GlaxoSmithKline Biologicals S.A., Rixensart (BE)

( * ) Notice: Subject to any disclaimer, the term of this patent is extended or adjusted under 35 U.S.C. 154(b) by 1783 days.

(21) Appl. No.: 12/305,742

(22) PCT Filed: Jun. 21, 2007

(86) PCT No.: PCT/EP2007/056219
§ 371 (c)(1),
(2), (4) Date: Oct. 31, 2011

(87) PCT Pub. No.: WO2007/147876
PCT Pub. Date: Dec. 27, 2007

(65) Prior Publication Data
US 2012/0040341 A1 Feb. 16, 2012

(30) Foreign Application Priority Data

Jun. 21, 2006 (GB) .................................. 0612342.6

(51) Int. Cl.
*C12P 19/34* (2006.01)
*C12Q 1/68* (2006.01)
*C07K 14/47* (2006.01)

(52) U.S. Cl.
CPC .......... *C12Q 1/6886* (2013.01); *C12Q 2600/16* (2013.01); *C12Q 2600/106* (2013.01); *C07K 14/4748* (2013.01)
USPC ........................................................ 435/91.2

(58) Field of Classification Search
CPC . C12Q 1/2561; C12Q 1/16886; C12Q 1/6844
USPC ........................................................ 435/91.2
See application file for complete search history.

(56) References Cited

U.S. PATENT DOCUMENTS

| 5,612,201 A | 3/1997 | De Plaen et al. |
| 5,985,571 A | 11/1999 | Van Baren et al. |
| 6,811,986 B2 | 11/2004 | Bandaru et al. |
| 7,691,997 B2 | 4/2010 | Khvorova et al. |
| 2007/0231822 A1 * | 10/2007 | Mitas ............................... 435/6 |

FOREIGN PATENT DOCUMENTS

| EP | 1126027 | * | 8/2001 |
| EP | 1659178 A | | 5/2006 |
| WO | WO 9493205 | * | 2/1994 |
| WO | 00/20445 A | | 4/2000 |
| WO | WO 0020445 | * | 4/2000 |
| WO | 03/045427 A | | 6/2003 |
| WO | 2005/105139 A | | 11/2005 |

OTHER PUBLICATIONS

Chung et al., Factors in Tissue Handling and Processing That Impact RNA Obtaineed from Formalin-fixed, Paraffin-embedded Tissue, Journal of Histochemistry & Cytochemistry, 56(11): 1033-1042 (2008).
Penland, RNA expression analysis of formalin-fixed paraffin-embedded tumors, Laboratory Investigation, 87, 383-391 (2007).
Park J-W et al; "A New Strategy for the Diagnosis of MAGE-Expressing Cancers"; Journal of Immunological Methods; Aug. 1, 2002; vol. 266, No. 1-2; 79-86; Elsevier; Amsterdam, NL.
Dalerba Piero et al; "MAGE, BAGE and GAGE gene expression in human rhabdomyosarcomas"; International Journal of Cancer; Jul. 1, 2001; vol. 93, No. 1; 85-90.
Zammatteo N. et al; "DNA Microarray to Monitor the Expression of MAGE-A Genes"; Clinical Chemistry 48:1; Jan. 1, 2002; vol. 48, No. 1; 25-34.
Database Registry [Online] Accession No. RN 722217-76-7; STN; Aug. 4, 2004; Abstract.

* cited by examiner

*Primary Examiner* — Cynthia B Wilder
(74) *Attorney, Agent, or Firm* — Virginia G. Campen

(57) ABSTRACT

The present invention relates to MAGE-3 specific primers and probes for use new diagnostic kits and methods. The invention further relates to immunotherapeutic treatment of specific populations of cancer patients, suffering from MAGE-3 expressing tumors.

5 Claims, 53 Drawing Sheets

FIG. 9A

Nucleotide sequence encoding fusion protein of Protein D fragment, Mage3 fragment, and histidine tail, and its respective amino acid sequence (SEQ ID NO: 35 and 36).

```
atg gat cca aaa act tta gcc ctt tct tta tta gca gct ggc gta cta      48
Met Asp Pro Lys Thr Leu Ala Leu Ser Leu Leu Ala Ala Gly Val Leu
1               5                   10                  15 gca ggt tgt agc agc cat tca tca aat atg gcg aat acc caa atg aaa      96
Ala Gly Cys Ser Ser His Ser Ser Asn Met Ala Asn Thr Gln Met Lys
                20                  25                  30 tca gac aaa atc att att gct cac cgt ggt gct agc ggt tat tta cca     144
Ser Asp Lys Ile Ile Ile Ala His Arg Gly Ala Ser Gly Tyr Leu Pro
                35                  40                  45 gag cat acg tta gaa tct aaa gca ctt gcg ttt gca caa cag gct gat     192
Glu His Thr Leu Glu Ser Lys Ala Leu Ala Phe Ala Gln Gln Ala Asp
        50                  55                  60 tat tta gag caa gat tta gca atg act aag gat ggt cgt tta gtg gtt     240
Tyr Leu Glu Gln Asp Leu Ala Met Thr Lys Asp Gly Arg Leu Val Val
65                  70                  75                  80 att cac gat cac ttt tta gat ggc ttg act gat gtt gcg aaa aaa ttc     288
Ile His Asp His Phe Leu Asp Gly Leu Thr Asp Val Ala Lys Lys Phe
                85                  90                  95 cca cat cgt cat cgt aaa gat ggc cgt tac tat gtc atc gac ttt acc     336
Pro His Arg His Arg Lys Asp Gly Arg Tyr Tyr Val Ile Asp Phe Thr
                100                 105                 110 tta aaa gaa att caa agt tta gaa atg aca gaa aac ttt gaa acc atg     384
Leu Lys Glu Ile Gln Ser Leu Glu Met Thr Glu Asn Phe Glu Thr Met
            115                 120                 125 gat ctg gaa cag cgt agt cag cac tgc aag cct gaa gaa ggc ctt gag     432
Asp Leu Glu Gln Arg Ser Gln His Cys Lys Pro Glu Glu Gly Leu Glu
        130                 135                 140 gcc cga gga gag gcc ctg ggc ctg gtg ggt gcg cag gct cct gct act     480
Ala Arg Gly Glu Ala Leu Gly Leu Val Gly Ala Gln Ala Pro Ala Thr
```

FIG. 9B

```
145                 150                 155                 160 gag gag cag gag gct gcc tcc tcc tct tct act cta gtt gaa gtc acc        528
Glu Glu Gln Glu Ala Ala Ser Ser Ser Ser Thr Leu Val Glu Val Thr
                165                 170                 175 ctg ggg gag gtg cct gct gcc gag tca cca gat cct ccc cag agt cct        576
Leu Gly Glu Val Pro Ala Ala Glu Ser Pro Asp Pro Pro Gln Ser Pro
                180                 185                 190 cag gga gcc tcc agc ctc ccc act acc atg aac tac cct ctc tgg agc        624
Gln Gly Ala Ser Ser Leu Pro Thr Thr Met Asn Tyr Pro Leu Trp Ser
                195                 200                 205 caa tcc tat gag gac tcc agc aac caa gaa gag gag ggg cca agc acc        672
Gln Ser Tyr Glu Asp Ser Ser Asn Gln Glu Glu Glu Gly Pro Ser Thr
                210                 215                 220 ttc cct gac ctg gag tcc gag ttc caa gca gca ctc agt agg aag gtg        720
Phe Pro Asp Leu Glu Ser Glu Phe Gln Ala Ala Leu Ser Arg Lys Val
225                 230                 235                 240 gcc gaa ttg gtt cat ttt ctg ctc ctc aag tat cga gcc agg gag ccg        768
Ala Glu Leu Val His Phe Leu Leu Leu Lys Tyr Arg Ala Arg Glu Pro
                245                 250                 255 gtc aca aag gca gaa atg ctg ggg agt gtc gtc gga aat tgg cag tat        816
Val Thr Lys Ala Glu Met Leu Gly Ser Val Val Gly Asn Trp Gln Tyr
                260                 265                 270 ttc ttt cct gtg atc ttc agc aaa gct tcc agt tcc ttg cag ctg gtc        864
Phe Phe Pro Val Ile Phe Ser Lys Ala Ser Ser Ser Leu Gln Leu Val
                275                 280                 285 ttt ggc atc gag ctg atg gaa gtg gac ccc atc ggc cac ttg tac atc        912
Phe Gly Ile Glu Leu Met Glu Val Asp Pro Ile Gly His Leu Tyr Ile
                290                 295                 300 ttt gcc acc tgc ctg ggc ctc tcc tac gat ggc ctg ctg ggt gac aat        960
Phe Ala Thr Cys Leu Gly Leu Ser Tyr Asp Gly Leu Leu Gly Asp Asn
305                 310                 315                 320 cag atc atg ccc aag gca ggc ctc ctg ata atc gtc ctg gcc ata atc       1008
Gln Ile Met Pro Lys Ala Gly Leu Leu Ile Ile Val Leu Ala Ile Ile
                325                 330                 335
```

FIG. 9C

```
gca aga gag ggc gac tgt gcc cct gag gag aaa atc tgg gag gag ctg      1056
Ala Arg Glu Gly Asp Cys Ala Pro Glu Glu Lys Ile Trp Glu Glu Leu
        340                 345                 350 agt gtg tta gag gtg ttt gag ggg agg gaa gac agt atc ttg ggg gat      1104
Ser Val Leu Glu Val Phe Glu Gly Arg Glu Asp Ser Ile Leu Gly Asp
        355                 360                 365 ccc aag aag ctg ctc acc caa cat ttc gtg cag gaa aac tac ctg gag      1152
Pro Lys Lys Leu Leu Thr Gln His Phe Val Gln Glu Asn Tyr Leu Glu
        370                 375                 380 tac cgg cag gtc ccc ggc agt gat cct gca tgt tat gaa ttc ctg tgg      1200
Tyr Arg Gln Val Pro Gly Ser Asp Pro Ala Cys Tyr Glu Phe Leu Trp
385                 390                 395                 400 ggt cca agg gcc ctc gtt gaa acc agc tat gtg aaa gtc ctg cac cat      1248
Gly Pro Arg Ala Leu Val Glu Thr Ser Tyr Val Lys Val Leu His His
                405                 410                 415 atg gta aag atc agt gga gga cct cac att tcc tac cca ccc ctg cat      1296
Met Val Lys Ile Ser Gly Gly Pro His Ile Ser Tyr Pro Pro Leu His
            420                 425                 430 gag tgg gtt ttg aga gag ggg gaa gag ggc ggt cat cac cat cac cat      1344
Glu Trp Val Leu Arg Glu Gly Glu Glu Gly Gly His His His His His
        435                 440                 445 cac cat taa                                                          1353
His His
    450
```

FIG. 10A

Fusion protein of NS1-MAGE3, and Histidine tail (SEQ ID NO:37)

```
Met Asp Pro Asn Thr Val Ser Ser Phe Gln Val Asp Cys Phe Leu Trp
1               5                   10                  15
His Val Arg Lys Arg Val Ala Asp Gln Glu Leu Gly Asp Ala Pro Phe
            20                  25                  30
Leu Asp Arg Leu Arg Arg Asp Gln Lys Ser Leu Arg Gly Arg Gly Ser
        35                  40                  45
Thr Leu Gly Leu Asp Ile Glu Thr Ala Thr Arg Ala Gly Lys Gln Ile
    50                  55                  60
Val Glu Arg Ile Leu Lys Glu Glu Ser Asp Glu Ala Leu Lys Met Thr
65                  70                  75                  80
Met Asp Leu Glu Gln Arg Ser Gln His Cys Lys Pro Glu Glu Gly Leu
            85                  90                  95
Glu Ala Arg Gly Glu Ala Leu Gly Leu Val Gly Ala Gln Ala Pro Ala
            100                 105                 110
Thr Glu Glu Gln Glu Ala Ala Ser Ser Ser Ser Thr Leu Val Glu Val
        115                 120                 125
Thr Leu Gly Glu Val Pro Ala Ala Glu Ser Pro Asp Pro Pro Gln Ser
    130                 135                 140
Pro Gln Gly Ala Ser Ser Leu Pro Thr Thr Met Asn Tyr Pro Leu Trp
145                 150                 155                 160
Ser Gln Ser Tyr Glu Asp Ser Ser Asn Gln Glu Glu Glu Gly Pro Ser
            165                 170                 175
Thr Phe Pro Asp Leu Glu Ser Glu Phe Gln Ala Ala Leu Ser Arg Lys
            180                 185                 190
Val Ala Glu Leu Val His Phe Leu Leu Leu Lys Tyr Arg Ala Arg Glu
        195                 200                 205
Pro Val Thr Lys Ala Glu Met Leu Gly Ser Val Val Gly Asn Trp Gln
    210                 215                 220
Tyr Phe Phe Pro Val Ile Phe Ser Lys Ala Ser Ser Ser Leu Gln Leu
225                 230                 235                 240
Val Phe Gly Ile Glu Leu Met Glu Val Asp Pro Ile Gly His Leu Tyr
            245                 250                 255
Ile Phe Ala Thr Cys Leu Gly Leu Ser Tyr Asp Gly Leu Leu Gly Asp
            260                 265                 270
Asn Gln Ile Met Pro Lys Ala Gly Leu Leu Ile Ile Val Leu Ala Ile
        275                 280                 285
Ile Ala Arg Glu Gly Asp Cys Ala Pro Glu Glu Lys Ile Trp Glu Glu
                    290                 295                 300
```

FIG. 10B

```
Leu Ser Val Leu Glu Val Phe Glu Gly Arg Glu Asp Ser Ile Leu Gly
305                 310                 315                 320
Asp Pro Lys Lys Leu Leu Thr Gln His Phe Val Gln Glu Asn Tyr Leu
            325                 330                 335
Glu Tyr Arg Gln Val Pro Gly Ser Asp Pro Ala Cys Tyr Glu Phe Leu
            340                 345                 350
Trp Gly Pro Arg Ala Leu Val Glu Thr Ser Tyr Val Lys Val Leu His
            355                 360                 365
His Met Val Lys Ile Ser Gly Gly Pro His Ile Ser Tyr Pro Pro Leu
        370                 375                 380
His Glu Trp Val Leu Arg Glu Gly Glu Glu Gly Gly His His His His
385                 390                 395                 400
His His His
```

FIG. 11

DNA coding fusion protein NS1-MAGE3-His (SEQ ID NO:38)

```
atggatccaa acactgtgtc aagctttcag gtagattgct ttctttggca tgtccgcaaa    60
cgagttgcag accaagaact aggtgatgcc ccattccttg atcggcttcg ccgagatcag   120
aaatccctaa gaggaagggg cagcactctt ggtctggaca tcgagacagc cacacgtgct   180
ggaaagcaga tagtggagcg gattctgaaa gaagaatccg atgaggcact taaaatgacc   240
atggatctgg aacagcgtag tcagcactgc aagcctgaag aaggccttga ggcccgagga   300
gaggccctgg gcctggtggg tgcgcaggct cctgctactg aggagcagga ggctgcctcc   360
tcctcttcta ctctagttga agtcaccctg ggggaggtgc ctgctgccga gtcaccagat   420
cctccccaga gtcctcaggg agcctccagc ctccccacta ccatgaacta ccctctctgg   480
agccaatcct atgaggactc cagcaaccaa gaagaggagg ggccaagcac cttccctgac   540
ctggagtccg agttccaagc agcactcagt aggaaggtgg ccgaattggt tcattttctg   600
ctcctcaagt atcgagccag ggagccggtc acaaaggcag aaatgctggg gagtgtcgtc   660
ggaaattggc agtatttctt tcctgtgatc ttcagcaaag cttccagttc cttgcagctg   720
gtctttggca tcgagctgat ggaagtggac cccatcggcc acttgtacat ctttgccacc   780
tgcctgggcc tctcctacga tggcctgctg ggtgacaatc agatcatgcc caaggcaggc   840
ctcctgataa tcgtcctggc cataatcgca agagagggcg actgtgcccc tgaggagaaa   900
atctgggagg agctgagtgt gttagaggtg tttgagggga gggaagacag tatcttgggg   960
gatcccaaga agctgctcac ccaacatttc gtgcaggaaa actacctgga gtaccggcag  1020
gtccccggca gtgatcctgc atgttatgaa ttcctgtggg gtccaagggc cctcgttgaa  1080
accagctatg tgaaagtcct gcaccatatg gtaaagatca gtggaggacc tcacatttcc  1140
tacccacccc tgcatgagtg ggtttgaga gaggggggaag agggcggtca tcaccatcac  1200
catcaccatt aa                                                      1212
```

FIG. 12A

Fusion protein of CLYTA-MAGE3-Histidine (SEQ ID NO:39)

```
Met Lys Gly Gly Ile Val His Ser Asp Gly Ser Tyr Pro Lys Asp Lys
1               5                   10                  15
Phe Glu Lys Ile Asn Gly Thr Trp Tyr Tyr Phe Asp Ser Ser Gly Tyr
                20                  25                  30
Met Leu Ala Asp Arg Trp Arg Lys His Thr Asp Gly Asn Trp Tyr Trp
            35                  40                  45
Phe Asp Asn Ser Gly Glu Met Ala Thr Gly Trp Lys Lys Ile Ala Asp
        50                  55                  60
Lys Trp Tyr Tyr Phe Asn Glu Glu Gly Ala Met Lys Thr Gly Trp Val
65                  70                  75                  80
Lys Tyr Lys Asp Thr Trp Tyr Tyr Leu Asp Ala Lys Glu Gly Ala Met
                85                  90                  95
Val Ser Asn Ala Phe Ile Gln Ser Ala Asp Gly Thr Gly Trp Tyr Tyr
                100                 105                 110
Leu Lys Pro Asp Gly Thr Leu Ala Asp Arg Pro Glu Leu Ala Ser Met
            115                 120                 125
Leu Asp Met Asp Leu Glu Gln Arg Ser Gln His Cys Lys Pro Glu Glu
        130                 135                 140
Gly Leu Glu Ala Arg Gly Glu Ala Leu Gly Leu Val Gly Ala Gln Ala
145                 150                 155                 160
Pro Ala Thr Glu Glu Gln Glu Ala Ala Ser Ser Ser Thr Leu Val
                165                 170                 175
Glu Val Thr Leu Gly Glu Val Pro Ala Ala Glu Ser Pro Asp Pro Pro
            180                 185                 190
Gln Ser Pro Gln Gly Ala Ser Ser Leu Pro Thr Thr Met Asn Tyr Pro
        195                 200                 205
Leu Trp Ser Gln Ser Tyr Glu Asp Ser Ser Asn Gln Glu Glu Glu Gly
        210                 215                 220
Pro Ser Thr Phe Pro Asp Leu Glu Ser Glu Phe Gln Ala Ala Leu Ser
225                 230                 235                 240
Arg Lys Val Ala Glu Leu Val His Phe Leu Leu Leu Lys Tyr Arg Ala
                245                 250                 255
Arg Glu Pro Val Thr Lys Ala Glu Met Leu Gly Ser Val Val Gly Asn
            260                 265                 270
Trp Gln Tyr Phe Phe Pro Val Ile Phe Ser Lys Ala Ser Ser Ser Leu
        275                 280                 285
Gln Leu Val Phe Gly Ile Glu Leu Met Glu Val Asp Pro Ile Gly His
        290                 295                 300
Leu Tyr Ile Phe Ala Thr Cys Leu Gly Leu Ser Tyr Asp Gly Leu Leu
305                 310                 315                 320
Gly Asp Asn Gln Ile Met Pro Lys Ala Gly Leu Leu Ile Ile Val Leu
```

FIG. 12B

```
                    325                 330                 335
Ala Ile Ile Ala Arg Glu Gly Asp Cys Ala Pro Glu Glu Lys Ile Trp
                340                 345                 350
Glu Glu Leu Ser Val Leu Glu Val Phe Glu Gly Arg Glu Asp Ser Ile
                355                 360                 365
Leu Gly Asp Pro Lys Lys Leu Leu Thr Gln His Phe Val Gln Glu Asn
            370                 375                 380
Tyr Leu Glu Tyr Arg Gln Val Pro Gly Ser Asp Pro Ala Cys Tyr Glu
385                 390                 395                 400
Phe Leu Trp Gly Pro Arg Ala Leu Val Glu Thr Ser Tyr Val Lys Val
                405                 410                 415
Leu His His Met Val Lys Ile Ser Gly Gly Pro His Ile Ser Tyr Pro
                420                 425                 430
Pro Leu His Glu Trp Val Leu Arg Glu Gly Glu Gly Gly His His
            435                 440                 445
His His His His His
        450
```

FIG. 13

DNA for fusion protein CLYTA-MAGE3-His (SEQ ID NO:40)

```
atgaaaggggg gaattgtaca ttcagacggc tcttatccaa aagacaagtt tgagaaaatc     60
aatggcactt ggtactactt tgacagttca ggctatatgc ttgcagaccg ctggaggaag    120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca aaccagacgg aacactggca    360
gacaggccag aattggccag catgctggac atggatctgg aacagcgtag tcagcactgc    420
aagcctgaag aaggccttga ggcccgagga gaggccctgg gcctggtggg tgcgcaggct    480
cctgctactg aggagcagga ggctgcctcc tcctcttcta ctctagttga agtcaccctg    540
ggggaggtgc ctgctgccga gtcaccagat cctccccaga gtcctcaggg agcctccagc    600
ctccccacta ccatgaacta ccctctctgg agccaatcct atgaggactc cagcaaccaa    660
gaagaggagg ggccaagcac cttccctgac ctggagtctg agttccaagc agcactcagt    720
aggaaggtgg ccaagttggt tcatttctg ctcctcaagt atcgagccag ggagccggtc    780
acaaaggcag aaatgctggg gagtgtcgtc ggaaattggc agtacttctt cctgtgatc    840
ttcagcaaag cttccgattc cttgcagctg gtctttggca tcgagctgat ggaagtggac    900
cccatcggcc acgtgtacat ctttgccacc tgcctgggcc tctcctacga tggcctgctg    960
ggtgacaatc agatcatgcc caagacaggc ttcctgataa tcatcctggc cataatcgca   1020
aaagagggcg actgtgcccc tgaggagaaa atctgggagg agctgagtgt gttagaggtg   1080
tttgagggga gggaagacag tatcttcggg gatcccaaga gctgctcac ccaatatttc    1140
gtgcaggaaa actacctgga gtaccggcag gtccccggca gtgatcctgc atgctatgag   1200
ttcctgtggg gtccaagggc cctcattgaa accagctatg tgaaagtcct gcaccatatg   1260
gtaaagatca gtggaggacc tcgcatttcc tacccactcc tgcatgagtg ggctttgaga   1320
gaggggaag agggcggtca tcaccatcac catcaccatt aa                        1362
```

FIG. 14

Alignment of MAGE-A gene family sequences for the design of RT-PCR primers and probe for MAGE-A3. Sequence alignment of MAGE-A family members around the site of the RT-PCR primers designed for the TaqMan MGB RT-PCR. The probe is located in the middle of the amplicon. The oligonucleotide primers and probe were designed to hybridise in areas of greatest difference between MAGE-A3 and the other family members. The forward primer is SEQ ID NO: 3; the reverse primer is SEQ ID NO:4 and the probe is SEQ ID NO:13.

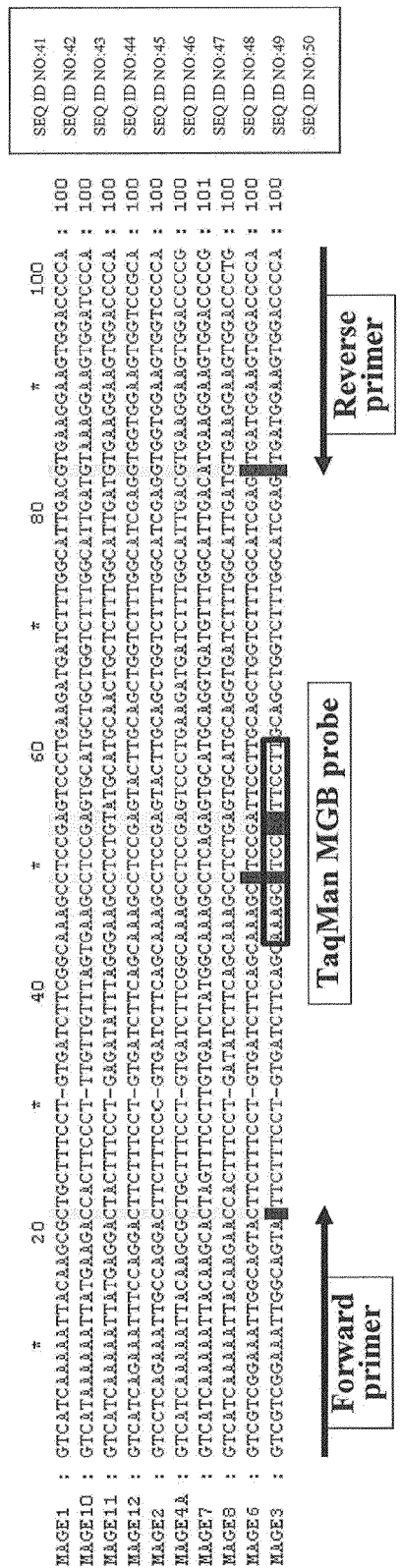

FIG. 15

Comparison of MAGE-A3 (SEQ ID NO:51) and MAGE-A6 (SEQ ID NO:52)

```
MAGE-A3 ccaagcagcactcagtaggaaggtggccgagttggttcattttctgctcctcaagtatcg
        ||||||||||||||||||||||||||||||||              |||||||
MAGE-A6 ccaagcagcactcagtaggaaggtggccaagttggttcattttctgctcctcaagtatcg
                                         MAGEA3f-623F    E3 MAGE3 TMF
MAGE-A3 agccagggagccggtcacaaaggcagaaatgctgggga[tgtc]tcggaaattggcagta
        |||||| |||||||||||||||||||||||||||||||||||||||||||||||||||
MAGE-A6 agccagggagccggtcacaaaggcagaaatgctggggagtgtcgtcggaaattggcagta
             MAGEA3f-651Tm   E3 MAGE3 TMP   MAGEA3f-697R
MAGE-A3 [t]tctttcctgtgatcttcagcaaacttccagttcct gcagctggtctttggcatcga
           |||| |||||||||||||||||| ||||| |||||||||||||||||||||||
MAGE-A6 cttctttcctgtgatcttcagcaaagcttccgattcctgcagctggtctttggcatcga
           E3 MAGE3 TMR
MAGE-A3 gctgatggaagtggacccca]cggccacttgtacatctttgccacctgcctgggcctctc
        ||||||||||||||||||||||  |||||||
MAGE-A6 gctgatggaagtggacccca[cggccacgtgtacatctttgccacctgcctgggcctctc
                    MAGEA3-775F              MAGEA3-801TMCF
MAGE-A3 ctacgatggc[tgctgggtgacaatcagatcat]gcc[aaggcaggcctcct]gataatcgt
        ||||||||||||||||||||||||||||||||||||||    |||||   ||||||
MAGE-A6 ctacgatggcctgctgggtgacaatcagatcatgcccaagacaggcttcctgat atcat
              MAGEA3-849R
MAGE-A3 cctgg[cataatcgcaagagagggc]actgtgcccctgaggagaaaatctggggaggagct
        ||||| ||||||||||||
MAGE-A6 cctggccat atcgcaaaagagggcgactgtgcccctgaggagaaaatctggggaggagct MAGE-A3 gagtgtgttagaggtgtttgaggggagggaagacagtatcttggggatcccaagaagct
        |||||||||||||||||||||||||||||||||||||||||| ||||
MAGE-A6 gagtgtgttagaggtgtttgaggggagggaagacagtatcttcggggatcccaagaagct
                MAGEA3e-950F
MAGE-A3 gctcad[ccaacatttcgtgcaggaa]aactacctggagtaccggcaggtccccggca]gtga]
        ||||||    ||||
MAGE-A6 gctcacccaatatttcgtgcaggaaaactacctggagtaccggcaggtccccggcagtga
        MAGEA3e-1000Tmc   MAGEA3e-1037R
MAGE-A3 [tcctgcatgttatgaattcctgt gggtccaagg]ccctcgttgaaaccagctatgtgaa
        |||||||||||| ||||| ||||||||||||||||||| ||||||||||||||||||
MAGE-A6 tcctgcatgctatgagttcctgtggggtccaagggccctcattgaaaccagctatgtgaa MAGE-A3 agtcctgcaccatatggtaaagatcagtggaggacctcacatttcctacccaccctgca
        |||||||||||||||||||||||||||||||||||||||||| ||||||||||||||||
MAGE-A6 agtcctgcaccatatggtaaagatcagtggaggacctcgcatttcctacccactcctgca
```

Graphical Comparison of Ct values from MAGE-A Plasmids using
20, 2, 0.2 0.02 pg of DNA Graphical Comparison of Delta Ct values Relative to MAGE-A3 for other MAGE-A Plasmids using 20, 2, 0.2 0.02 pg of DNA Linearity of FFPE Xenograft GERL RNA - 2- fold serial dilutions from 100 to 0.1 ng of RNA Input Delta Ct vs. Log (Base 2) RNA input for FFPE Xenograft GERL RNA

FIG. 21

*Table 1. Oligonucleotide primers used for semi-quantitative MAGE RT-PCR*

| SEQ ID NOs | Name | Sequence | Specificity | Amplicon gDNA | mRNA |
|---|---|---|---|---|---|
| SEQ ID NO: 1 | MAGE3-E2F | TGGAGGACCAGAGGCCCCC | MAGE-A3 | 805 bp | 725 bp |
| SEQ ID NO: 2 | MAGE3-E3R | GGACGATTATCAGGAGGCCTGC | | | |
| SEQ ID NO: 18 | B-actin-E4F | GGCATCGTGATGGACTCCG | β-actin | 615 bp + 830 bp | 615 bp |
| SEQ ID NO: 19 | B-actin-E6R | GCTGGAAGGTGGACAGCGA | | | |

F= forward, R=Reverse, bp=base pairs

FIG. 22

*Table 2. Oligonucleotide primers and probes used for Taqman quantitative RT-PCR*

|  | Name | Sequence | Primer | Dye |
|---|---|---|---|---|
|  | *Exon 3 MAGE-A3 specific primers* | | | |
| SEQ.ID NO: 3 | E3 MAGE3 TMF | GTCGTCGGAAATTGGCAGTAT | Forward | FAM; NFQ-MGB |
| SEQ ID NO: 4 | E3 MAGE3 TMR | TGGGGTCCACTTCCATCAG | Reverse | |
| SEQ ID NO: 13 | E3 MAGE3 TMP | AAAGCTTCCAGTTCCTT | Probe | |
|  | *Intron 3 MAGE-A3 specific primers* | | | |
| SEQ ID NO: 5 | I3 MAGE3 TMF | TAAGCCTTTGTTAGAGCCTCCAA | Forward | NED; NFQ-MGB |
| SEQ ID NO: 6 | I3 MAGE3 TMR | GGAGAGAGGGAGCATGTGAGA | Reverse | |
| SEQ ID NO: 14 | I3 MAGE3 TMP | TTCCATTCAGTACTCAG | Probe | |
|  | *Beta-actin specific primers* | | | |
| SEQ ID NO: 20 | B-actin-TMF | CTGGAACGGTGAAGGTGACA | Forward | VIC; NFQ-MGB |
| SEQ ID NO: 21 | B-actin-TMR | CGGCCACATTGTGAACTTTG | Reverse | |
| SEQ ID NO: 22 | B-actin-TMP | TGCTCGCTCCAACC | Probe | |

FIG. 23
Table 3

| RT-PCR | TaqMan PCR | | Total |
| --- | --- | --- | --- |
| | Negative | Positive | |
| Negative | 40 | 0 | 40 |
| Positive | 3 | 28 | 31 |
| Total | 43 | 28 | 71 |

FIG. 24
Table 4

Ct Values

|  | MAGE-3 exon | | MAGE-3 intron | | Beta-Actin | |
| --- | --- | --- | --- | --- | --- | --- |
|  | RGI | GSK | RGI | GSK | RGI | GSK |
| TC1 | 40.00 | 40.00 | 40.00 | 40.00 | 39.25 | 37.40 |
| p815 | 34.07 | 33.94 | 40.00 | 40.00 | 33.22 | 32.76 |
| GERL | 31.77 | 31.38 | 34.45 | 33.83 | 23.11 | 22.69 |
| CRL 1675 | 33.19 | 32.90 | 34.63 | 34.53 | 21.68 | 21.43 |
| 990118 | 33.11 | 32.99 | 35.13 | 34.23 | 23.63 | 23.17 |
| 990010 | 37.42 | 40.00 | 40.00 | 40.00 | 23.03 | 22.67 |
| 990101 | 35.81 | 36.10 | 37.94 | 38.57 | 23.86 | 23.48 |
| 990102 | 38.19 | 38.74 | 40.00 | 39.42 | 26.94 | 26.56 |
| 990133 | Quantity Not Sufficient | | | | | |
| 990152 | 35.97 | 37.61 | 39.22 | 38.44 | 23.36 | 23.00 |
| 990159 | 36.80 | 36.73 | 37.77 | 37.52 | 26.66 | 26.27 |
| 990784 | 35.90 | 38.13 | 36.77 | 37.90 | 26.54 | 26.09 |

FIG. 25
Table 5

| SEQ ID NO | SEQUENCE SET/NAME | SEQUENCE | 5' LABEL | 3' LABEL |
|---|---|---|---|---|
|  | SET 1 (ds) |  |  |  |
| 15 | MAGEA3-801Tmc | CAG GAG GCC TGC CTT | 6-FAM | MGBNFQ |
| 7 | MAGEA3-775F | TGCTGGGTGACAATCAGATCAT | Amplicon size: 75bp | |
| 8 | MAGEA3-849R | CGCCCTCTCTTGCGATTATG | | |
|  | SET 2 (ds) |  |  |  |
| 16 | MAGEA3e-1000Tmc | TTCATAACATGCAGGATCAC | 6-FAM | MGBNFQ |
| 9 | MAGEA3e-950F | CCAACATTTCGTGCAGGAA | Amplicon: 88bp; Tm 82 C | |
| 10 | MAGEA3e-1037R | CCTTGGACCCCACAGGAA | | |
|  | SET 3 (ds) |  |  |  |
| 17 | MAGEA3f-651Tm | CCT GTG ATC TTC AGC AAA | 6-FAM | MGBNFQ |
| 11 | MAGEA3f-623F | TGTCGTCGGAAATTGGCAGTAT | Amplicon size: 75 bp; 79 C | |
| 12 | MAGEA3f-697R | CAAAGACCAGCTGCAAGGAACT | | |

FIG. 26

Table 7
COBAS™ TaqMan MAGE-A3 Primer and Probe Sequences

| COBAS™ TaqMan MAGE-A3 Primer Sequences | |
|---|---|
| MAGEA3f-623F: (HW_MAGEA3_F; SEQ ID NO: 11) | 5'TGTCGTCGGAAATTGGCAGTAT3' |
| MAGEA3f-697R:(HW_MAGEA3_R; SEQ ID NO: 12) | 5'CAAAGACCAGCTGCAAGGAACT3' |
| COBAS™ TaqMan MAGE-A3 Probe Sequence | |
| MAGEA3F-646MOD SEQ ID NO: 53 | 5'-ELFLLLFFLQGLGALFLLFAGFAAAGFLLFP-3' |

E= FAM Reporter Dye, F= 5-Methyl dC, Q = BHQ2 Quencher, L = 5-Propynyl dU,
P= Phosphate, I = HEX Reporter MAGEA3F-646MOD probe sequence comprises the following modified nucleotides (SEQ ID NO:54):

5' - TCTTTCCTGTGATCTTCAGCAAAGCTTC - 3'

FIG. 27

Table 8
*COBAS TaqMan beta-actin Primer and Probe Sequences*

| TaqMan beta-actin Primer Sequences | |
|---|---|
| RGI_BACT_F2: (SEQ ID NO: 55) | 5'-GAGCGCGGCTACAGCTT-3' |
| RGI_BACT_R2: (SEQ ID NO:56) | 5'-TCCTTAATGTCACGCACGATTT-3' |
| TaqMan beta-actin Probe Sequence | |
| HW_RGIBACT_H: (SEQ ID NO:57) | 5'-IACCACCAQCGGCCGAGCGGP-3' |

E= FAM Reporter Dye, F= 5-Methyl dC, Q = BHQ2 Quencher, L = 5-Propynyl dU,
P= Phosphate, I = HEX Reporter

FIG. 28

Table 9

*Sample & Control Valid CT range*

| Controls | Valid Ct Range |
|---|---|
| FFPET Sample Mage Gene 50ng FAM | <35.2 |
| FFPET Sample Bactin Gene 50n HEX | <32.1 |
| 100% Gerl Mage Gene 50ng FAM | 26.0-29.5 |
| 100% Gerl Bactin Gene 50ng HEX | 24.0-27.0 |
| 1% Gerl Mage Gene 0.5ng FAM | 33.0-35.5 |
| 1% Gerl Bactin Gene 0.5ng HEX | 29.0-32.5 |
| 100% UHR Mage Gene 50ng FAM | 25.0-28.0 |
| 100% UHR Bactin Gene 50ng HEX | 22.0-25.0 |
| 1% UHR Mage Gene 0.5ng FAM | 31.0-33.0 |
| 1% UHR Bactin Gene 0.5ng HEX | 27.0-29.0 |
| P53 Positive Control DNA 20ng FAM | 26.5-29.0 |
| Negative Control (NC) | >38.0 |

FIG. 29

Table 10

*Thermal cycling profile*

PCR Thermal Profile for MAGE-A3 Exclusivity Experiment

| Steps | Description | Temperature | Time | Cycle number |
|---|---|---|---|---|
| 1 | UNG Decontamination | 50°C | 5 min. | 1X |
| 2 | Denaturation | 95°C | 15 sec. | 2X |
|   | Annealing | 63°C | 25 sec. |  |
| 3 | Denaturation | 92°C | 15 sec. | 53X |
|   | Annealing | 63°C | 50 sec. |  |
| 4 | Post Cycle | 40°C | 2 min. | 1X |

FIG. 30

Table 11

*RT-PCR Thermal Profile for Linearity and RT-PCR Efficiency, Analytical Sensitivity (Limit of Detection), Method Correlation, and Reproducibility Experiments*

| Steps | Description | Temperature | Time | Cycle number |
|---|---|---|---|---|
| 1 | UNG Decontamination | 50°C | 5 min. | 1X |
| 2 | Denaturation | 95°C | 1 min. | 1X |
| 3 | Reverse Transcription | 60°C | 20 min. | 1X |
| 4 | Denaturation | 95°C | 15 sec. | 2X |
|   | Annealing | 63°C | 25 sec. |  |
| 6 | Denaturation | 92°C | 15 sec. | 53X |
|   | Annealing | 63°C | 50 sec. |  |
| 7 | Post Cycle | 40°C | 2 min. | 1X |

Relatively high anneal temperature of 63°C was implemented to improve MAGE-A3 specificity relative to the other MAGE-A family members.

FIG. 31

Table 12: Ct values from MAGE-A Plasmids using 20, 2, 0.2 0.02 pg of DNA

| Input | Curie A1 | Curie A2 | Curie A3 | Curie A4 | Curie A6 | Curie A8 | Curie A9 | Curie A10 | Curie A11 | Curie A12 |
|---|---|---|---|---|---|---|---|---|---|---|
| 20pg | 55.0 | 55.0 | 18.5 | 51.0 | 27.8 | 35.1 | 34.1 | 51.1 | 46.4 | 46.5 |
| 2pg | 50.9 | 55.0 | 20.7 | 55.0 | 29.1 | 37.2 | 36.7 | 55.0 | 55.0 | 55.0 |
| 0.2pg | 55.0 | 55.0 | 24.4 | 55.0 | 32.2 | 55.0 | 50.5 | 55.0 | 55.0 | 55.0 |
| 0.02pg | 55.0 | 55.0 | 27.2 | 51.0 | 35.4 | 55.0 | 51.0 | 55.0 | 55.0 | 55.0 |

Table 13: Delta Ct Values Relative to MAGE-A3 for other MAGE-A Plasmids using 20, 2, 0.2 0.02 pg of DNA

| Input | Curie A1 | Curie A2 | Curie A3 | Curie A4 | Curie A6 | Curie A8 | Curie A9 | Curie A10 | Curie A11 | Curie A12 |
|---|---|---|---|---|---|---|---|---|---|---|
| 20pg | 32.6 | 36.5 | 0.0 | 32.5 | 9.3 | 16.6 | 15.6 | 32.6 | 27.8 | 28.0 |
| 2pg | 30.1 | 34.3 | 0.0 | 34.3 | 8.4 | 16.5 | 16.0 | 34.3 | 34.3 | 34.3 |
| 0.2pg | 30.6 | 30.6 | 0.0 | 30.6 | 7.8 | 30.6 | 26.1 | 30.6 | 30.6 | 30.6 |
| 0.02pg | 27.8 | 27.8 | 0.0 | 23.8 | 8.2 | 27.8 | 23.8 | 27.8 | 27.8 | 27.8 |

FIG. 32

Table 14: MAGE-A3 Exclusivity Experiment Validation

| Control | Run1 | Run2 | Run3 | Run4 | Run5 | Run6 | Run7 | Run8 |
|---|---|---|---|---|---|---|---|---|
| P53 (20ng) | 28.3 | 28.3 | 28.6 | 28.2 | 28.4 | 28.5 | 28.6 | 28.5 |
| NC | >38.0 | >38.0 | >38.0 | >38.0 | >38.0 | >38.0 | >38.0 | >38.0 |
| NC | >38.0 | >38.0 | >38.0 | >38.0 | >38.0 | >38.0 | >38.0 | >38.0 |
| NC | >38.0 | >38.0 | >38.0 | >38.0 | >38.0 | >38.0 | >38.0 | >38.0 |

Control Cts were within validated range. Experiment passed validation.

FIG. 33

*Tables 15 and 16: MAGE-A3 Exclusivity Experiment Details*

| Item/Reagent | ID/Lot |
|---|---|
| MMX (Universal) | CW120406 |
| Primer/Probe | JL011507 |
| MgOAc MnOAc Blend | CW012607 |
| p53 0.4ng/ul | 120506HL |
| H$_2$O | C08E41 |
| P-1000 | 3250 |
| P-200 | 3248 |
| P-20 | 3244 |
| Biosafety Hood | 6 |

| k-tray | Lot | CTM48 |
|---|---|---|
| 72910 | 6004153 | 1093 |
| 72512 | 6004153 | 1093 |
| 72867 | 6004153 | 1012 |
| 72561 | 6004153 | 1012 |
| 78933 | 6004153 | 1074 |
| 78804 | 6004153 | 1074 |
| 78950 | 6004153 | 108 |
| 78852 | 6004153 | 108 |

Digital Data Storage Location: J:\Discovery Research\GeneExpProfile\GSK\IDE Experiments\Mage Exclusivity
Notebook References: HL38027, JL38664, KM34771

FIG. 34

Table 17: Linearity MAGE-A3 and β-Actin Ct and Delta Ct from 10 replicates at 11 Levels

| Xenograft GERL-b in Water (n=10) | | | | | | | | | | |
|---|---|---|---|---|---|---|---|---|---|---|
| | | Curie-A3 | | | Bactin | | | Delta Ct | | |
| Dilution | RNA Input (ng) | Av Ct | STD | %CV | Av Ct | STD | %CV | Delta Ct | Stdev | %CV |
| 1 | 100 | 28.0 | 0.097 | 0.35% | 24.4 | 0.086 | 0.35% | 3.6 | 0.05 | 1.47% |
| 2 | 50 | 28.7 | 0.087 | 0.30% | 25.3 | 0.044 | 0.17% | 3.4 | 0.07 | 1.97% |
| 3 | 25 | 29.6 | 0.100 | 0.34% | 26.3 | 0.069 | 0.26% | 3.3 | 0.11 | 3.30% |
| 4 | 12.5 | 30.3 | 0.073 | 0.24% | 27.2 | 0.070 | 0.26% | 3.1 | 0.07 | 2.31% |
| 5 | 6.25 | 31.4 | 0.126 | 0.40% | 28.3 | 0.075 | 0.27% | 3.1 | 0.14 | 4.61% |
| 6 | 3.13 | 32.1 | 0.158 | 0.49% | 29.2 | 0.034 | 0.12% | 2.9 | 0.18 | 6.27% |
| 7 | 1.56 | 33.1 | 0.219 | 0.66% | 30.0 | 0.073 | 0.24% | 3.0 | 0.19 | 6.41% |
| 8 | 0.78 | 33.9 | 0.162 | 0.48% | 31.0 | 0.057 | 0.18% | 2.9 | 0.17 | 5.91% |
| 9 | 0.39 | 34.9 | 0.347 | 0.99% | 32.0 | 0.169 | 0.53% | 3.0 | 0.27 | 9.02% |
| 10 | 0.20 | 36.3 | 0.682 | 1.88% | 33.0 | 0.223 | 0.68% | 3.3 | 0.78 | 23.49% |
| 11 | 0.10 | 36.9 | 0.745 | 2.02% | 34.0 | 0.244 | 0.72% | 2.9 | 0.73 | 25.04% |

FIG. 35

Table 18: RT-PCR Amplification Efficiency of MAGE-A3 and β-actin

| 100 - 0.1 ng RNA Input | Slope | AE | % Efficiency |
|---|---|---|---|
| MAGE-A3 | -0.9108 | 2.14 | 107.0 |
| β-actin | -0.9582 | 2.06 | 103.1 |

FIG. 36

*Table 19: Linearity / RT-PCR Efficiency Experiment Validation*

| NC | Run1 | Run2 | Run3 | Run4 | Run5 | Run6 | Run7 | Run7 | Run7 | Run7 |
|---|---|---|---|---|---|---|---|---|---|---|
| MAGE-FAM | >38.0 | >38.0 | >38.0 | >38.0 | >38.0 | >38.0 | >38.0 | >38.0 | >38.0 | >38.0 |
| MAGE-FAM | >38.0 | >38.0 | >38.0 | >38.0 | >38.0 | >38.0 | >38.0 | >38.0 | >38.0 | >38.0 |
| MAGE-FAM | >38.0 | >38.0 | >38.0 | >38.0 | >38.0 | >38.0 | >38.0 | >38.0 | >38.0 | NA |
| MAGE-FAM | >38.0 | >38.0 | >38.0 | >38.0 | >38.0 | >38.0 | >38.0 | >38.0 | >38.0 | NA |
| Bactin-HEX | >38.0 | >38.0 | >38.0 | >38.0 | >38.0 | >38.0 | >38.0 | >38.0 | >38.0 | >38.0 |
| Bactin-HEX | >38.0 | >38.0 | >38.0 | >38.0 | >38.0 | >38.0 | >38.0 | >38.0 | >38.0 | >38.0 |
| Bactin-HEX | >38.0 | >38.0 | >38.0 | >38.0 | >38.0 | >38.0 | >38.0 | >38.0 | >38.0 | NA |
| Bactin-HEX | >38.0 | >38.0 | >38.0 | >38.0 | >38.0 | >38.0 | >38.0 | >38.0 | >38.0 | NA |

Control Cts were within validated range. Experiment passed validation.

FIG. 37

Tables 20, 21 and 22: Linearity / RT-PCR Efficiency Experiment Details

Table 20

| Isolation Reagents | Lot Number | Expiration Date |
|---|---|---|
| Buffer PKD | 121100445 | 01/2007 |
| Proteinase K | 12199252 | 01/2007 |
| Buffer RBC | 12199582 | 01/2007 |
| gDNA Eliminator Column | 12198612 | 01/2007 |
| Ethanol | 64209 (Sigma) | 01/2007 |
| RNeasy MinElute Column | 121100265 | 01/2007 |
| DNase I | 12411639 | 01/2007 |
| RDD | 11877821 | 01/2007 |
| Buffer RWT | Research Lot | 01/2007 |
| Buffer RPE | 12199510 | 01/2007 |
| RNase-free Water | 12199577 | 01/2007 |

Table 21

| Item/Reagent | ID/Lot |
|---|---|
| MMX (Universal) | CW120406 |
| Primer/Probe | JL011507 |
| MgOAc MnOAc Blend | HW121906 |
| Gerl-b | 11507 |
| Stac-b | 11507 |
| UHR | 760380 |
| $H_2O$ | C08E41 |
| P-1000 | 3250 |
| P-200 | 3248 |
| P-20 | 3244 |
| Biosafety Hood | 6 |

Table 22

| k-tray | Lot | CTM48 |
|---|---|---|
| 78848/78790 | 6004153 | 1012 |
| 78817/78864 | 6004153 | 1069 |
| 72893/72957 | 6004153 | 1071 |
| 78944/78871 | 6004153 | 105 |
| 78793/78813 | 6004153 | 1067 |
| 78847/78919 | 6004153 | 1072 |
| 79010 | 6004153 | 1074 |

FIG. 38

Table 23: MAGE-A3 Ct Hit Rate, N = 24 for Each Condition

| Total Input | 0.5%Gerl 99.5%Stac | 1%Gerl 99%Stac | 5%Gerl 95%Stac |
|---|---|---|---|
| 12.5ng | 0/24 | 4/24 | 24/24 |
| 25ng | 6/24 | 20/24 | 24/24 |
| 50ng | 23/24 | 24/24 | 24/24 |
| 100ng | 18/24 | 24/24 | 24/24 |

FIG. 39

Table 24: MAGE-A3 Ct Hit Rate Percentage, N = 24 for Each Condition

| Total Input | 0.5%Gerl 99.5%Stac | 1%Gerl 99%Stac | 5%Gerl 95%Stac |
|---|---|---|---|
| 12.5ng | 0% | 16.7% | 100% |
| 25ng | 25% | 83.3% | 100% |
| 50ng | 95.8% | 100% | 100% |
| 100ng | 75% | 100% | 100% |

Table 25: β-actin Ct Hit Rate, N = 24 for Each Condition

| Total Input | 0.5%Gerl 99.5%Stac | 1%Gerl 99%Stac | 5%Gerl 95%Stac |
|---|---|---|---|
| 12.5ng | 24/24 | 24/24 | 24/24 |
| 25ng | 24/24 | 24/24 | 24/24 |
| 50ng | 24/24 | 24/24 | 24/24 |
| 100ng | 24/24 | 24/24 | 24/24 |

Table 26: β-actin Ct Hit Rate Percentage, N = 24 for Each Condition

| Total Input | 0.5%Gerl 99.5%Stac | 1%Gerl 99%Stac | 5%Gerl 95%Stac |
|---|---|---|---|
| 12.5ng | 100% | 100% | 100% |
| 25ng | 100% | 100% | 100% |
| 50ng | 100% | 100% | 100% |
| 100ng | 100% | 100% | 100% |

FIG. 40

Table 27: MAGE Gene FAM Control Cts

| Control | Run4C | Run4D | Run5A | Run6C | Run6D | Run7A | Run8C | Run8D | Run9A | Run7B | Run10C | Run10D | Run11A | Run11B | Run12B | Run12BB |
|---|---|---|---|---|---|---|---|---|---|---|---|---|---|---|---|---|
| 1% Gerl | 33.20 | 33.73 | 33.29 | 33.01 | 33.60 | 34.03 | 33.34 | 33.08 | 33.34 | 33.50 | 33.11 | 33.55 | 34.96 | 34.21 | 34.21 | 35.11 |
| 1%UHR | 32.00 | 31.79 | 32.28 | 31.87 | 31.79 | 32.03 | 31.92 | 31.69 | 31.60 | 31.64 | 31.57 | 31.89 | 31.87 | 31.70 | 31.96 | 31.91 |
| 100% Gerl | 27.35 | 27.31 | 27.36 | 27.34 | 27.38 | 27.57 | 27.76 | 27.62 | 28.04 | 27.51 | 27.75 | 28.02 | 27.83 | 27.60 | 27.82 | 28.05 |
| 100% UHR | 25.33 | 25.34 | 25.39 | 25.31 | 25.34 | 25.48 | 25.85 | 25.44 | 25.92 | 25.63 | 25.65 | 25.76 | 26.06 | 25.92 | 25.97 | 26.20 |
| NC | >38.0 | >38.0 | >38.0 | >38.0 | >38.0 | >38.0 | >38.0 | >38.0 | >38.0 | >38.0 | >38.0 | >38.0 | >38.0 | >38.0 | >38.0 | >38.0 |

Table 28: β-actin HEX Control Cts

| Control | Run4C | Run4D | Run5A | Run6C | Run6D | Run7A | Run8C | Run8D | Run9A | Run7B | Run10C | Run10D | Run11A | Run11B | Run12B | Run12BB |
|---|---|---|---|---|---|---|---|---|---|---|---|---|---|---|---|---|
| 1% Gerl | 30.30 | 30.81 | 30.76 | 29.65 | 30.56 | 30.83 | 30.55 | 30.49 | 30.44 | 30.68 | 30.41 | 30.93 | 31.47 | 31.58 | 31.39 | 31.23 |
| 1%UHR | 27.58 | 27.38 | 27.75 | 27.74 | 27.90 | 27.71 | 27.62 | 27.52 | 27.43 | 27.62 | 27.28 | 27.31 | 27.82 | 27.65 | 27.64 | 27.71 |
| 100% Gerl | 24.82 | 24.57 | 24.74 | 24.71 | 24.70 | 24.93 | 25.07 | 24.78 | 25.41 | 24.82 | 25.00 | 25.23 | 25.04 | 24.89 | 25.04 | 25.15 |
| 100% UHR | 22.21 | 22.18 | 22.22 | 22.20 | 22.16 | 22.36 | 22.63 | 22.28 | 22.83 | 22.59 | 22.41 | 22.45 | 22.92 | 22.67 | 22.71 | 22.99 |
| NC | >38.0 | >38.0 | >38.0 | >38.0 | >38.0 | >38.0 | >38.0 | >38.0 | >38.0 | >38.0 | >38.0 | >38.0 | >38.0 | >38.0 | >38.0 | >38.0 |

Control Cts are within validated range. Experiment passed validation.

FIG. 41

Table 29; Table 30; and Table 31: Limit of Detection Experiment Details

Table 29

| Gerl & Stac Isolation Reagents | Lot Number | Expiration Date |
|---|---|---|
| Buffer PKD | 121100445 | 12/14/2007 |
| Proteinase K | 12199252 | 12/11/2007 |
| Buffer RBC | 124101094 | 12/18/2007 |
| gDNA Eliminator Column | 12198612 | 12/15/2007 |
| Ethanol | 06H07GA | 2/15/2008 |
| RNeasy MinElute Column | 121100265 | 12/6/2007 |
| DNase I | 124119201 | 12/6/2007 |
| RDD | 124115915 | 12/6/2007 |
| Buffer RWT | 124114997 | 12/18/2007 |
| Buffer RPE | 12199510 | 12/15/2007 |
| RNase-free Water | 12199577 | 12/15/2007 |

Table 30

| Item/Reagent | ID/Lot |
|---|---|
| MMX (Universal) | CW120406 |
| Primer/Probe | JL011507 |
| MgOAc MnOAc Blend | CW012607 |
| $H_2O$ | C08E41 |
| UHR | 760380 |
| GERL | RGI 12307 |
| STAC | RGI 12307 |
| P-1000 | 3302 |
| P-1000 | 3303 |
| P-1000 | 3304 |
| P-1000 | 3250 |
| P-1000 | 3369 |
| P-1000 | 1499 |
| P-200 | 3308 |
| P-200 | 3248 |
| P-200 | 3305 |
| P-200 | 1506 |
| P-20 | 3245 |
| P-20 | 3301 |
| P-20 | 3244 |
| ELPH-200 | 3313 |
| ELPH-1000 | 3369 |
| Biosafety Hood | 4,5,6,1574 |

Table 31

| k-tray | Lot | CTM48 |
|---|---|---|
| 78839/78841 | 6004153 | 1012 |
| 78856/78870 | 6004153 | 105 |
| 71641/71692 | 6004153 | 1012 |
| 78920/71697 | 6004153 | 1092 |
| 71755/71690 | 6004153 | 105 |
| 71659/71630 | 6004153 | 1093 |
| 54608/54631 | 6004153 | 1012 |
| 54671/54677 | 6004153 | 101 |
| 54580/54649 | 6004153 | 105 |
| 54587/54282 | 6004153 | 1092 |
| 54592/54619 | 6004153 | 1012 |
| 54481/54585 | 6004153 | 105 |

FIG. 42

Table 32: Cross Validation Summary of Samples

| Cross Validation Results | COBAS | Prototype |
|---|---|---|
| Total Samples Available for Testing | 131 | 131 |
| Sample without gDNA | 123 | 123 |
| Samples OOR | 4 | 10 |
| Insufficient RNA Samples | 2 | 5 |
| Remaining Samples | 117 | 108 |

OOR = MAGE-A3 Expression of the sample above the threshold, but MAGE-A3 Ct outside of the acceptable range.

Insufficient RNA Samples = β-actin Ct outside the acceptable range.

FIG. 43

Table 33: COBAS and prototype Tests Positive and Negative by Comparator Percent Agreement

| prototype vs. COBAS | COBAS Positive | COBAS Negative |
|---|---|---|
| prototype Positive | 59 | 5 |
| prototype Negative | 4 | 39 |

98/107 91.6% Concordance

Positive by Comparator Percent Agreement 59/ 64 or 92.2 %

Negative by Comparator Percent Agreement 39/43 or 90.7 %

Table 34: COBAS and prototype Tests Positive and Negative by Comparator Percent Agreement with frozen Test to Resolve Discordant Results

| RGI vs. RMS with GSK Results to Resolve Discordance | RMS Positive | RMS Negative |
|---|---|---|
| RGI Positive | 63 | 1 |
| RGI Negative | 1 | 42 |

105/107 98.1 % Concordance

Positive by Comparator Percent Agreement 63/64 or 98.4 %

Negative by Comparator Percent Agreement 42/43 or 97.7 %

FIG. 44

Table 35: Experiment Control MAGE Gene Cts

| Control | Run1 | Run2 | Run3 | Run4 | Run5 | Run6 | Run7 | Run8 | RunA | RunB | Run7RX |
|---|---|---|---|---|---|---|---|---|---|---|---|
| 1%Gerl | 34.25 | 34.12 | 34.25 | 33.56 | 33.95 | 34.10 | 34.39 | 34.12 | 33.89 | 34.34 | 33.67 |
| 1%Gerl | 33.58 | 34.27 | 34.18 | 33.57 | 34.42 | 34.37 | 34.22 | 34.20 | 33.80 | 33.54 | NA |
| 100%Gerl | 27.49 | 27.63 | 27.64 | 27.61 | 27.58 | 27.80 | 29.10 | 27.67 | 27.45 | 27.71 | 27.84 |
| 100%Gerl | 27.57 | 27.65 | 27.98 | 27.82 | 27.85 | 27.77 | 28.34 | 27.80 | 27.41 | 27.81 | NA |
| 1%UHR | 31.52 | 31.51 | 31.78 | 32.24 | 32.21 | 32.47 | 32.76 | 31.99 | 31.85 | 32.13 | 32.19 |
| 1%UHR | 31.24 | 31.96 | 32.12 | 32.28 | 32.31 | 32.50 | 32.27 | 32.03 | 32.12 | 31.99 | NA |
| 100&UHR | 25.46 | 25.50 | 25.44 | 25.49 | 25.60 | 25.43 | 27.18 | 25.96 | 25.35 | 25.70 | 26.06 |
| 100%UHR | 25.50 | 25.50 | 25.68 | 25.57 | 25.54 | 25.54 | 26.54 | 25.75 | 25.34 | 25.74 | NA |
| NC | >38 | >38 | >38 | >38 | >38 | >38 | >38 | >38 | >38 | >38 | >38 |
| NC | >38 | >38 | >38 | >38 | >38 | >38 | >38 | >38 | >38 | >38 | NA |

Table 36: Experiment Control β-actin Gene Cts

| Control | Run1 | Run2 | Run3 | Run4 | Run5 | Run6 | Run7 | Run8 | RunA | RunB | Run7RX |
|---|---|---|---|---|---|---|---|---|---|---|---|
| 1%Gerl | 31.08 | 31.09 | 31.06 | 31.08 | 31.42 | 31.33 | 31.94 | 31.36 | 31.15 | 31.53 | 31.12 |
| 1%Gerl | 30.91 | 31.84 | 31.03 | 31.02 | 32.02 | 31.47 | 31.39 | 30.74 | 31.10 | 31.04 | NA |
| 100%Gerl | 24.88 | 24.95 | 24.86 | 25.15 | 25.03 | 25.15 | 26.87 | 24.93 | 24.84 | 25.07 | 25.06 |
| 100%Gerl | 24.60 | 24.63 | 25.07 | 25.13 | 25.17 | 25.07 | 25.98 | 24.57 | 24.68 | 25.16 | NA |
| 1%UHR | 27.50 | 27.65 | 27.82 | 28.03 | 28.33 | 28.61 | 28.49 | 27.80 | 28.10 | 28.14 | 28.06 |
| 1%UHR | 27.31 | 27.95 | 27.95 | 28.03 | 28.41 | 28.37 | 28.47 | 27.39 | 28.08 | 28.07 | NA |
| 100&UHR | 22.30 | 22.33 | 22.37 | 22.39 | 22.51 | 22.44 | 24.35 | 22.71 | 22.19 | 22.50 | 22.97 |
| 100%UHR | 22.36 | 22.32 | 22.58 | 22.44 | 22.36 | 22.40 | 23.59 | 22.40 | 22.22 | 22.57 | NA |
| NC | >38 | >38 | >38 | >38 | >38 | >38 | >38 | >38 | >38 | >38 | >38 |
| NC | >38 | >38 | >38 | >38 | >38 | >38 | >38 | >38 | >38 | >38 | NA |

Control Cts are within validated range. Experiment passed validation.

FIG. 45

Tables 37, 38 and 39- Method Correlation / Cross Validation Experiment Details

Table 37

| Isolation Reagents | Lot Number | Expiration Date |
|---|---|---|
| Buffer PKD | 121100445 | 12/14/2007 |
| Proteinase K | 12199252 | 12/11/2007 |
| Buffer RBC | 124101094 | 12/18/2007 |
| gDNA Eliminator Column | 12198612 | 12/15/2007 |
| Ethanol | 06A49GA | 8/14/2007 |
| RNeasy MinElute Column | 121100265 | 12/6/2007 |
| DNase I | 124119201 | 12/6/2007 |
| RDD | 124115915 | 12/6/2007 |
| Buffer RWT | 124114997 | 12/18/2007 |
| Buffer RPE | 12199510 | 12/15/2007 |
| RNase-free Water | 12199577 | 12/15/2007 |

Table 38

| Item/Reagent | ID/Lot |
|---|---|
| MMX (Universal) | CW120406 |
| Primer/Probe | JL011507 |
| MgOAc MnOAc Blend | CW012607 |
| $H_2O$ | C08E41 |
| UHR | 760380 |
| GERL | RGI 12307 |
| STAC | RGI 12307 |
| P-200 | 3248 |
| P-200 | 3305 |
| P-200 | 3308 |
| P-20 | 3244 |
| P-20 | 3245 |
| P-20 | 3301 |
| P-2 | 3307 |
| P-1000 | 3303 |
| P-1000 | 3304 |
| P1000 | 3250 |
| P-10 | 3306 |
| ELPH P-1000 | 3314 |
| Biosafety Hood | 4,5,6 |

Table 39

| k-tray | Lot | CTM48 |
|---|---|---|
| 72568/72637 | 6004153 | 1092 |
| 72993/72552 | 6004153 | 1095 |
| 72498/72495 | 6004153 | 105 |
| 72583/72540 | 6004153 | 1092 |
| 72490/72596 | 6004153 | 1093 |
| 72590/72641 | 6004153 | 1012 |
| 73016/72592 | 6004153 | 1069 |
| 72930/78783 | 6004153 | 1071 |
| 72620/72541 | 6004153 | 1012 |
| 72530/75252 | 6004153 | 1067 |
| 54581 | 6004153 | 1012 |

Digital Data Storage Location: J:\Discovery Research\GeneExpProfile\GSK\IDE Experiments\Cross Validation
Notebook References: JL38664, LC38028, HL38027, KM38662, KM34771

FIG. 46

Table 40: Run 1 — MAGE-A3 Expression Threshold from GERL RNA Controls

| GERL RNA Control | 100% β-actin | 1% Curie | Delta Ct | Curie-A3 Threshold |
|---|---|---|---|---|
| Replicate1 | 24.56 | 33.48 | -8.92 | 2.06E-03 |
| Replicate2 | 24.47 | 33.29 | -8.82 | 2.21E-03 |
| Average | 24.51 | 33.39 | -8.87 | 2.13E-03 |

Table 41: Run 1 — MAGE-A3 Expression Call for Reproducibility Specimens

| RGI Accession # | Sample ID | Mage A3 CT | Bactin CT | Delta | Expression | % Gerl | Mage Call |
|---|---|---|---|---|---|---|---|
| AGG-07-0000580 | 990105 | 46.0 | 24.4 | -21.6 | 3.25383E-07 | 0.00 | Negative |
| AGG-07-0000580 | 990105 | 36.3 | 24.5 | -11.9 | 0.000268087 | 0.13 | Negative |
| AGG-07-0000581 | 990112 | 46.0 | 24.3 | -21.7 | 2.96142E-07 | 0.00 | Negative |
| AGG-07-0000581 | 990112 | 36.5 | 24.4 | -12.1 | 0.000226088 | 0.11 | Negative |
| AGG-07-0000582 | 990116 | 36.6 | 26.2 | -10.3 | 0.000770965 | 0.36 | Negative |
| AGG-07-0000582 | 990116 | 36.0 | 26.0 | -10.1 | 0.000936414 | 0.44 | Negative |
| AGG-07-0000583 | 990117 | 46.0 | 23.6 | -22.4 | 1.8283E-07 | 0.00 | Negative |
| AGG-07-0000583 | 990117 | 37.7 | 23.6 | -14.1 | 5.75628E-05 | 0.03 | Negative |
| AGG-07-0000584 | 990131 | 36.1 | 25.8 | -10.3 | 0.000804481 | 0.38 | Negative |
| AGG-07-0000584 | 990131 | 36.2 | 25.7 | -10.5 | 0.000692747 | 0.32 | Negative |
| AGG-07-0000585 | 990619 | 32.9 | 25.4 | -7.5 | 0.005560602 | 2.61 | Positive |
| AGG-07-0000585 | 990619 | 33.1 | 25.5 | -7.7 | 0.004921188 | 2.31 | Positive |
| AGG-07-0000586 | 991157 | 29.2 | 22.2 | -7.0 | 0.007818891 | 3.66 | Positive |
| AGG-07-0000586 | 991157 | 29.3 | 22.3 | -7.0 | 0.007812905 | 3.66 | Positive |
| AGG-07-0000587 | 991158 | 26.4 | 24.4 | -2.0 | 0.250968781 | 117.61 | Positive |
| AGG-07-0000587 | 991158 | 26.4 | 24.3 | -2.1 | 0.238331954 | 111.69 | Positive |
| AGG-07-0000588 | 990130 | 29.0 | 25.4 | -3.6 | 0.081955519 | 38.41 | Positive |
| AGG-07-0000588 | 990130 | 29.2 | 25.6 | -3.6 | 0.083954419 | 39.34 | Positive |
| AGG-07-0000589 | 990136 | 28.3 | 24.8 | -3.5 | 0.087129355 | 40.83 | Positive |
| AGG-07-0000589 | 990136 | 28.2 | 24.7 | -3.6 | 0.084384326 | 39.54 | Positive |
| AGG-07-0000590 | 395 | 31.3 | 24.1 | -7.3 | 0.006411876 | 3.00 | Positive |
| AGG-07-0000590 | 395 | 31.5 | 24.1 | -7.5 | 0.005674828 | 2.66 | Positive |
| AGG-07-0000591 | 512 | 28.6 | 24.5 | -4.1 | 0.057999545 | 27.18 | Positive |
| AGG-07-0000591 | 512 | 28.6 | 24.4 | -4.2 | 0.053251449 | 24.95 | Positive |

FIG. 47

Table 42: Run 2 — MAGE-A3 Expression Threshold from GERL RNA Controls

| GERL RNA Control | 100% β-actin | 1% Curie | Delta Ct | Curie-A3 Threshold |
|---|---|---|---|---|
| Replicate1 | 25.11 | 34.05 | -8.94 | 2.04E-03 |
| Replicate2 | 25.32 | 34.18 | -8.86 | 2.15E-03 |
| Average | 25.21 | 34.11 | -8.90 | 2.09E-03 |

Table 43: Run 2 — MAGE-A3 Expression Call for Reproducibility Specimens

| RGI Accession # | Sample ID | Mage A3 CT | Bactin CT | Delta | Expression | % Gerl | Mage Call |
|---|---|---|---|---|---|---|---|
| AGG-07-0000568 | 990105 | 36.1 | 26.1 | -10.0 | 0.001006688 | 0.48 | Negatvie |
| AGG-07-0000568 | 990105 | 46.0 | 26.1 | -19.9 | 1.0005E-06 | 0.00 | Negatvie |
| AGG-07-0000569 | 990112 | 46.0 | 26.1 | -19.9 | 9.96715E-07 | 0.00 | Negatvie |
| AGG-07-0000569 | 990112 | 36.8 | 26.2 | -10.5 | 0.000674353 | 0.32 | Negatvie |
| AGG-07-0000570 | 990116 | 36.9 | 27.2 | -9.7 | 0.001187625 | 0.57 | Negatvie |
| AGG-07-0000570 | 990116 | 36.6 | 27.0 | -9.6 | 0.001318477 | 0.63 | Negatvie |
| AGG-07-0000571 | 990117 | 35.7 | 24.6 | -11.0 | 0.000474819 | 0.23 | Negatvie |
| AGG-07-0000571 | 990117 | 34.8 | 24.7 | -10.1 | 0.000887085 | 0.42 | Negatvie |
| AGG-07-0000572 | 990131 | 46.0 | 26.5 | -19.5 | 1.3292E-06 | 0.00 | Negatvie |
| AGG-07-0000572 | 990131 | 46.0 | 26.3 | -19.7 | 1.17885E-06 | 0.00 | Negatvie |
| AGG-07-0000573 | 990619 | 34.6 | 28.5 | -6.1 | 0.014100789 | 6.74 | Positive |
| AGG-07-0000573 | 990619 | 34.1 | 28.7 | -5.5 | 0.022281952 | 10.65 | Positive |
| AGG-07-0000574 | 991157 | 31.1 | 23.3 | -7.8 | 0.004582971 | 2.19 | Positive |
| AGG-07-0000574 | 991157 | 31.1 | 23.5 | -7.6 | 0.005138918 | 2.46 | Positive |
| AGG-07-0000575 | 991158 | 28.8 | 25.6 | -3.2 | 0.108292659 | 51.75 | Positive |
| AGG-07-0000575 | 991158 | 28.9 | 25.6 | -3.3 | 0.102863278 | 49.15 | Positive |
| AGG-07-0000576 | 990130 | 31.1 | 26.4 | -4.7 | 0.039418402 | 18.84 | Positive |
| AGG-07-0000576 | 990130 | 31.3 | 26.7 | -4.6 | 0.040843351 | 19.52 | Positive |
| AGG-07-0000577 | 990136 | 31.8 | 27.0 | -4.8 | 0.034810768 | 16.63 | Positive |
| AGG-07-0000577 | 990136 | 31.6 | 26.8 | -4.8 | 0.035601088 | 17.01 | Positive |
| AGG-07-0000578 | 395 | 33.6 | 25.6 | -8.0 | 0.004032587 | 1.93 | Positive |
| AGG-07-0000578 | 395 | 33.0 | 25.3 | -7.6 | 0.005000295 | 2.39 | Positive |
| AGG-07-0000579 | 512 | 31.2 | 25.6 | -5.6 | 0.020284412 | 9.69 | Positive |
| AGG-07-0000579 | 512 | 31.2 | 25.4 | -5.8 | 0.018051401 | 8.63 | Positive |

FIG. 48

*Table 44: Reproducibility Validation*

|  | Run 1 Control Cts | | Run 2 Control Cts | |
|---|---|---|---|---|
| Control | MAGE Ct | β-actin Ct | MAGE Ct | β-actin Ct |
| 100% Gerl | 26.5 | 24.6 | 28.1 | 25.1 |
| 100% Gerl | 26.5 | 24.5 | 28.3 | 25.3 |
| 1% Gerl | 33.5 | 32.2 | 34.0 | 30.5 |
| 1% Gerl | 33.3 | 31.9 | 34.2 | 30.6 |
| 100% UHR | 24.8 | 21.3 | 26.1 | 22.8 |
| 100% UHR | 24.6 | 21.2 | 26.3 | 23.0 |
| 1% UHR | 31.6 | 28.6 | 32.1 | 27.3 |
| 1% UHR | 31.6 | 28.5 | 32.0 | 27.3 |
| NC | >38.0 | >38.0 | >38.0 | >38.0 |
| NC | >38.0 | >38.0 | >38.0 | >38.0 |

Control Cts are within validated range. Experiment passed validation.

FIG. 49

*Reproducibility Experiment Details* - Tables 45, 46 and 47

Table 45

| Isolation Reagents Run1 | Lot Number | Expiration Date |
|---|---|---|
| Buffer PKD | 121100445 | 12/14/2007 |
| Proteinase K | 12199252 | 12/11/2007 |
| Buffer RBC | 124101094 | 12/18/2007 |
| gDNA Eliminator Column | 12198612 | 12/15/2007 |
| Ethanol | 06H07GA | 2/15/2008 |
| RNeasy MinElute Column | 121100265 | 12/6/2007 |
| DNase I | 124119201 | 12/6/2007 |
| RDD | 124115915 | 12/6/2007 |
| Buffer RWT | 124114997 | 12/18/2007 |
| Buffer RPE | 12199510 | 12/15/2007 |
| RNase-free Water | 12199577 | 12/15/2007 |

| Isolation Reagents Run2 | Lot Number | Expiration Date |
|---|---|---|
| Buffer PKD | 124113180 | 2/15/2008 |
| Proteinase K | 124125018 | 2/15/2008 |
| Buffer RBC | 124114320 | 2/15/2008 |
| gDNA Eliminator Column | 124125864 | 2/15/2008 |
| Ethanol | 06H07GA | 2/15/2008 |
| RNeasy MinElute Column | 124123928 | 2/15/2008 |
| DNase I | 124124041 | 2/15/2008 |
| RDD | 124122839 | 2/15/2008 |
| Buffer RWT | 124123852 | 2/15/2008 |
| Buffer RPE | 124119688 | 2/15/2008 |
| RNase-free Water | 124123699 | 2/15/2008 |

Table 46

| Item/Reagent | ID/Lot |
|---|---|
| MMX (Universal) | CW120406 |
| Primer/Probe | JL011507 |
| MgOAc MnOAc Blend | CW012607 |
| H$_2$O | C08E41 |
| H$_2$O | EMD Lot# 46201 |
| UHR | 260400 |
| UHR | 760380 |
| GERL | RGI 12307 |
| STAC | RGI 12307 |
| Rainin PipetLite P-1000 | 3302 |
| Rainin PipetLite P-200 | 3307 |
| Rainin PipetLite P-20 | 3244 |
| Rainin PipetLite P-10 | 3306 |
| Rainin PipetLite P-1000 | 3303 |
| Rainin PipetLite P-200 | 3305 |
| Rainin PipetLite P-2 | 3307 |
| Biosafety Hood | 4,5 |

Table 47

| k-tray | Lot | CTM48 |
|---|---|---|
| 54562/54586 | 6004153 | 102 |
| 54669/54591 | 6004153 | 105 |

METHOD FOR THE DETECTION AND DIAGNOSIS OF CANCER INVOLVING PRIMERS AND PROBES FOR THE SPECIFIC DETECTION OF THE MAGE-A3-MARKER

CROSS-REFERENCE TO RELATED APPLICATIONS

This application is filed pursuant to 35 USC §371 as a United States National Phase Application of International Patent Application Serial No. PCT/EP2007/056219 filed on Jun. 21, 2007, which claims the priority of GB 0612342.6 filed on Jun. 21, 2006 in the United Kingdom, each of which is incorporated herein by reference in its entirety.

FIELD OF THE INVENTION

The present invention relates to a diagnostic method for the detection of MAGE-A3. The invention further relates to immunotherapeutic treatment of populations of patients suffering from MAGE-A3 expressing tumours, in which patients having MAGE-A3 expressing tumour tissue have been identified using the diagnostic method described herein.

BACKGROUND

The MAGE (Melanoma antigen) family of genes was originally identified due to the recognition from cytolytic lymphocytes derived from blood lymphocytes of cancer patients (Van der Bruggen et al 1991). The MAGE gene family now comprises over 20 members and is made up of MAGE A, B, C and D genes (Scanlan et al., (2002) Immunol Rev. 188:22-32; Chomez et al., (2001) Cancer Res. 61(14): 5544-51). They are clustered on chromosome X (Lucas et al., 1998 Cancer Res. 58:743-752; Lucas et al., 1999 Cancer Res 59:4100-4103; Lucas et al., 2000 Int J Cancer 87:55-60; Lurquin et al., 1997 Genomics 46:397-408; Muscatelli et al., 1995 Proc Natl Acad Sci USA 92:4987-4991; Pold et al., 1999 Genomics 59:161-167; Rogner et al 1995 Genomics 29:725-731), and have a yet undefined function (Ohman et al. 2001 Exp Cell Res. 265(2):185-94). The MAGE genes are highly homologous and the members of the MAGE-A family, especially, have between 60-98% homology. MAGE genes are not expressed in all normal cells with the exception of expression in spermatogonia and placenta (Haas et al. 1988 Am J Reprod Immunol Microbiol 18:47-51; Takahashi et al. 1995 Cancer Res 55:3478-382).

The re-activation of MAGE gene expression in cancer is due to abnormal de-methylation of the promoter (De Smeet et al. 1996 Proc Natl Acad Sci USA 93(14):7149-53; De Smeet et al. 1999 Mol Cell Biol. 19(11):7327-35). The 12 MAGE-A genes are variably over-expressed in the following cancers: transitional-cell carcinoma, oesophageal carcinoma, melanoma, bladder and non-small cell lung carcinoma (NSCLC) (Scanlan et al. 2002 Immunol Rev. 188:22-32). The over expression and specificity of MAGE expression in cancerous tissues has led the MAGE-A3 protein to be used as an antigen for cancer vaccines (Scanlan et al. 2002 Immunol Rev. 188: 22-32). However, due to the wide range of expression found in cancer patients, the level of expression of MAGE-A3 must be accurately estimated in each patient to direct the vaccination towards patients expressing the protein. MAGE-A3 is often referred to interchangeably as MAGE-3; both are used herein.

Melanoma

Patients presenting with malignant melanoma in distant metastasis (stage IV according to the American Joint Committee on Cancer (AJCC) classification) have a median survival time of one year, with a long-term survival rate of only 5%. Even the standard chemotherapy for stage IV melanoma has therapeutic response rates of only 8-25%, but with no effect on overall survival. Patients with regional metastases (stage III) have a median survival of two to three years with very low chance of long-term survival, even after an adequate surgical control of the primary and regional metastases (Balch et al., 1992 Semin Surg Oncol. 8(6):400-14). Most patients with stage I to III melanoma have their tumour removed surgically, but these patients maintain a substantial risk for relapse. Thus there remains a need to prevent melanoma progression, and to have improved treatment regimes for metastatic melanoma and adjuvant treatments for patients having had a primary tumour removed.

Lung Cancer

There are two types of lung cancer: non-small cell lung cancer (NSCLC) and small cell lung cancer (SCLC). The names simply describe the type of cell found in the tumours. NSCLC includes squamous-cell carcinoma, adenocarcinoma, and large-cell carcinoma and accounts for around 80% of lung cancers. NSCLC is hard to cure and treatments available tend to have the aim of prolonging life as far as possible and relieving symptoms of disease. NSCLC is the most common type of lung cancer and is associated with poor outcomes. Of all NSCLC patients, about 25% have loco-regional disease at the time of diagnosis and are still amenable to surgical excision (stages IB, IIA or IIB according to the AJCC classification). However, more than 50% of these patients will relapse within the two years following the complete surgical resection. There is therefore a need to provide better treatment for these patients.

MAGE-A3 Expression

Previously a number of methods have attempted to measure the expression of MAGE-A3 genes within both cell lines and tumour samples. Semi-quantitative RT-PCR (De Plaen et al. 1994 Immunogenetics 40(5):360-9), other PCR based techniques and also low-density microarray have all been used (Zammatteo et al. 2002 Clinical Chemistry 48(1) 25-34). However in many of these studies a major problem has been the very high homology between the MAGE family members causing false positives. For large Phase II and III trials a quantitative high throughput assay, capable of specifically identifying MAGE-A3-expressing samples and of reducing the likelihood of samples falsely testing-positive, is desirable.

Another difficulty arises with the use of Formalin-Fixed, Paraffin-Embedded (FFPE) tumour tissue, which is the usual method of tumour tissue preservation within clinical centres. The fixation in formalin changes the structure of molecules of RNA within the tissue, causing cross linking and also partial degradation. The partial degradation leads to the creation of smaller pieces of RNA of between 100-300 base pairs. These structural changes to the RNA make it difficult to use RNA extracted from FFPE tissue in conventional diagnostic techniques.

BRIEF DESCRIPTION OF THE DRAWINGS

FIG. 9A-C: Nucleotide sequence encoding fusion protein of Lipoprotein D fragment, Mage3 fragment, and histidine tail, and its respective amino acid sequence (SEQ ID NO: 35 and 36).

FIG. 10A-B: Fusion protein of NS1-MAGE3, and Histidine tail (SEQ ID NO:37)

FIG. 11: DNA coding fusion protein NS1-MAGE3-His (SEQ ID NO:38)

FIG. 12A-B: Fusion protein of CLYTA-MAGE3-Histidine (SEQ ID NO:39)

FIG. 13: DNA for fusion protein CLYTA-MAGE3-His (SEQ ID NO:40)

FIG. 14: Alignment of MAGE-A gene family sequences for the design of RT-PCR primers and probes for MAGE-A3

FIG. 15: Alignment of MAGE-A3 and MAGE-A6 sequences to identify regions containing target sequences (boxed typeface)

FIG. 21 provides Table 1.
FIG. 22 provides Table 2.
FIG. 23 provides Table 3.
FIG. 24 provides Table 4.
FIG. 25 provides Table 5.
FIG. 26 provides Table 7.
FIG. 27 provides Table 8.
FIG. 28 provides Table 9.
FIG. 29 provides Table 10.
FIG. 30 provides Table 11.
FIG. 31 provides Tables 12 and 13.
FIG. 32 provides Table 14.
FIG. 33 provides Tables 15 and 16.
FIG. 34 provides Table 17.
FIG. 35 provides Table 18.
FIG. 36 provides Table 19.
FIG. 37 provides Tables 20, 21 and 22.
FIG. 38 provides Table 23.
FIG. 39 provides Tables 24, 25 and 26.
FIG. 40 provides Tables 27 and 28.
FIG. 41 provides Tables 29, 30 and 31.
FIG. 42 provides Table 32.
FIG. 43 provides Tables 33 and 34.
FIG. 44 provides Tables 35 and 36.
FIG. 45 provides Tables 37, 38 and 39.
FIG. 46 provides Tables 40 and 41.
FIG. 47 provides Tables 42 and 43.
FIG. 48 provides Table 44.
FIG. 49 provides Tables 45, 46, and 47.

DESCRIPTION OF TABLES AND SEQUENCES

Figure 1:
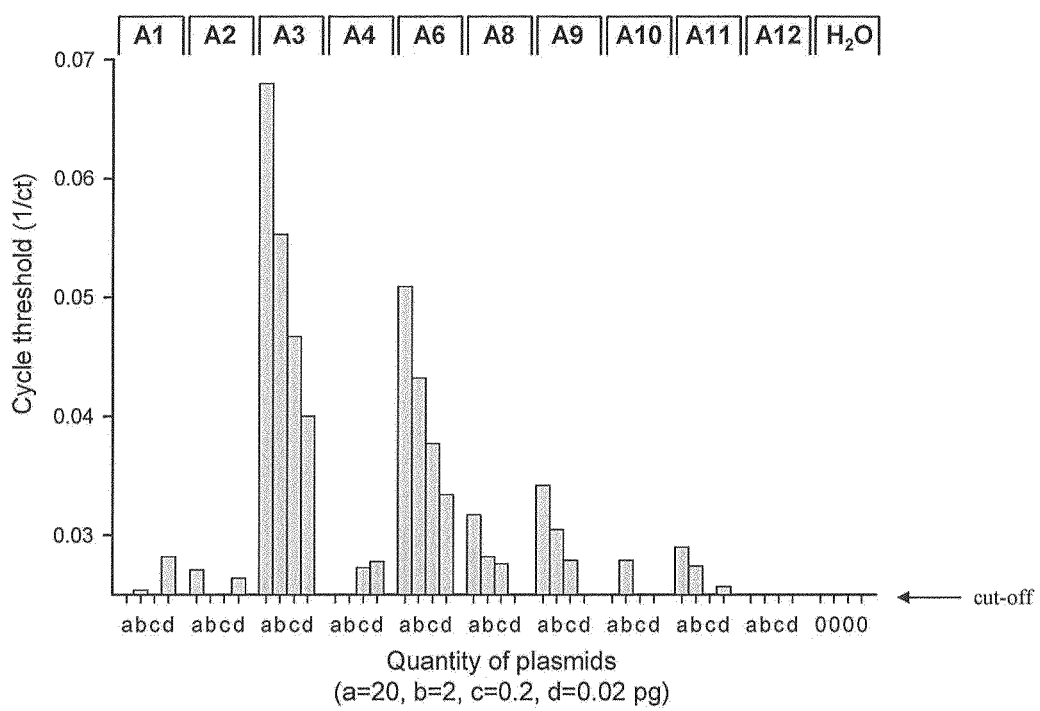
FIG. 1: Specificity of MAGE-A3 RT-PCR TaqMan primers within the MAGE-A family members.

Table 1: Oligonucleotide primers used for semi-quantitative MAGE RT-PCR.

Table 2: Oligonucleotide primers used for the TaqMan quantitative RT-PCR.

Table 3: Comparison of MAGE-A3 semi-quantitative PCR vs quantitative TaqMan PCR.

Table 4: Comparison of Ct and Delta Ct Values using PCR mix 1 and PCR mix 2.

Table 5: Oligonucleotide primers used for MGB TaqMan quantitative RT-PCR from frozen tissue Table 6: Classes for Semi-quantitative MAGE-A3 RT-PCR: an example of how five classes may be assigned to the semi-quantitative MAGE-A3 RT-PCR assay (refers to FIG. 16)

Table 7: COBAS™ TaqMan MAGE-A3 Primer and Probe Sequences

Table 8: COBAS™ TaqMan beta-actin Primer and Probe Sequences

Table 9: COBAS™ TaqMan Sample & Control Valid CT range

Table 10: COBAS™ Taqman Thermal cycling profile—PCR Thermal Profile for MAGE-A3 Exclusivity Experiment Table 11: RT-PCT Thermal Profile for Linearity and RT-PCR Efficiency, Analytical Sensitivity (Limit of Detection), Method Correlation, and Reproducibility Experiments Table 12: Ct values from MAGE-A Plasmids using 20, 2, 0.2 0.02 pg of DNA Table 13: Delta Ct Values Relative to MAGE-A3 for other MAGE-A Plasmids using 20, 2, 0.2 0.02 pg of DNA Table 14: MAGE-A3 Exclusivity Experiment Validation Tables 15 and Table 16: MAGE-A3 Exclusivity Experiment Details Table 17: Linearity MAGE-A3 and β-Actin Ct and Delta Ct from 10 replicates at 11 Levels Table 18: RT-PCR Amplification Efficiency of MAGE-A3 and β-actin Table 19: Linearity/RT-PCR Efficiency Experiment Validation Tables 20, 21 and 22: Linearity/RT-PCR Efficiency Experiment Details Table 23: MAGE-A3 Ct Hit Rate, N=24 for Each Condition Table 24: MAGE-A3 Ct Hit Rate Percentage, N=24 for Each Condition Table 25: β-actin Ct Hit Rate, N=24 for Each Condition Table 26: β-actin Ct Hit Rate Percentage, N=24 for Each Condition Table 27: MAGE Gene FAM Control Cts Table 28: β-actin HEX Control Cts Table 29; Table 30; and Table 31: Limit of Detection Experiment Details Table 32: Cross Validation Summary of Samples Table 33: COBAS and prototype Tests Positive and Negative by Comparator Percent Agreement Table 34: COBAS and prototype Tests Positive and Negative by Comparator Percent Agreement with frozen Test to Resolve Discordant Results Table 35: Experiment Control MAGE Gene Cts Table 36: Experiment Control β-actin Gene Cts Tables 37, 38 and 39: Method Correlation/Cross Validation Experiment Details Table 40: Run 1—MAGE-A3 Expression Threshold from GERL RNA Controls Table 41: Run 1—MAGE-A3 Expression Call for Reproducibility Specimens Table 42: Run 2—MAGE-A3 Expression Threshold from GERL RNA Controls Table 43: Run 2—MAGE-A3 Expression Call for Reproducibility Specimens Table 44: Reproducibility Validation Tables 45, 46 and 47: Reproducibility Experiment Details SEQ ED NO:1—MAGE3-E2F (primer for semi-quantitative MAGE3 assay) (Table 1)

SEQ ID NO:2—MAGE3-E3R (primer for semi-quantitative MAGE3 assay) (Table 1)

SEQ ID NO:3—E3 MAGE3 TMF (forward primer for exon 3 MAGE-A3) (Table 2)

SEQ ID NO:4—E3 MAGE3 TMR (reverse primer for exon 3 MAGE-A3; this primer is the reverse compliment of the MAGE-A3 exon sequence it recognises) (Table 2)

SEQ ID NO:5—I3 MAGE3 TMF (forward primer for intron 3 MAGE-A3) (Table 2)

SEQ ID NO:6—I3 MAGE3 TMR (reverse primer for intron 3 MAGE-A3; this primer is the reverse compliment of the MAGE-A3 intron sequence it recognises) (Table 2)

SEQ ID NO:7—MAGEA3-775F (forward primer for MAGE-A3) (Table 5)

SEQ ID NO:8—MAGEA3-849R (reverse primer for MAGE-A3; this primer is the reverse compliment of the MAGE-A3 sequence it recognises) (Table 5)

SEQ ID NO:9—MAGEA3e-950F (forward primer for MAGE-A3) (Table 5)

SEQ ID NO:10—MAGEA3e-1037R (reverse primer for MAGE-A3; this primer is the reverse compliment of the MAGE-A3 sequence it recognises) (Table 5)

SEQ ID NO:11—MAGEA3f-623F (forward primer for MAGE-A3) (Table 5)

SEQ ID NO:12—MAGEA3f-697R (reverse primer for MAGE-A3; this primer is the reverse compliment of the MAGE-A3 sequence it recognises) (Table 5)

SEQ ID NO:13—E3 MAGE3 TMP (probe for exon 3 MAGE3) (Table 2)

SEQ ID NO:14—I3 MAGE-A3 TMP (probe for intron 3 MAGE3)(Table 2)

SEQ ID NO:15—MAGEA3-801Tmc (probe for MAGE3) (Table 5)

SEQ ID NO:16—MAGEA3e-1000Tmc (probe for MAGE3) (Table 5)

SEQ ID NO:17—MAGEA3f-651Tm (probe for MAGE3) (Table 5)

SEQ ID NO:18—B-actin-E4F (B-actin primer) (Table 1)

SEQ ID NO:19—B-actin-E6R (B-actin primer) (Table 1)

SEQ ID NO:20—B-actin-TMF (B-actin primer) (Table 2)

SEQ ID NO:21—B-actin-TMR (B-actin primer) (Table 2)

SEQ ID NO:22—B-actin TMP (B-actin probe) (Table 2)

SEQ ID NO 23—SEQ ID NO:29: MAGE3 immuno peptides

SEQ ID NO:30—SEQ ID NO:34: adjuvant oligonucleotides

SEQ ID NO:35—nucleotide sequence of fusion protein of Lipoprotein D fragment-MAGE3 fragment-Histidine tail (FIG. 9)

SEQ ID NO:36—amino acid sequence of SEQ ID NO:35 (FIG. 9)

SEQ ID NO:37—amino acid sequence of fusion protein of NS1-MAGE3-histidine tail (FIG. 10)

SEQ ID NO:38—nucleotide sequence encoding SEQ ID NO:37 (FIG. 11)

SEQ ID NO:39—amino acid sequence of fusion protein of CLYTA-MAGE3-Histidine (FIG. 12)

SEQ ID NO:40—nucleotide sequence encoding CLYTA-MAGE3-histidine fusion protein (FIG. 13)

SEQ ID NO:41—MAGE 1 fragment (FIG. 14)
SEQ ID NO:42—MAGE 2 fragment (FIG. 14)
SEQ ID NO:43—MAGE 4a fragment (FIG. 14)
SEQ ID NO:44—MAGE 7 fragment (FIG. 14)
SEQ ID NO:45—MAGE 8 fragment (FIG. 14)
SEQ ID NO:46—MAGE 10 fragment (FIG. 14)
SEQ ID NO:47—MAGE 11 fragment (FIG. 14)
SEQ ID NO:48—MAGE 12 fragment (FIG. 14)
SEQ ID NO:49—MAGE-A6 fragment (FIG. 14)
SEQ ID NO:50—MAGE-A3 fragment (FIG. 14)
SEQ ID NO:51—MAGE-A3 fragment (FIG. 15)
SEQ ID NO:52—MAGE-A6 fragment (FIG. 15)
SEQ ID NO:53—MAGE-A3 synthetic probe sequence MAGEA3F-646MOD (Table 7)

SEQ ID NO:54—MAGEA3F-646MOD probe sequence having unmodified nucleotides

SEQ ID NO:55—β-actin primer sequence RGI BACT F2 (Table 8)

SEQ ID NO:56—β-actin primer sequence RGI BACT R2 (Table 8)

SEQ ID NO:57—β-actin probe sequence HW RGIBACT H (Table 8)

SUMMARY OF THE INVENTION

The present inventors have developed an assay to identify patients having MAGE-A3 expressing tumour tissue who would therefore benefit from MAGE-A3 specific immunotherapy.

In one embodiment of the present invention there is provided a primer comprising the nucleotide sequence of any of SEQ ID NO. 3-12. In a further embodiment, there is provided a set of primers comprising one or more of the following pairs of primers:

a) SEQ ID NO: 3 and 4;
b) SEQ ID NO: 5 and 6;
c) SEQ ID NO: 7 and 8;
d) SEQ ID NO: 9 and 10; and
e) SEQ ID NO: 11 and 12.

In a further aspect of the present invention there is provided a probe comprising the nucleotide sequence of any of SEQ ID NO: 13 to 17, 53 or 54.

In a further embodiment, there is provided a kit comprising:
(i) a forward primer;
(ii) a reverse primer; and
(iii) a probe,
in which components (i), (ii) and (iii) are capable of hybridising to a target sequence of MAGE-A3 under stringent conditions, and in which at least one of the target sequences of (i), (ii) or (iii) differs by at least one nucleotide compared to the equivalent region of all other MAGE A nucleotide sequences and in which the set is capable of being used to discriminate between MAGE-A3 and MAGE-A6.

Additionally, there is provided a kit comprising:
(i) a forward primer;
(ii) a reverse primer; and
(iii) a probe,
in which components (i), (ii) and (iii) are capable of hybridising to a target sequence of MAGE-A3 under stringent conditions, and in which at least one of the target sequences of (i), (ii) or (iii) differs by at least one nucleotide compared to the equivalent region of the MAGE-A6 nucleotide sequence and in which the set is capable of being used to discriminate between MAGE-A3 and MAGE-A6.

In one embodiment, a kit of the present invention may comprise the following components: (i) at least one primer or set of primers as described herein; and (iii) at least one probe as described herein. In one example, component (i) comprises SEQ ID NO: 3 and 4; and component (ii) comprises SEQ ID NO:13; alternatively, component (i) comprises SEQ ID NO: 5 and 6; and component (ii) comprises SEQ ID NO:14; or component (i) comprises SEQ ID NO: 7 and 8; and component (ii) comprises SEQ ID NO:15; or component (i) comprises SEQ ID NO: 9 and 10; and component (ii) comprises SEQ ID NO:16; or component (i) comprises SEQ ID NO: 11 and 12; and component (ii) comprises SEQ ID NO:17; or component (i) comprises SEQ ID NO: 11 and 12; and component (ii) comprises SEQ ID NO:53 or SEQ ID NO:54.

In a further embodiment of the present invention there is provided a method for determining the presence or absence of MAGE-A3 positive tumour tissue, comprising the step of contacting an isolated nucleotide sequence obtained or derived from a biological sample with at least one primer as described herein, set of primers as described herein, probe as described herein or kit as described herein.

Another aspect of the present invention is a method for determining the presence or absence of MAGE-A3 positive tumour tissue, by assaying a biological sample with a primer, probe, or set of primers as described herein.

In a further aspect there is provided a method of patient diagnosis comprising the step of contacting an isolated nucleotide sequence obtained or derived from a biological sample with at least one primer as described herein, set of primers as described herein, probe as described herein or kit as described herein and assessing whether MAGE-A3 is expressed in the sample.

The method may further comprise the step of amplifying a nucleotide sequence and detecting in the sample the amplified nucleotide sequence.

In a yet further aspect there is provided a method for determining the presence or absence of MAGE-A3 positive tumour tissue, comprising contacting an isolated nucleotide sequence obtained or derived from a biological sample with at least one primer or probe as described herein. The method may further comprise the step of determining whether the isolated nucleotide sequence hybridises to the at least one primer or probe under stringent conditions, thereby detecting whether the tumour tissue is MAGE-A3 positive. In one embodiment, the method may further comprise the step of using in situ hybridisation to detect whether the nucleotide sequence hybridises to the at least one primer or probe.

The methods as described herein may be used on a biological sample which is frozen tissue; alternatively or additionally, the methods described herein may be performed on a biological sample which is paraffin-preserved tissue, for example Formalin-Fixed, Paraffin-Embedded tissue (FFPE).

The present invention further provides a method of treating a patient comprising: determining whether a patient's tumour tissue expresses MAGE-A3 using a method as described herein and then administering a composition comprising a MAGE-A3 immunotherapy or immunotherapeutic as described herein to the patient.

In a further embodiment there is provided a method of treating a patient susceptible to recurrence of a MAGE-A3 expressing tumour, the patient having been treated to remove/treat MAGE-A3 expressing tumour tissue, the method comprising: determining whether the patient's tumour tissue expresses MAGE-A3 using a method as described herein and then administering a composition comprising a MAGE-A3 immunotherapy or immunotherapeutic as described herein to said patient.

In a further embodiment of the present invention there is provided a use of a composition comprising a MAGE-A3 immunotherapy or immunotherapeutic in the manufacture of a medicament for the treatment of a patient suffering from a MAGE-A3 expressing tumour, in which a patient is identified as having MAGE-A3 expressing tumour tissue using a method as described herein.

In a yet further embodiment there is provided a use of a composition comprising a MAGE-A3 immunotherapy or immunotherapeutic in the manufacture of a medicament for the treatment of a patient susceptible to recurrence of a MAGE-A3 expressing tumour, in which a patient is identified as having MAGE-A3 expressing tumour tissue using a method as described herein.

In one embodiment there is provided a method of treatment or use as described herein, in which the composition comprising a MAGE-A3 immunotherapy or immunotherapeutic comprises a MAGE-A3 antigen or peptide thereof. In one embodiment the MAGE-A3 antigen or peptide thereof comprises or consists of the peptide EVDPIGHLY.

The MAGE-A3 antigen or peptide for use in the present invention may be fused or conjugated to a carrier protein. In one embodiment, the carrier protein may be selected from protein D, NS1 or CLytA or fragments thereof.

In one embodiment of the present invention the composition comprising a MAGE-A3 immunotherapy or immunotherapeutic may further comprise an adjuvant. For example, the adjuvant may comprise one or more or combinations of: 3D-MPL; aluminium salts; CpG containing oligonucleotides; saponin-containing adjuvants such as QS21 or ISCOMs; oil-in-water emulsions; and liposomes. In one embodiment, the adjuvant may comprise 3D-MPL, CpG containing oligonucleotides and QS21.

DETAILED DESCRIPTION

As used herein, the term 'target sequence' is a region of the MAGE-A3 nucleic acid sequence (either DNA or RNA, e.g. genomic DNA, messenger RNA, or amplified versions thereof) to which the sequence of the probe or primer has partial (i.e. with some degree of mismatch) or total identity; although the reverse primer is the reverse compliment (or, as above, has some degree of mismatch) of the sequence it recognises. The target sequence generally refers to a region of the MAGE-A3 sequence that differs by at least one nucleotide compared to another, or to all other, MAGE-A nucleotide sequences. However, in some embodiments of the present invention the target sequence may, for one or more of the primers and probe, be identical between MAGE-A nucleotide sequences, provided that at least one or two of the primers and probe to be used recognise a target sequence that differs between the genes to be differentiated.

Therefore, in one embodiment, a specific primer or probe would bind the target MAGE-A3 sequence with no mismatches and bind the equivalent region of a further MAGE-A sequence, for example the sequence of MAGE-6, with mismatches of one or more base pairs.

The target sequence for the primers or probe of the present invention may be the sequence having the most differences (mismatches) between the two genes, to enable detection of MAGE-A3 with very high specificity.

In one embodiment of the present invention, the target sequences are in the regions identified in boxed text in FIG. 15.

Suitably, the primer or probe may be at least 95% identical to the target sequence over the length of the primer or probe, suitably greater than 95% identical such as 96%, 97%, 98%, 99% and most preferably has 100% identity over its length to the target MAGE-A3 sequence. The primers or probes of the invention may be identical to the target sequence at all nucleotide positions of the primer or probe, or may have 1, 2, or more mismatches depending upon the length of probe, temperature, reaction conditions and requirements of the assay, for example. Provided, of course, that the reverse primer fulfils these conditions to the region that is the reverse compliment of the primer sequence.

Suitably each nucleotide of the primer or probe can form a hydrogen bond with its counterpart target nucleotide.

Preferably the complementarity of primer or probe with the target sequence is assessed by the degree of A:T and C:G base pairing, such that an adenine (A) nucleotide pairs with a thymine (T), and such that a guanine (G) nucleotide pairs with a cytosine (C), or vice versa. In the RNA form, T may be replaced by U (uracil).

Where inosine is used in universal probes, for example, then complementarity may also be assessed by the degree of inosine (probe)-target nucleotide interactions.

Accordingly, the present invention provides a primer comprising the nucleotide sequence of any of SEQ ID NO. 1-12, as shown in Tables 1 and 2. The term "primer" is used herein to mean any single-stranded oligonucleotide sequence capable of being used as a primer in, for example, PCR technology. Thus, a 'primer' according to the invention refers to a single-stranded oligonucleotide sequence that is capable of acting as a point of initiation for synthesis of a primer extension product that is substantially identical (for a forward primer) or substantially the reverse compliment (for a reverse primer) to the nucleic acid strand to be copied. The design (length and specific sequence) of the primer will depend on the nature of the DNA and/or RNA targets and on the conditions at which the primer is used (such as temperature and ionic strength).

The primers may consist of the nucleotide sequences shown in SEQ ID NO: 1-12, or may be 10, 15, 20, 25, 30, 35, 40, 45, 50, 75, 100 or more base pairs which comprise or fall within the sequences of SEQ ID NO: 1-12, provided they are suitable for specifically binding a target sequence within a MAGE-A3 nucleotide sequence, under stringent conditions. When needed, slight modifications of the primers of probes in length or in sequence can be carried out to maintain the specificity and sensitivity required under the given circumstances. Probes and/or primers listed herein may be extended or reduced in length by 1, 2, 3, 4 or 5 nucleotides, for example, in either direction.

As used herein, the term "stringent conditions" means any hybridisation conditions which allow the primers to bind specifically to a nucleotide sequence within the MAGE-A3 nucleotide sequence, but not to any other MAGE nucleotide sequences. 'Specific binding" or "specific hybridisation' of a probe to a region of the MAGE-A3 nucleotide sequence means that the primer or probe forms a duplex (double-stranded nucleotide sequence) with part of this region or with the entire region under the experimental conditions used, and that under those conditions the primer or probe does not form a duplex with other regions of the nucleotide sequence present in the sample to be analysed. It should be understood that the primers and probes of the present invention that are designed for specific hybridisation within a region of the MAGE-A3 nucleotide sequence may fall entirely within said region or may to a large extent overlap with said region (i.e. form a duplex with nucleotides outside as well as within said region).

Suitably, the specific hybridisation of a probe to a nucleic acid target region occurs under "stringent" hybridisation conditions, such as 3×SSC, 0.1% SDS, at 50° C. The skilled person knows how to vary the parameters of temperature, probe length and salt concentration such that specific hybridisation can be achieved. Hybridisation and wash conditions are well known and exemplified in, for example, Sambrook, et al., Molecular Cloning: A Laboratory Manual, Second Edition, Cold Spring Harbor, N.Y., (1989), particularly Chapter 11 therein.

The present invention further provides a set of primers comprising one or more of the following pairs of primers:

Set 1: SEQ ID NO: 3 and 4
Set 2: SEQ ID NO: 5 and 6
Set 3: SEQ ID NO: 7 and 8
Set 4: SEQ ID NO: 9 and 10
Set 5: SEQ ID NO: 11 and 12

The present invention further provides a probe comprising the nucleotide sequence of any of SEQ ID NO: 13-17, 53 or 54. The term "probe" is used herein to mean any single-stranded oligonucleotide sequence capable of binding nucleic acid and being used as a probe in, for example, PCR technology: The probes may consist of the nucleotide sequences shown in SEQ ID NO:13-17, 53 or 54 or may be 5, 6, 7, 8, 9, 10, 11, 12, 13, 14, 15, 16, 17, 18, 19 or 20, 25, 30, 35, 40, 45, 50, 75, 100 or more base pairs which comprise or fall within the sequences of SEQ ID NO:13-17, 53 or 54 provided they are suitable for specifically binding a target sequence within a MAGE-A3 nucleotide sequence.

In one embodiment of the invention, in which a probe is to be used in a method in combination with a pair of primers, the pair of primers should allow for the amplification of part or all of the MAGE-A3 polynucleotide fragment to which probes are able to bind or to which the probes are immobilised on a solid support.

The primer and/or probe may additionally comprise a marker, enabling the probe to be detected. Examples of markers that may be used include: fluorescent markers, for example, 6-carboxyfluorescein (6FAM™), NED™ (Applera Corporation), HEX™ or VIC™ (Applied Biosystems); TAMRA™ markers (Applied Biosystems, CA, USA); chemiluminescent markers, for example Ruthenium probes; and radioactive labels, for example tritium in the form of tritiated thymidine. $^{32}$-Phosphorus may also be used as a radiolabel.

In one embodiment of the present invention, the probe may comprise a fluorescent reporter dye at its 5'-end and a quencher dye at its 3'-end. The fluorescent reporter dye may comprise 6-carboxyfluorescein (6FAM) and the quencher dye may comprise a non-fluorescent quencher (NFQ). Optionally, a Minor Groove Binder protein (MGB™; Applied Biosystems, CA, USA) may be added to the probe, for example the 3' end of the probe.

In one embodiment, an MGB™ Eclipse Probe may be used (Epoch Biosciences, WA, USA). MGB™ Eclipse probes have an Eclipse™ Dark Quencher and an MGB™ moiety positioned at the 5'-end of the probe. A fluorescent reporter dye is located on the 3'-end of the probe.

In one embodiment, the primer and probe sequences of the present invention may contain or comprise naturally occurring nucleotide structures or bases, for example adenine (A), cytosine (C), guanine (G), thymine (T) and uracil (U).

In a further embodiment, synthetic or modified analogues of nucleotide structures or bases may be included in the sequence of the probe. By synthetic or modified is meant a non-naturally occurring nucleotide structure or base. Such synthetic or modified bases may replace 1, 2, 3, 4, 5, 6, 7, 8, 9 or all of the bases in the probe sequence. In one embodiment, Cytosine may be replaced by 5-Methyl dC and Thymine may be replaced by 5-Propynyl dU. BHQ2 Quencher may also be included within the sequence.

The present invention additionally provides a kit comprising the following components: (i) at least one primer or set of primers as described herein; and (ii) at least one probe as described herein. In one embodiment, the kit comprises one forward primer, one reverse primer and a probe sequence which has a target sequence within the region amplified by the forward and reverse primers. In this embodiment, the set of primers are capable of amplifying a portion (amplicon) of the sequence of MAGE-A3 and the probe is capable of hybridising under stringent conditions to the amplicon.

The sequences of MAGE-A3 and MAGE-A6 are highly homologous, having 98% alignment of their nucleotide and 95% alignment of their protein sequences. In order to specifically identify MAGE-A3 sequences, it is necessary to identify primers and probes capable of differentiating between MAGE-A3 and MAGE-A6.

In one embodiment, the present invention provides a set of primers and/or probes which specifically hybridise to a target sequence of MAGE-A3 under stringent conditions in which at least one of the target sequences of the primer or probe differs by at least one nucleotide compared to the equivalent region of all other MAGE A nucleotide sequences and in which the set is capable of discriminating between MAGE-A3 and MAGE-A6.

In one embodiment, the present invention provides a set of primers and/or probes which specifically hybridise to a target sequence of MAGE-A3 under stringent conditions in which at least one of the target sequences of the primer or probe differs by at least one nucleotide compared to the equivalent region of the MAGE A6 nucleotide sequence and in which the set is capable of discriminating between MAGE-A3 and MAGE-A6.

In one embodiment, the target sequence of at least one primer or probe may differ by one nucleotide in the target sequence of MAGE-A3, compared to the equivalent region of MAGE-A6. In a further embodiment, the target sequence of at least one primer or probe may differ by two nucleotides compared to the equivalent region of MAGE-A6.

In one embodiment, a kit comprising two primers and one probe may have the following differences in the target sequences of the primers and probe:
(i) the target sequence of one of the two primers or the probes differs by one nucleotide between MAGE-A3 and MAGE-A6;
(ii) the target sequence of a primers or probe not referred to in part (i), differs by one nucleotide between MAGE-A3 and MAGE-A6; and
(iii) the target sequence of the remaining primer or probe is identical for both MAGE-A3 and MAGE-A6;

For example, in one embodiment, a kit comprising primer A, primer B and probe C may comprise the following differences in the target sequences:
(i) the target sequence of primer A differs by one nucleotide between MAGE-A3 and MAGE-A6;
(ii) the target sequence of primer B differs by two nucleotides between MAGE-A3 and MAGE-A6; and
(iii) the target sequence of probe C is identical for both MAGE-A3 and MAGE-A6.

For example, in one embodiment, a kit comprising primer A, primer B and probe C may comprise the following differences in the target sequences:
(i) the target sequence of primer A differs by two nucleotides between MAGE-A3 and MAGE-A6;
(ii) the target sequence of primer B is identical for both MAGE-A3 and MAGE-A6; and
(iii) the target sequence of probe C differs by one nucleotides between MAGE-A3 and MAGE-A6;

For example, in one embodiment, a kit comprising primer A, primer B and probe C may comprise the following differences in the target sequences:
(i) the target sequence of primer A is identical for both MAGE-A3 and MAGE-A6;
(ii) the target sequence of primer B differs by one nucleotide between MAGE-A3 and MAGE-A6; and
(iii) the target sequence of probe C differs by two nucleotides between MAGE-A3 and MAGE-A6;

In one embodiment, the kit may comprise: the pair of primers of or comprising SEQ ID NO: 3 and 4 and the probe of or comprising SEQ ID NO:13; the pair of primers of or comprising SEQ ID NO: 5 and 6 and the probe of or comprising SEQ ID NO:14; the pair of primers of or comprising SEQ ID NO: 7 and 8 and the probe of or comprising SEQ ID NO:15; the pair of primers of or comprising SEQ ID NO: 9 and 10 and the probe of or comprising SEQ ID NO:16; and/or the pair of primers of or comprising SEQ ID NO: 11 and 12 and the probe of or comprising SEQ ID NO:17.

In a further embodiment of the present invention there is provided a method for determining the presence or absence of MAGE-A3 positive tumour tissue, comprising the step of contacting a nucleotide sequence obtained or derived from a biological sample with at least one primer or at least one set of primers or probe as described herein. By MAGE-A3 positive tumour tissue is meant any tumours or tumour cells expressing the MAGE-A3 antigen that have been isolated from a patient. The method as described herein may be used to determine whether a biological sample comprises or consists of MAGE-A3 positive tumour tissue.

By biological sample is meant a sample of tissue or cells from a patient that has been removed or isolated from the patient.

There is additionally provided a method of patient diagnosis comprising the step of contacting a nucleotide sequence obtained or derived from a biological sample with at least one primer or at least one set of primers or probe as described herein and assessing whether MAGE-A3 is expressed in the sample.

In one embodiment, the nucleotide sequence is or has been isolated from the biological sample.

The term "obtained or derived from" as used herein is meant to be used inclusively. That is, it is intended to encompass any nucleotide sequence directly isolated from a tumour sample or any nucleotide sequence derived from the sample for example by use of reverse transcription to produce mRNA or cDNA.

A method of the present invention may further comprise amplifying the nucleotide sequence and detecting in the sample the amplified nucleotide sequence. Alternatively or additionally, the method of the present invention may further comprise contacting the isolated or amplified nucleotide sequence with one or more probes as described herein.

In one embodiment, the nucleotide sequence is isolated or purified from the tumour sample. In RT-PCR, genomic DNA contamination may lead to false positive results. In one embodiment, the genomic DNA is removed or substantially removed from the sample to be tested or included in the methods of the present invention.

The methods of the present invention are suitable for detecting MAGE-A3 positive tumour tissue. In one embodiment of the present invention, MAGE-A3 positive tissue may be detected using in situ hybridisation. By in situ hybridisation is meant is a hybridisation reaction performed using a primer or probe according to the present invention on intact chromosomes, cells or tissues isolated from a patient for direct visualization of morphologic sites of specific DNA or RNA sequences.

Hybridisation of the polynucleotides may be carried out using any suitable hybridisation method and detection system. Examples of hybridisation systems include conventional dot blot, Southern blots, and sandwich methods. For example, a suitable method may include a reverse hybridisation approach, wherein type-specific probes are immobilised on a solid support in known distinct locations (dots, lines or other figures), and amplified polynucleic acids are labelled in order to detect hybrid formation. The MAGE-A3 specific nucleic acid sequences, for example a probe or primer as described herein, can be labelled with biotin and the hybrid can be detected via a biotin-streptavidin coupling with a non-radioactive colour developing system. However, other reverse hybridisation systems may also be employed, for example, as illustrated in Gravitt et al, (Journal of Clinical Microbiology, 1998, 36(10): 3020-3027) the contents of which are also incorporated by reference. Standard hybridisation and wash conditions are described in Kleter et al., Journal of Clinical Microbiology, 1999, 37(8): 2508-2517 and will be optimised under the given circumstances to maintain the specificity and the sensitivity required by the length and sequence of the probe(s) and primer(s).

In one embodiment, the method of the present invention may comprise use of:
a) the pair of primers comprising SEQ ID NO: 3 and 4; and a probe comprising SEQ ID NO:13;
b) the pair of primers comprising SEQ ID NO: 3 and 4; and a probe comprising SEQ ID NO:17
c) the pair of primers comprising SEQ ID NO: 3 and 4; and a probe comprising SEQ ID NO:53
d) the pair of primers comprising SEQ ID NO: 3 and 4; and a probe comprising SEQ ID NO:54
e) the pair of primers comprising SEQ ID NO: 5 and 6 and the probe comprising SEQ ID NO:14;
f) the pair of primers comprising SEQ ID NO: 7 and 8 and the probe comprising SEQ ID NO:15;
g) the pair of primers comprising SEQ ID NO: 9 and 10 and the probe comprising SEQ ID NO:16;
h) the pair of primers comprising SEQ ID NO: 11 and 12 and the probe comprising SEQ ID NO:17;
i) the pair of primers comprising SEQ ID NO: 11 and 12; and a probe comprising SEQ ID NO:53; and/or
j) the pair of primers comprising SEQ ID NO: 11 and 12; and a probe comprising SEQ ID NO:54

The methods as described herein are suitable for use in fresh tissue, frozen tissue, paraffin-preserved tissue and/or ethanol preserved tissue. Well-known extraction and purification procedures are available for the isolation of RNA or DNA from a sample (e.g. in Sambrook et al., 1989). The RNA or DNA may be used directly following extraction from the sample or, more preferably, after a polynucleotide amplification step (e.g. PCR) step. In specific instances, such as for reverse hybridisation assays, it may be necessary to reverse transcribe RNA into cDNA before amplification. In both latter cases the amplified polynucleotide is 'derived' from the sample.

In one embodiment, in which the sample is paraffin-preserved tissue, the following sets of primers and probes may be used:
a) the pair of primers comprising SEQ ID NO: 7 and 8 and the probe comprising SEQ ID NO:15;
b) the pair of primers comprising SEQ ID NO: 9 and 10 and the probe comprising SEQ ID NO:16;
c) the pair of primers comprising SEQ ID NO: 11 and 12 and the probe comprising SEQ ID NO:17;
d) the pair of primers comprising SEQ ID NO: 11 and 12; and a probe comprising SEQ ID NO:53; and/or
e) the pair of primers comprising SEQ ID NO: 11 and 12; and a probe comprising SEQ ID NO:54

The present invention additionally provides a method of treating a patient comprising: determining whether the patient's tumour tissue expresses MAGE-A3 using a method as described herein, and administering a composition comprising a MAGE-A3 antigen, epitope or antigen derivative or a MAGE-A3 specific antibody or immunoglobulin to said patient. The patient may have tumour tissue expressing MAGE-A3 (active disease setting), or may be susceptible to recurrence of a MAGE-A3 expressing tumour, the patient having been treated to remove/treat MAGE-A3 expressing tumour tissue (adjuvant setting).

The present invention further provides the use of a composition comprising a MAGE-A3 antigen, epitope or antigen derivative or a MAGE-A3 specific antibody or immunoglobulin in the manufacture of a medicament for the treatment of a patient suffering from a MAGE-A3 expressing tumour or susceptible to recurrence of a MAGE-A3 expressing tumour, in which a patient is identified as having or identified as having had MAGE-A3 expressing tumour tissue using a diagnostic method, kit, primer or probe as described herein.

The composition comprising a MAGE-A3 antigen, epitope or antigen derivative may comprise a MAGE-A3 antigen or peptide thereof. In one embodiment, the MAGE-A3 antigen or peptide thereof comprises or consists of the peptide EVDPIGHLY. The MAGE-A3 antigen or peptide may be fused or conjugated to a carrier protein, which may be selected from protein D, NS1 or CLytA or fragments thereof.

In one embodiment, the composition may further comprise an adjuvant; for example an adjuvant comprising one or more or a combination of: 3D-MPL; aluminium salts; CpG containing oligonucleotides; saponin-containing adjuvants such as QS21 or ISCOMs; oil-in-water emulsions; and liposomes.

Thus the present invention provides a method for screening, in clinical applications, tissue samples from a human patient for the presence or absence of the expression of MAGE-A3. Such samples could consist of, for example, needle biopsy cores, surgical resection samples or lymph node tissue. For example, these methods include obtaining a biopsy, which is optionally fractionated by crypstat sectioning to enrich tumour cells to about 80% of the total cell population. In certain embodiments, nucleic acids may be extracted from these samples using techniques well known in the art. In other embodiments nucleic acids extracted from the tissue sample may be amplified using techniques well known in the art. The level of MAGE-A3 expression can be detected and can be compared with statistically valid groups and/or controls of MAGE-A3 negative patients.

In one embodiment, the diagnostic method comprises determining whether a subject expresses the MAGE-A3 gene product, for example by detecting the corresponding mRNA and/or protein level of the gene product. For example by using techniques such as Northern blot analysis, reverse transcription-polymerase chain reaction (RT-PCR), semi-quantitative RT-PCR, quantitative RT-PCR, TaqMan PCR, in situ hybridisation, immunoprecipitation, Western blot analysis or immunohistochemistry. According to such a method, cells or tissue may be obtained from a subject and the level of mRNA and/or protein compared to those of tissue not expressing MAGE-A3.

TaqMan PCR Technology

Taq DNA polymerase has 5'-3' exonuclease activity. The Taqman PCR assay uses this exonuclease activity to cleave dual-labelled probes annealed to target sequences during PCR amplification.

Briefly, RNA is extracted from a sample and cDNA is synthesised (reverse transcription). The cDNA is then added to a PCR reaction mixture containing standard PCR components (see, for example, components supplied by Roche (CA, USA) for Taqman PCR. The reaction mixture additionally contains a probe that anneals to the template nucleotide sequence between the two primers (ie within the sequence amplified by the PCR reaction, the "amplicon"). The probe comprises a fluorescent reporter dye at the 5'-end and a quencher dye at the 3'-end. The quencher is able to quench the reporter fluorescence, but only when the two dyes are close to each other: this occurs for intact probes.

During and after amplification, the probe is degraded by the Taq DNA polymerase, and any fluorescence is detected.

For quantitative measurements, the PCR cycle number at which fluorescence reaches a threshold value of 10 times the standard deviation of baseline emission is used. This cycle number, called the cycle threshold (Ct), is inversely proportional to the starting amount of target cDNA and allows the amount of cDNA to be measured. Essentially, the more target RNA present in a sample, the lower the Ct number obtained.

The measurements obtained for the Ct value are compared to those obtained for a housekeeping gene. This allows for any errors based on the amount of total RNA added to each reverse transcription reaction (based on wavelength absorbance) and its quality (i.e., degradation): neither of which are reliable parameters to measure the starting material. Therefore, transcripts of a housekeeping gene are quantified as an endogenous control. Beta-actin is one of the most used non-specific housekeeping genes, although others may be used.

In yet a further embodiment of the invention, there is provided a method of treating a patient suffering from a MAGE-A3 expressing tumour, the method comprising determining, through use of a method of the present invention, whether the patient expresses the MAGE-A3 protein and subsequently administering a composition comprising a MAGE-A3 antigen, epitope or antigen derivative or a MAGE-A3 specific antibody or immunoglobulin to prevent or ameliorate recurrence of disease. The patient may first receive treatment such as resection by surgery of any tumour or other chemotherapeutic or radiotherapy treatment.

Thus, the invention further provides the use of MAGE-specific immunotherapy in the manufacture of a medicament for the treatment of patients suffering from MAGE-A3 expressing tumour or patients who have received treatment (surgery, chemotherapy or radiotherapy) to remove or treat a MAGE-A3 expressing tumour, said patient having been determined as having MAGE-A3-expressing tumour tissue; through use of a diagnostic method, kit, primer or probe according to the present invention.

Thus, this invention may be used for patients having MAGE-A3 expressing cancers, such as: melanoma; breast cancer; bladder cancer including transitional cell carcinoma; lung cancer including non-small cell lung carcinoma (NSCLC); head and neck cancer including oesophagus carcinoma; squamous cell carcinoma; liver cancer; multiple myeloma and colon carcinoma. In an embodiment, the invention may be used in the treatment of patients in an adjuvant (post-operative) setting in such cancers particularly lung and melanoma. The invention also finds utility in the treatment of metastatic cancers.

Immunotherapy

Compositions suitable for use in methods for treating patients of the present invention are those capable of raising a MAGE-A3 specific immune response. The composition will contain at least one epitope from a MAGE-A3 gene product. Such an epitope may be present as a peptide antigen optionally linked covalently to a carrier. Alternatively, larger protein fragments may be used. The fragments and peptides for use must however, when suitably presented be capable of raising an immune response against MAGE-A3, for example a MAGE-A3-specific immune response.

Examples of peptides that may be used in the present invention include the following MAGE-A3 peptides:

| SEQ ID NO | Peptide sequence |
|---|---|
| SEQ ID NO: 23 | FLWGPRALV |
| SEQ ID NO: 24 | MEVDPIGHLY |
| SEQ ID NO: 25 | VHFLLLKYRA |
| SEQ ID NO: 26 | LVHFLLLKYR |
| SEQ ID NO: 27 | LKYRAREPVT |
| SEQ ED NO: 28 | ACYEFLWGPRALVETS |
| SEQ ID NO: 29 | TQHFVQENYLEY |

In one embodiment, the antigen may comprise a MAGE peptide or protein linked to an immunological fusion or expression enhancer partner. The MAGE protein may be full length MAGE-A3 or may comprise a fragment of MAGE3, for example amino acids 3-314 of MAGE3 (312 amino acids in total).

The antigen and partner may be chemically conjugated, or may be expressed as a recombinant fusion protein. In an embodiment in which the antigen and partner are expressed as a recombinant fusion protein, this may allow increased levels to be produced in an expression system compared to non-fused protein. Thus the fusion partner may assist in providing T helper epitopes (immunological fusion partner), preferably T helper epitopes recognised by humans, and/or assist in expressing the protein (expression enhancer) at higher yields than the native recombinant protein. In one embodiment, the fusion partner may be both an immunological fusion partner and expression enhancing partner.

In one embodiment of the invention, the immunological fusion partner that may be used is derived from protein D, a surface protein of the gram-negative bacterium, *Haemophilus influenza* B (WO91/18926) or a derivative thereof. The protein D derivative may comprise the first ⅓ of the protein, or approximately the first ⅓ of the protein. In one embodiment, the first 109 residues of protein D may be used as a fusion partner to provide a MAGE-A3 antigen with additional exogenous T-cell epitopes and increase expression level in *E. coli* (thus acting also as an expression enhancer). In an alternative embodiment, the protein D derivative may comprise the first N-terminal 100-110 amino acids or approximately the first N-terminal 100-110 amino acids. In one embodiment, the protein D or derivative thereof may be lipidated and lipoprotein D may be used: the lipid tail may ensure optimal presentation of the antigen to antigen presenting cells In one embodiment, the MAGE-A3 may be Protein D-MAGE-A3/His, a 432-amino-acid-residue fusion protein. This fusion protein comprises amino acids 1 to 109 of Protein D, a lipoprotein present on the surface of the gram-negative bacterium *Haemophilus Influenzae* B, 312 amino acids from the MAGE-A3 protein (amino acids 3-314), a spacer and a polyhistidine tail (His) that may facilitate the purification of the fusion protein during the production process, for example:
i) An 18-residue signal sequence and the first 109 residues of the processed protein D, the signal sequence being cleaved from the fusion protein during production to leave the first 109 residues;
ii) Two unrelated residues (methionine and aspartic acid);
iii) Residues 3-314 of the native MAGE-3 protein;
iv) Two glycine residues functioning as a hinge region
v) seven Histidine residues;

In an alternative embodiment, the above construct may be used except (i) may be replaced with a sequence comprising the first N-terminal 100-110 amino acids or approximately the first N-terminal 100-110 amino acids of Protein D.

MAGE-3 may be expressed as a fusion protein with protein D at the N terminus and a sequence of seven histidine residues (His tail) at the C-terminus. Protein D is a 42-kDa immunoglobulin-D binding protein, exposed on the surface of the Gram-negative bacterium *Haemophilus Influenzae* B.

In another embodiment the immunological fusion partner protein D may be replaced with the protein known as LytA. LytA is derived from *Streptococcus pneumoniae* which synthesise an N-acetyl-L-alanine amidase, amidase LytA, (coded by the LytA gene (Gene, 43 (1986) page 265-272)) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described (Biotechnology: 10, (1992) page 795-798). In one embodiment, the C terminal portion of the molecule may be used. The embodiment may utilise the repeat portion of the LytA molecule found in the C terminal end starting at residue 178. In one embodiment, the LytA portion may incorporate residues 188-305.

In one embodiment of the present invention, the MAGE-A3 protein may comprise a derivatised free thiol. Such antigens have been described in WO99/40188. In particular carboxyamidated or carboxymethylated derivatives may be used.

In one embodiment of the present invention, the tumour associated antigen comprises a MAGE-A3-Protein D molecule. The nucleotide and amino acid sequences for this molecule are shown in FIG. 9 (SEQ ID NO:35 and SEQ ID NO:36). This antigen and those summarised below are described in more detail in WO99/40188.

In further embodiments of the present invention, the tumour associated antigen may comprise any of the following fusion proteins:

A fusion protein of NS1-MAGE3, and Histidine tail, for example as shown in FIGS. 10 and 11 (SEQ ID NO:37 and SEQ ID NO:38); A fusion protein of CLYTA-MAGE3-Histidine, for example as shown in FIGS. 12 and 13 (SEQ ID NO:39 and SEQ ID NO:40).

A further embodiment of the present invention comprises utilising a nucleic acid immunotherapeutic which comprises a nucleic acid molecule encoding a MAGE-A3 specific tumour associated antigen as described herein. In one embodiment of the present invention, the sequences may be inserted into a suitable expression vector and used for DNA/RNA vaccination. Microbial vectors expressing the nucleic acid may also be used as vectored delivered immunotherapeutics.

Examples of suitable viral vectors include retroviral, lentiviral, adenoviral, adeno-associated viral, herpes viral including herpes simplex viral, alpha-viral, pox viral such as Canarypox and vaccinia-viral based systems. Gene transfer techniques using these viruses are known to those skilled in the art. Retrovirus vectors for example may be used to stably integrate the polynucleotide of the invention into the host genome, although such recombination is not preferred. Replication-defective adenovirus vectors by contrast remain episomal and therefore allow transient expression. Vectors capable of driving expression in insect cells (for example baculovirus vectors), in human cells, yeast or in bacteria may be employed in order to produce quantities of the MAGE-A3 protein encoded by the polynucleotides of the present invention, for example for use as subunit vaccines or in immunoassays.

In a preferred embodiment the adenovirus used as a live vector is a replication defective simian adenovirus. Typically these viruses contain an E1 deletion and can be grown on cell lines that are transformed with an E1 gene. Preferred Simian adenoviruses are viruses isolated from Chimpanzee. In particular C68 (also known as Pan 9) (See U.S. Pat. No. 6,083, 716) and Pan 5, 6 and Pan 7 (WO 03/046124) are preferred for use in the present invention. Thus these vectors can be manipulated to insert a heterologous gene of the invention such that the gene product maybe expressed. The use, formulation and manufacture of such recombinant adenoviral vectors is set forth in detail in WO 03/046142.

Conventional recombinant techniques for obtaining nucleic acid sequences, and production of expression vectors of are described in Maniatis et al., Molecular Cloning—A Laboratory Manual; Cold Spring Harbor, 1982-1989.

For protein based immunotherapeutics the proteins of the present invention are provided either soluble in a liquid form or in a lyophilised form.

Each human dose may comprise 1 to 1000 µg of protein. In one embodiment, the dose may comprise 30-300 µg of protein.

The immunotherapeutic as described herein may further comprise a vaccine adjuvant, and/or an immunostimulatory cytokine or chemokine.

Suitable vaccine adjuvants for use in the present invention are commercially available such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatised polysaccharides; polyphosphazenes; biodegradable microspheres; monophosphoryl lipid A and quil A. Cytokines, such as GM-CSF or interleukin-2, -7, or -12, and chemokines may also be used as adjuvants.

In formulations of the invention it may be desirable that the adjuvant composition induces an immune response predominantly of the Th1 type. High levels of Th1-type cytokines (e.g., IFN-γ, TNFα, IL-2 and IL-12) tend to favour the induction of cell mediated immune responses to an administered antigen. According to one embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

Accordingly, suitable adjuvants that may be used to elicit a predominantly Th1-type response include, for example a combination of monophosphoryl lipid A, such as 3-de-O-acylated monophosphoryl lipid A (3D-MPL) together with an aluminium salt. 3D-MPL or other toll like receptor 4 (TLR4) ligands such as aminoalkyl glucosaminide phosphates as disclosed in WO9850399, WO0134617 and WO03065806 may also be used alone to generate a predominantly Th1-type response.

Other known adjuvants, which may preferentially induce a TH1 type immune response, include TLR9 antagonists such as unmethylated CpG containing oligonucleotides. The oligonucleotides are characterised in that the CpG dinucleotide is unmethylated. Such oligonucleotides are well known and are described in, for example WO 96/02555.

Suitable oligonucleotides include:

| | | |
|---|---|---|
| SEQ ID NO: 30 | TCC ATG ACG TTC CTG ACG TT | CpG 1826 |
| SEQ ID NO: 31 | TCT CCC AGC GTG CGC CAT | CpG 1758 |
| SEQ ID NO: 32 | ACC GAT GAC GTC GCC GGT GAC GGC ACC ACG | |
| SEQ ID NO: 33 | TCG TCG TTT TGT CGT TTT GTC GTT | CpG 2006, CpG 7909 |
| SEQ ID NO: 34 | TCC ATG ACG TTC CTG ATG CT | CpG 1668 |

CpG-containing oligonucleotides may also be used alone or in combination with other adjuvants. For example, an enhanced system involves the combination of a CpG-containing oligonucleotide and a saponin derivative particularly the combination of CpG and QS21 as disclosed in WO00/09159 and WO00/62800.

The formulation may additionally comprise an oil in water emulsion and/or tocopherol.

Another suitable adjuvant is a saponin, for example QS21 (Aquila Biopharmaceuticals Inc., Framingham, Mass.), that may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other suitable formulations comprise an oil-in-water emulsion and tocopherol. A particularly potent adjuvant formulation involving QS21, 3D-MPL and tocopherol in an oil-in-water emulsion is described in WO 95/17210.

In another embodiment, the adjuvants may be formulated in a liposomal composition. The amount of 3 D MPL used is generally small, but depending on the Immunotherapeutic formulation may be in the region of 1-1000 µg per dose, preferably 1-500 µg per dose, and more preferably between 1 to 100 µg per dose.

In an embodiment, the adjuvant system comprises three immunostimulants: a CpG oligonucleotide, 3 D-MPL, & QS21 either presented in a liposomal formulation or an oil in water emulsion such as described in WO 95/17210.

The amount of CpG or immunostimulatory oligonucleotides in the adjuvants or immunotherapeutics of the present invention is generally small, but depending on the immunotherapeutic formulation may be in the region of 1-1000 µg per dose, preferably 1-500 µg per dose, and more preferably between 1 to 100 µg per dose.

The amount of saponin for use in the adjuvants of the present invention may be in the region of 1-1000 µg per dose, preferably 1-500 µg per dose, more preferably 1-250 µg per dose, and most preferably between 1 to 100 µg per dose.

Generally, each human dose may comprise 0.1-1000 µg of antigen, for example 0.1-500 µg, 0.1-100 µg, or 0.1 to 50 µg. An optimal amount for a particular immunotherapeutic can be ascertained by standard studies involving observation of appropriate immune responses in vaccinated subjects. Following an initial vaccination, subjects may receive one or several booster immunisation adequately spaced.

Other suitable adjuvants include Montanide ISA 720 (Seppic, France), SAF (Chiron, Calif., United States), ISCOMS (CSL), MF-59 (Chiron), Ribi Detox, RC-529 (GSK, Hamilton, Mont.) and other aminoalkyl glucosaminide 4-phosphates (AGPs).

Accordingly there is provided an immunogenic composition for use in the method of the present invention comprising an antigen as disclosed herein and an adjuvant, wherein the adjuvant comprises one or more of 3D-MPL, QS21, a CpG oligonucleotide, a polyethylene ether or ester or a combination of two or more of these adjuvants. The antigen within the immunogenic composition may be presented in an oil in water or a water in oil emulsion vehicle or in a liposomal formulation.

In one embodiment, the adjuvant may comprise one or more of 3D-MPL, QS21 and an immunostimulatory CpG oligonucleotide. In an embodiment all three immunostimulants are present. In another embodiment 3D MPL and Qs21 are presented in an oil in water emulsion, and in the absence of a CpG oligonucleotide.

A composition for use in the method of the present invention may comprise a pharmaceutical composition comprising tumour associated antigen as described herein, or a fusion protein, in a pharmaceutically acceptable excipient.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

The invention will be further described by reference to the following, non-limiting, examples, in which RT-PCR refers to reverse-transcription polymerase chain reaction:

EXAMPLES

Example 1

Semi-Quantitative PCR—Frozen Tissue Samples
Primers: SEQ ID NO: 1 and SEQ ID NO:2
RNA Extraction: Liquid Nitrogen RNA Purification Method A small piece of tissue was snap frozen into liquid nitrogen and then placed into a mortar for mechanical grinding by a pestle. 100 mg of the resultant powder was added to 100 ul of TriPure isolation reagent and RNA extracted according to the manufacturer's instructions (Qiagen, Venlo, Netherlands). RNA concentration was determined from the optical density value at 260 nm.

Semi-Quantitative MAGE-A3 RT-PCR

Semi-quantitative RT-PCR was carried out as described by De Plaen et al (Immunogenetics 40:360, 1994). cDNA synthesis from 2 µg of total RNA was performed in a 20 µl mixture containing 1× first strand buffer, 0.5 mM of each dNTP, 10 mM of dithiothreitol, 20 U of rRNase inhibitor, 2 µM of oligo (dT) 15 and 200 U of M-MLV reverse transcriptase for 1 h30 at 42° C. 50 ng of cDNA was amplified by PCR in a 25 µl mixture containing primers specific for MAGE-A3 (SEQ ID NOs 1 and 2). A 10 µl aliquot of each reaction was run on a 1% agarose gel electrophoresis and visualised by ethidium bromide fluorescence. The sizes of the amplicons are 725 bp and 805 bp when mRNA and genomic DNA (gDNA) are respectively amplified.

Positive Controls for Semi-Quantitative MAGE-A3 RT-PCR:

Three positive controls were introduced for these experiments:

(i) A cloned fragment of MAGE-A3 genomic DNA was added to each PCR reaction mixture. This generates a fragment of 805 bp (80 bp greater than the fragment generated from the cDNA) and is always present in the absence of PCR inhibition. This acts as a positive control to check PCR efficiency in MAGE-A3 negative samples;

(ii) For each MAGE-A3 assay, cDNA synthesis was carried out in parallel on tumour samples and on RNA extracted from the "Gerl" melanoma cell-line MZ-2-3.0. To be considered "positive", tumour samples must yield a signal at 1% the level of Gerl cell-line MZ-2-3.0 cDNA (iii) Beta-actin PCR (Table 1) was carried out on each sample in order to detect samples with strongly degraded RNA. If the beta-actin signal generated from a MAGE-A3 negative tumour sample was weaker than the signal generated from the MZ-2-3.0 the number of cycles was adjusted for the clinical sample so that the intensity of beta-actin amplicon reached the required level.

Negative Controls for Semi-Quantitative MAGE-A3 RT-PCR:

Three negative controls were introduced for these experiments:

(i) RNA extracted from cell culture LB 23-1/2, known to be MAGE-A3 negative;
(ii) a water control in RT-reaction; and
(iii) a water control in the PCR steps.

Interpretation of Data

A 50 ng sample of mRNA from a tumour sample was considered MAGE-A3 positive when the amount of 725 bp amplicon was equal to or greater than the amount of amplicon obtained using 0.5 ng of RNA from the Gerl cell-line MZ-2-3.0 RNA (ie. equivalent to 0.1% of Gerl RNA; see positive controls). Amounts were estimated by ethidium bromide fluorescence. Positive and negative controls were added.

Figure 16:
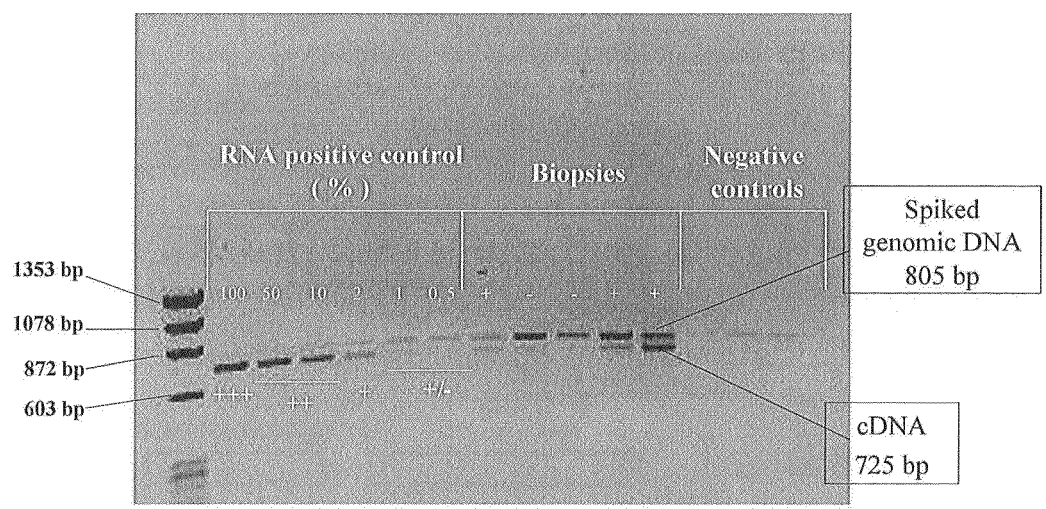
FIG. 16: Classes for Semi-quantitative MAGE-A3 RT-PCR: an example of how five classes may be assigned to the semi-quantitative MAGE-A3 RT-PCR assay

Classes for Semi-quantitative MAGE-A3 RT-PCR: five standard classes (De Plaen et al., 1994) were assigned to the semi-quantitative MAGE-A3 RT-PCR assay. These are a subjective measurement and were, from lowest to highest expression −, −/+, +, ++, +++. An example of how these classes may be assigned is shown in FIG. 16: in this figure, the classes are assigned according to the band generated by the positive control as shown in Table 6, below:

TABLE 6

| | RNA positive control | | | | |
|---|---|---|---|---|---|
| | 100 | 50 | 10 | 2 | 1 | 0.5 |
| Class | +++ | | ++ | | + | +/− |

Example 2

Real Time Taqman Quantitative RT-PCR—Frozen Tissue Samples

Real Time Taqman Quantitative RT-PCR:
Primers: SEQ ID NO: 3 and SEQ ID NO:4; Probe: SEQ ID NO: 13 (exon)
Primers: SEQ ID NO: 5 and SEQ ID NO:6; Probe: SEQ ID NO: 14 (intron)

Semi-Quantitative PCR (for Comparison Studies):
Primers: SEQ ID NO: 1 and SEQ ID NO:2

Materials and Methods

Patients and Sample Collection

Biopsies from stage IB and II Non Small Cell Lung Carcinoma (NSCLC) tumours were obtained by surgery. Patients had enrolled in two clinical trials, the GSK 249553/004 (MAGE3-AS02B-004) and the Epidemio-MAGE3-153; patients had signed the informed consent and were explained the nature and the possible consequences of the studies. Biopsies were immersed in RNA-stabilizing solution (RNA-later, Ambion, Cambridge, UK) directly after surgical resection and stored at −20° C. RNAlater is a tissue storage reagent that stabilises and protects cellular RNA in intact, unfrozen tissue samples. RNAlater eliminates the need to immediately freeze samples in liquid nitrogen.

RNA Extraction: Mixer Mill RNA Purification Method

Tumour tissue is removed from RNALater and added to a TriPure Isolation Reagent (Roche, Vilvoorde, Belgium). The tissue is then added to a Mixer Mill containing tungsten balls. Following disruption in the Mixer Mill, total cellular RNA was extracted from a maximum of 100 mg of tissue using the TriPure reagent according to the manufacturer's instructions (Qiagen, Venlo, Netherlands). RNA concentration was determined from the optical density value at 260 nm.

MAGE-A3 TaqMan RT-PCR Assay—Frozen Tissue.

cDNA corresponding to 50 ng of total RNA was amplified by PCR in a 25 µl mixture containing TaqMan buffer, 5 mM MgCl2, 0.4 mM dUTP, 0.2 mM of each nucleotide, 0.625 U of Ampli Taq Gold DNA polymerase, 0.05 U of UNG, 0.2 µM of each oligonucleotide primers and 0.2 µM of a TaqMan probe. Specific oligonucleotide primers and probes were used (Table 2; SEQ IDs 3, 4 and 13 and SEQ IDs 5, 6 and 14. The probes are labelled with the dyes FAM™, NED™ and VIC™ (Applied Biosystems, CA, USA) and have a Minor Groove Binding Moiety (MGB™; also from Applied Biosystems, CA, USA). Further experiments are now being carried out using the dye FAM instead of NED for the MAGE specific probes.

MAGE-A3 exon and beta-actin genes were amplified by quantitative PCR using TaqMan chemistry on the 7700 or 7900 system (PE Applied Biosystems, Warrington, UK). PCR amplification was also performed in an intron of MAGE-A3 gene to check the absence of genomic DNA contamination. The amplification profile was 1 cycle of 2 min at 50° C., 1 cycle of 12 min at 95° C. and 35 cycles of 15 s at 95° C. and 1 min at 60° C. The fluorescent signal generated by the degradation of the TaqMan probe was detected in real-time during all elongation steps.

Validation of the TaqMan RT-PCR Assay to Determine Specificity for MAGE-A3

Primers: SEQ ID NO: 3 and SEQ ID NO:4; Probe: SEQ ID NO: 13 (exon) —Taqman RT-PCR
Primers: SEQ ID NO: 1 and SEQ ID NO:2 (semi-quantitative PCR—for comparison studies)

Plasmids and Cell Lines

Plasmids employed contained the full length cDNA of the genes MAGE-A1 (MAGE-1; Genbank accession NM_004988), MAGE-A2 (MAGE-2; Genbank accession L18920), MAGE-A3 (MAGE-A3; Genbank accession NM_005362), MAGE-A4 (MAGE-4; Genbank accession 002362), MAGE-A6 (MAGE-6; Genbank accession NM_005363), MAGE-A8 (MAGE-8; Genbank accession NM_005364), MAGE-A9 (MAGE-9; Genbank accession NM_005365), MAGE-A10 (MAGE-10; Genbank accession NM_021048), MAGE-A11 (MAGE-11; Genbank accession NM_005366) and MAGE-A12 (MAGE-12; Genbank accession NM_005367). The cell lines MZ-2-3.0 (MAGE-A3 positive) and LB 23-1/2 (MAGE-A3 negative) were a kind gift from Professor Thierry Boon, Ludwig institute, Brussels, Belgium.

The specificity of the MAGE-A3 TaqMan method was tested using $1 \times 10^4$, $1 \times 10^5$, and $1 \times 10^6$ copies of plasmids containing the full length cDNA of MAGE-A1, 2, 3, 4, 6, 8, 9, 10, 11 and 12 genes.

A sequence comparison of the MAGE A genes (MAGE 1, 2, 3, 4, 6, 8, 9, 10, 11 and 12) at the area of the designed MAGE-A3 PCR primers and probes is shown on FIG. 14. The sequences of the forward and reverse MAGE-A3 primers are underlined; the sequence of the MAGE-A3 probe is boxed. The reverse primers are complementary to the region of the sequence they recognise, ie. A is T; G is C; T is A; and C is G.

MAGE-A3 TaqMan RT-PCR Positive controls: (i) A fragment of MAGE-A3 genomic DNA and (ii) known amounts of RNA extracted from the Gerl cell line MZ-2-3.0 (a melanoma cell line positive for MAGE-A3).

MAGE-A3 TaqMan RT-PCR Negative controls: (i) RNA extracted from cell culture LB 23-1/2, known to be MAGE-A3 negative, (ii) water blank in the RT reaction, and (iii) water blank in the PCR steps. 40 cycles of RT-PCR are performed. The negative control must be 35. Some of the results of the TaqMan experiments have been represented as 1/Ct.

Statistics: Comparison of the Two PCR Techniques

A 2×2 contingency table was created to compare the results from semi-quantitative RT-PCR (primers of SEQ ID NO:1 and SEQ ID NO:2) and real-time quantitative Taqman PCR (Primers: SEQ ID NO: 3 and SEQ ID NO:4; Probe: SEQ ID NO: 13), using techniques described herein (Table 3). The nominal scale variable featured two values: positive and negative. The negative values included zero and borderline ratings; by borderline rating is meant the rating is between 0.8% and 1.2% Gerl from the semi-quantitative RT-PCR and all results below 1% from the TaqMan assay. The positive values were graded based on visible scoring of the gel bands in relation to beta-actin expression for the semi-quantitative RT-PCR method and included all results ≥1% from the TaqMan assay. The agreement between both methods was calculated as the number of double negative plus double positive samples divided by the total number of samples. The McNemar test was used to compare proportions of discordant pairs (negative-positive). Confidence intervals (CI) were calculated.

Optimization of the Quantitative, TaqMan RT-PCR
TaqMan RT-PCR for MAGE-A3 Using Sybr Green.

Sybr green is a component which binds amplicons non-selectively, without a sequence specific probe. Real-time RT-PCR was carried out on the gene clones of the MAGE-A family, using four different dilutions of the MAGE-A clones (20 pg, 2 pg, 0.2 pg and 0.02 pg) (FIG. 1, where results are shown as 1/CT on the Y-axis). A positive result was obtained for MAGE-A3 at 14 Ct and a value of 16 Ct was obtained for MAGE-A6 (at 20 pg of plasmids). MAGE A4, A8 and A9 showed a Ct level of 30 and the other MAGE genes showed very limited expression at 35 Ct and above.

TaqMan RT-PCR for MAGE-A3 Using Sequence-Specific Probe.

Figure 2:
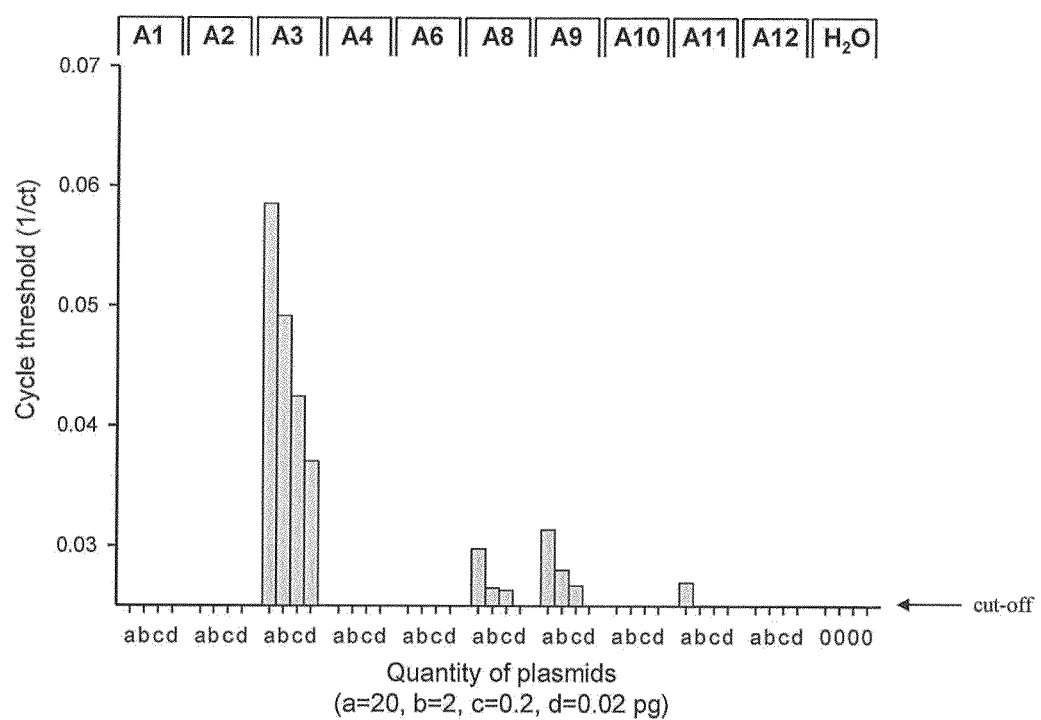
FIG. 2: Specificity of Minor Groove Binding (MGB) probe TaqMan RT-PCR for MAGE-A3 expression.

Using the same MAGE-A3 primers (SEQ ID 3 and 4) but with a probe (SEQ ID No 13), the effectiveness to discriminate MAGE-A3 from A6 was tested using different dilutions of the relevant clones of MAGE-A family members (FIG. 2). Firstly, MAGE-A3 Ct had an expected decrease in each of the dilutions. The MAGE-A6 clone does not show a high 1/Ct when a probe is used, indicating no cross reactivity.

Figure 3:
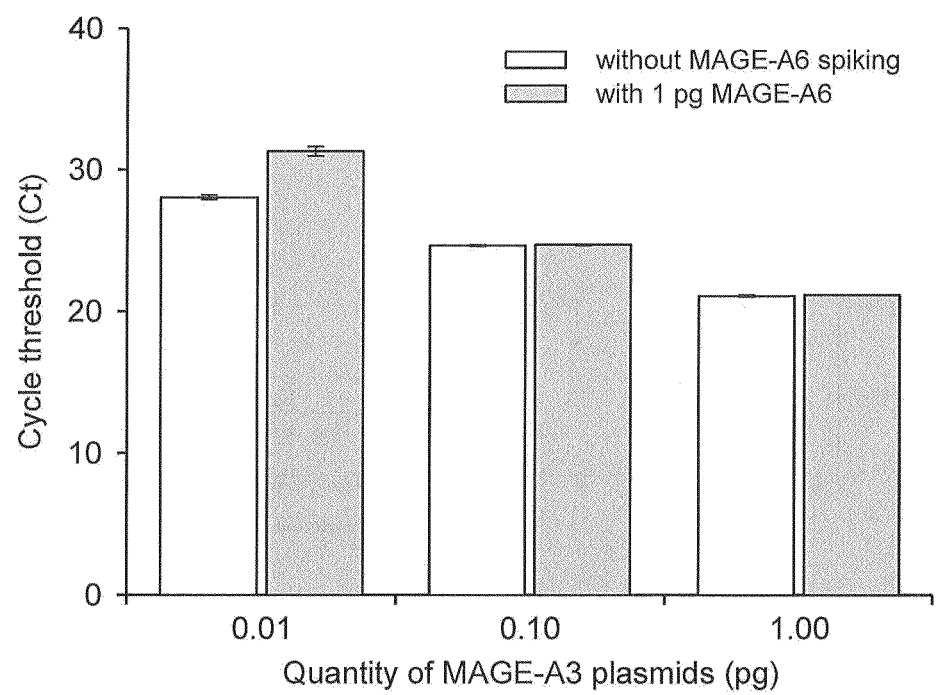
FIG. 3: Specificity testing of MAGE-A3 primers in the presence of MAGE-A3 and MAGE-6 plasmids.

The spiking of $1 \times 10^6$ MAGE-A6 plasmid to the dilution of the MAGE-A3 plasmid, as shown in FIG. 3, does not have any effect and the result mirrors the MAGE-A3 plasmid titration result. This shows no competitive effect of MAGE-A6 in the presence of MAGE-A3 using TaqMan PCR.

Results
Tumour Expression of MAGE-A3, Comparison of Semi-Quantitative and Quantitative Methods The TaqMan-specific quantitative PCR was further validated against the standard semi-quantitative RT-PCR for MAGE-A3 (using primers SEQ ID No 1 and 2). 71 tumour samples from NSCLC patients were used to compare directly between quantitative (using primers SEQ ID NO: 3 and 4 and probe SEQ ID NO:13) and semi-quantitative methods of MAGE-A3 expression (using primers SEQ ID NO:1 and 2).

The results indicate a good concordance of 95.8% (Table 3) between the two methods with 68/71 in agreement. The quantitative TaqMan RT-PCR and the semi-quantitative RT-PCR assay were discordant for three samples, in which the Semi-quantitative RT-PCR assay overestimated the positivity of the results. However, the McNemar test revealed a symmetric repartition of these three discordant results (p=0.25), indicating that neither technique tended to produce more discordant results compared to the other technique. On closer investigation, the variable level of beta-actin expression on these samples resulted in a false positive for the semi-quantitative RT-PCR method.

Figure 4:
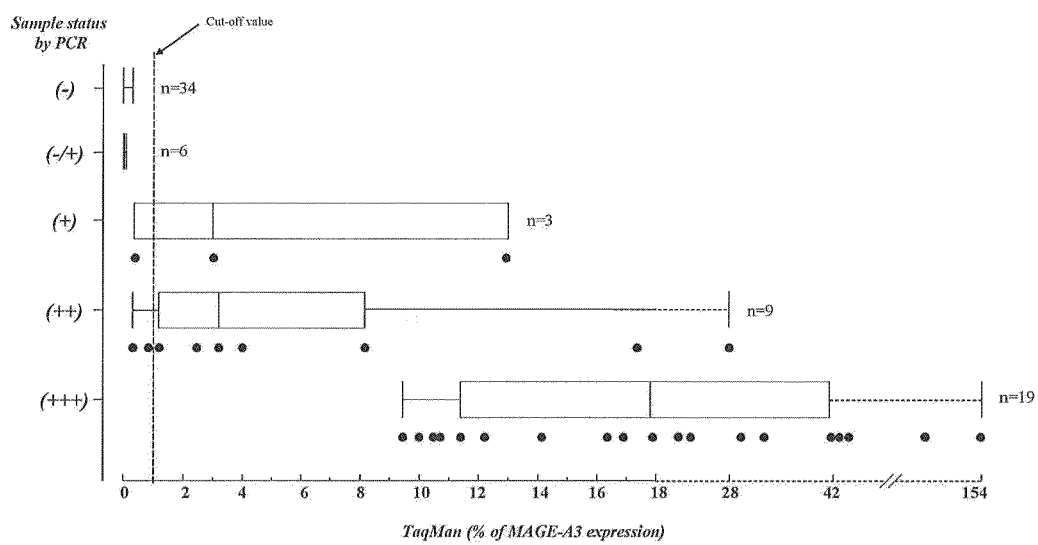
FIG. 4: Tumour Expression of MAGE-A3 as measured by quantitative TaqMan PCR.

A box plot (FIG. 4) was used to represent the dispersion of the TaqMan PCR data for each class defined for the Semi-quantitative RT-PCR. Although the concordance between both methods, based on the 2×2 contingency table, was excellent, the box plots revealed some overlap between the different classes, indicating that the semi-quantitative rating did not completely coincide with the quantitative TaqMan RT-PCR measurement. The overlap may be due to the fact that the rating was performed by different operators at different occasions, which may increase the variability. In that sense, the quantitative TaqMan RT-PCR assay is much more independent of those factors and hence more reproducible.

Example 3

Analysis of Paraffin-Fixed Tissue (FFPE) by RT-PCR

Materials and Methods

RNA was extracted from FFPE samples using a proprietary method of Response Genetics Inc., as disclosed in U.S. Pat. No. 6,613,518; U.S. Pat. No. 6,610,488; U.S. Pat. No. 6,428,963; U.S. Pat. No. 6,248,535, incorporated herein by reference. Alternatively RNA may be obtained from paraffin-fixed tissue according to any suitable published method. For example, tissue sections may be removed from paraffin using d-limonene or another lysis buffer and then washed in an ethanol-based solution. The sections may then be treated with proteinase K overnight and then washed and the RNA may be purified using column chromatography. Real-time Taqman RT-PCR was performed on the samples using primers SEQ ID NO: 3 and SEQ ID NO:4 and probe SEQ ID NO:13; primers and probes developed for use in frozen tissue (see Example 2, above).
Results: Mage A3 Expression Table 4 shows results expressed as Ct values, for the Formalin-Fixed, Paraffin-Embedded (FFPE) tissue. The numbers of the Y-axis represent Human tumor samples 990118-990784. Also included in the analysis were positive controls: TC1 (Mage3); Gerl (MAGE-A3 melanoma cell line); and CRL 1675 (melanoma cell line). The Ct values are higher than what would be expected for frozen tissue based semi-quantitative RT-PCR MAGE-A3 primers The level of 36-37 Ct is considered the uppermost limit of sensitivity for the purpose of these experiments. The Gerl MAGE-A3 positive control is at 31 Ct and just within the sensitivity limit but greatly reduced from the semi-quantitative RT-PCR assay. With these levels the primers and probe for MAGE-A3 quantification in frozen tissue (Table 2, exon 3 MAGE-A3 specific primers SEQ ID NO:3 and SEQ ID NO:4 and probe SEQ ID NO:13) may not be sensitive enough to detect MAGE-A3 expression within FFPE-tumour samples: samples that are MAGE-A3 positive but only express MAGE-A3 at low levels may not be detected.

Figure 5:
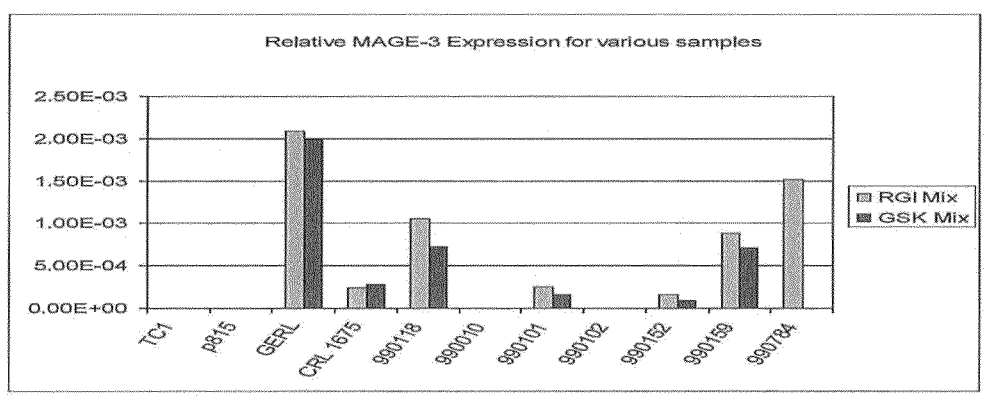
FIG. 5: Test of MAGE-A3 expression.

Samples of positive controls from FFPE tissue were included in the experiment: TC1 (Mage3) and Gerl (MAGE-A3 positive control) and CRL 1675. Human tumors 990118-990784 were analysed by Taqman quantitative RT-PCR using the frozen tissue primers SEQ ID NO: 3 and SEQ ID NO: 4 and probe SEQ ID NO: 13 using RNA from paraffin tissue. The result of this analysis is shown in FIG. 5.
Redesigning of MAGE-A3 TaqMan Primers for Use in FFPE Tissue The size of the amplicon for the frozen tissue RNALater based MAGE-A3 assay, (described in example 2) is over 100 bp. In order to obtain more sensitive results for degraded RNA found in FFPE samples, new primers were designed to reduce the size of the amplicon, in order to increase the sensitivity of the MAGE-A3 assay (Table 5). For both the assays described in Examples 2 and 3 an MGB™ (Minor Groove Binding) probe was used to increase the specificity of the assays. The MGB probe binds into the minor groove of the DNA forming a extremely stable duplex resulting in an increase in primer specificity
Testing of the New MAGE-A3 Primers for Specificity and Sensitivity The newly designed primers sets (Table 5) were tested on the cDNA of Mage-A gene family members (FIG. 6a), in which Set 1 is primers: SEQ ID NO:7, SEQ ID NO:8, probe: SEQ ID NO:15; Set 2 is primers: SEQ ID NO:9, SEQ ID NO:10, probe: SEQ ID NO:16; Set 3 is primers: SEQ ID NO:11, SEQ ID NO:12, probe: SEQ ID NO:17; and Set 4 is primers: SEQ ID NO:3, SEQ ID NO:4, probe: SEQ ID NO:13.

Figure 6A:
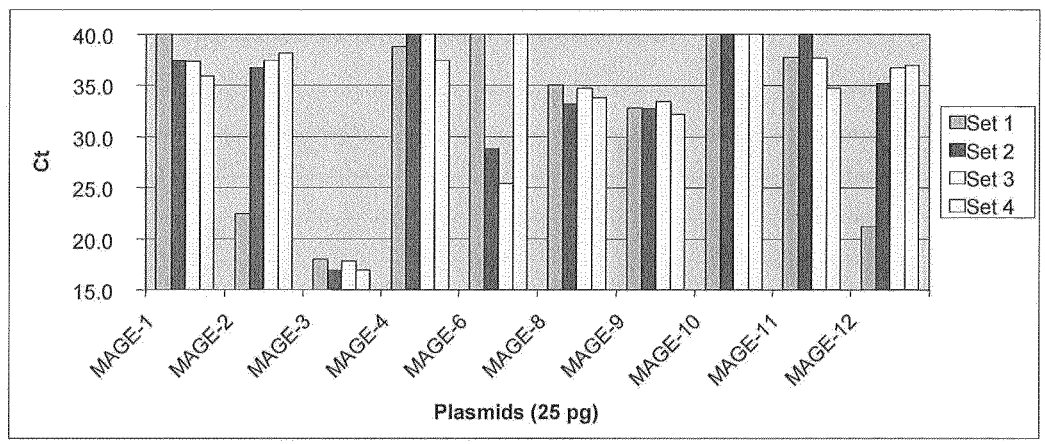
FIG. 6a: Specificity of the MAGE-A3 primers designed for FFPE tissue use.
Figure 6B:
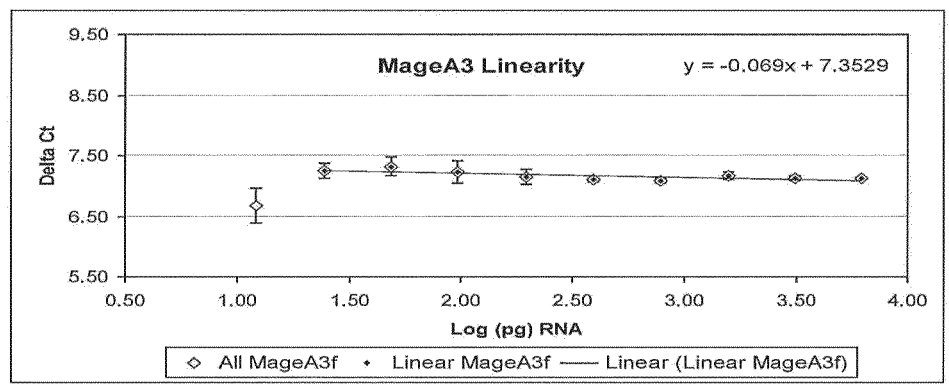
FIG. 6b: Testing linearity of the primers over differential amounts of RNA.

As shown in FIG. 6a, the primers SEQ ID NO: 7 and 8 have high Ct levels for MAGE-A3 but also for Mage-2 and Mage-12. The primers SEQ ID NO: 9 and 10 have high Ct levels for MAGE-A3 and a slight Ct for MAGE-A6 but this is out with the normal range of MAGE-A3 expression. The primers SEQ ID NO: 11 and 12 are slightly less sensitive than SEQ ID NO: 9 and 10. Thus, in the present experiments, the primers SEQ ID NO: 9 and 10 were chosen to be further tested in FFPE tissue. These SEQ ID NO: 9 and 10 primers were further tested in a serial dilution of RNA and showed good linear range until the lower dilutions, suggesting the primers should have a good sensitivity and are suitable for the assay (FIG. 6b).

Comparison of Frozen vs. FFPE TaqMan Assays for MAGE-A3

Figure 7:
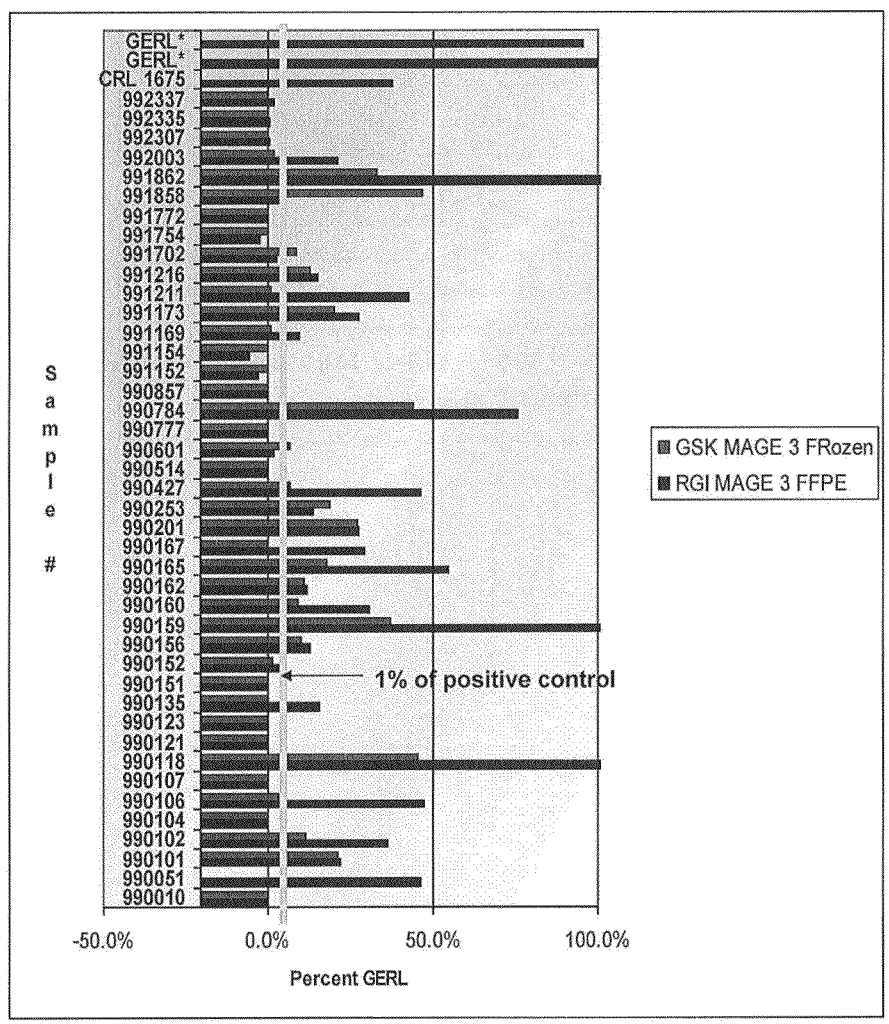
FIG. 7: Comparison between RNA later frozen assay and the FFPE tissue PCR.
Figure 8:
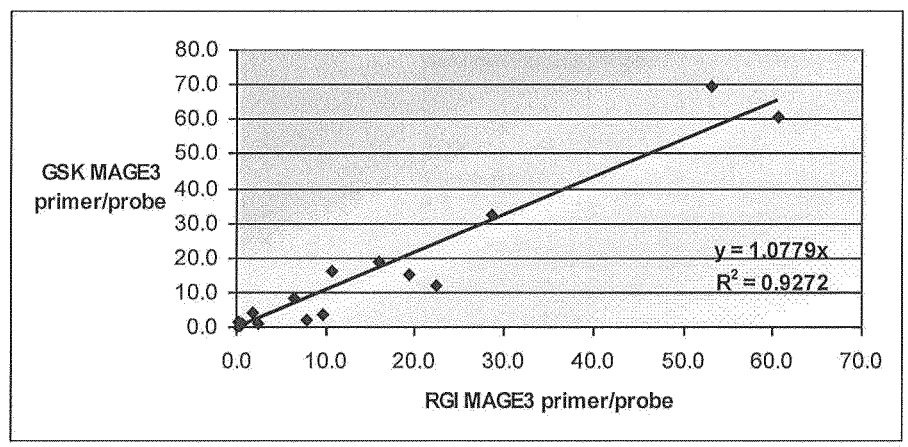
FIG. 8: Relative comparison of the RNA later frozen and FFPE based MAGE-A3 assays

Forty two FFPE tumour samples were compared using primers SEQ ID NO: 9, SEQ ID NO: 10 and probe SEQ ID NO: 16 with the same assay completed in frozen tissue using primers SEQ ID NO: 3, SEQ ID NO: 4 and probe SEQ ID NO: 13 (FIG. 7). The level of positivity of the assay is set at 1% gerl (positive control) and comparing directly there seems to be some concordance between the two assays. There are some MAGE-A3 positive patients MAGE-A3 that did not agree with the MAGE-A3 frozen tissue assay; this could be explained by the macro dissection of the tumoral areas causing an increase in the purity of tumour cells which express the MAGE-A3. The removal of most of the diluting normal cells caused a positive MAGE-A3 result An $R^2$ value (statistical test for linear correlation) of 0.92 was shown between the FFPE tissue and the RNA later frozen tissue suggesting a good correlation between the two methods (FIG. 8)

Example 4

COBAS™ Taqman MAGE-A3 Test

TABLE 7

COBAS ™ TaqMan MAGE-A3 Primer and Probe Sequences

| COBAS ™ TaqMan MAGE-A3 Primer Sequences | |
|---|---|
| MAGEA3f-623F: (HW_MAGEA3_F; SEQ ID NO: 11) | 5'TGTCGTCGGAAATTGGCAGTAT3' |
| MAGEA3f-697R:(HW_MAGEA3_R; SEQ ID NO: 12) | 5'CAAAGACCAGCTGCAAGGAACT3' |

| COBAS ™ TaqMan MAGE-A3 Probe Sequence | |
|---|---|
| MAGEA3F-646MOD SEQ ID NO: 53 | 5'-ELFLLLFFLQGLGALFLLFAGFAA AGFLLFP-3' |

E = FAM Reporter Dye,
F = 5-Methyl dC,
Q = BHQ2 Quencher,
L = 5-Propynyl dU,
P = Phosphate,
I = HEX Reporter
MAGEA3F-646MOD probe sequence comprises the following modified nucleotides (SEQ ID NO: 54): 5'-TCTTTCCTGTGATCTTCAGCAAAGCTTC-3'

TABLE 8

COBAS TaqMan beta-actin Primer and Probe Sequences

| TagMan beta-actin Primer Sequences | |
|---|---|
| RGI_BACT_F2: (SEQ ID NO: 55) | 5'-GAGCGCGGCTACAGCTT-3' |
| RGI_BACT_R2: (SEQ ID N6: 56) | 5'-TCCTTAATGTCACGCACGATTT-3' |

| TaqMan beta-actin Probe Seuence | |
|---|---|
| HW_RGIBACT_H: (SEQ ID NO: 57) | 5'-IACCACCAQCGGCCGAGCGGP-3' |

E = FAM Reporter Dye,
F = 5-Methyl dC,
Q = BHQ2 Quencher,
L = 5-Propynyl dU,
P = Phosphate,
I = HEX Reporter

TABLE 9

Sample & Control Valid CT range

| Controls | Valid Ct Range |
| --- | --- |
| FFPET Sample Mage Gene 50 ng FAM | <35.2 |
| FFPET Sample Bactin Gene 50n HEX | <32.1 |
| 100% Gerl Mage Gene 50 ng FAM | 26.0-29.5 |
| 100% Gerl Bactin Gene 50 ng HEX | 24.0-27.0 |
| 1% Gerl Mage Gene 0.5 ng FAM | 33.0-35.5 |
| 1% Gerl Bactin Gene 0.5 ng HEX | 29.0-32.5 |
| 100% UHR Mage Gene 50 ng FAM | 25.0-28.0 |
| 100% UHR Bactin Gene 50 ng HEX | 22.0-25.0 |
| 1% UHR Mage Gene 0.5 ng FAM | 31.0-33.0 |
| 1% UHR Bactin Gene 0.5 ng HEX | 27.0-29.0 |
| P53 Positive Control DNA 20 ng FAM | 26.5-29.0 |
| Negative Control (NC) | >38.0 |

TABLE 10

Thermal cycling profile
PCR Thermal Profile for MAGE-A3 Exclusivity Experiment

| Steps | Description | Temperature | Time | Cycle number |
| --- | --- | --- | --- | --- |
| 1 | UNG Decontamination | 50° C. | 5 min. | 1X |
| 2 | Denaturation | 95° C. | 15 sec. | 2X |
|   | Annealing | 63° C. | 25 sec. |   |
| 3 | Denaturation | 92° C. | 15 sec. | 53X |
|   | Annealing | 63° C. | 50 sec. |   |
| 4 | Post Cycle | 40° C. | 2 min. | 1X |

TABLE 11

RT-PCR Thermal Profile for Linearity and RT-PCR Efficiency,
Analytical Sensitivity (Limit of Detection), Method Correlation,
and Reproducibility Experiments

| Steps | Description | Temperature | Time | Cycle number |
| --- | --- | --- | --- | --- |
| 1 | UNG Decontamination | 50° C. | 5 min. | 1X |
| 2 | Denaturation | 95° C. | 1 min. | 1X |
| 3 | Reverse Transcription | 60° C. | 20 min. | 1X |
| 4 | Denaturation | 95° C. | 15 sec. | 2X |
|   | Annealing | 63° C. | 25 sec. |   |
| 6 | Denaturation | 92° C. | 15 sec. | 53X |
|   | Annealing | 63° C. | 50 sec. |   |
| 7 | Post Cycle | 40° C. | 2 min. | 1X |

Relatively high anneal temperature of 63° C. was implemented to improve MAGE-A3 specificity relative to the other MAGE-A family members.

Data Analysis

Ct values for MAGE-A3 and β-actin are calculated using AMPLILINK™ 3.1 software (Roche, Calif., USA) on the COBAS™ TaqMan 48 Analyzer workstation (Roche, Calif., USA) based on assay parameters defined in the Test Definition File. Data analysis for gene expression will be performed by extracting the Ct values for MAGE-A3 and β-actin from AMPLILINK™ for downstream calculations to determine MAGE-A3 gene expression relative to the β-actin gene. For each run, controls will be included to establish the threshold MAGE-A3 expression level that needs to be met or exceeded in order for the sample to be called MAGE-A3 positive. As a positive control, RNA from the cell line GERL is used. GERL RNA is diluted 1:100 (1% GERL) in water and the MAGE-A3 Ct was determined. In addition, undiluted GERL RNA (100% GERL) is tested with no dilution for β-actin Ct measurement. A delta Ct value between β-actin Ct from the 100% GERL control minus the MAGE-A3 Ct from the 1% GERL control is calculated and relative expression of MAGE-A3 determined based on the calculation below:

$$\text{MAGE-}A3 \text{ Threshold Expression} = 2^{\wedge(\beta\text{-actin } Ct \text{ from } 100\% \text{ GERL}-\text{MAGE-}A3 \text{ } Ct \text{ from } 1\% \text{ GERL})}$$

For paraffin embedding samples, the same control strategy will be used except that RNA from GERL FFPE Xenograft extracted using the QIAGEN FFPE method will replace the GERL cell line RNA for the establishment of the threshold expression.

Since the COBAS™ Taqman MAGE-A3 testis a multiplex reaction, MAGE-A3 and β-actin Ct values are derived from the same reaction tube. MAGE-A3 relative expression is calculated for each test sample by the following equation:

$$\text{MAGE-}A3 \text{ Expression in test sample} = 2^{\wedge(\beta\text{-actin } Ct \text{ from sample}-\text{MAGE-}A3 \text{ } Ct \text{ from sample})}$$

If MAGE-A3 Expression in the test sample is greater than or equal to that of the MAGE-A3 threshold level established from the GERL RNA Controls, than the sample is called positive for MAGE-A3. If MAGE-A3 Expression in the test sample is less than that of the MAGE4A3 threshold level established from the Controls, than the sample is called negative for MAGE-A3.

MAGE-A3 expression will be determined by taking the average of the MAGE-A3 Ct and β-actin Ct values from the replicated for each specimen for the calculation of delta Ct (β-actin–MAGE A3 Ct). If one replicate has a MAGE-A3 Ct or β-actin Ct less than the Ct cutoff of test, but the other replicate has a MAGE-A3 Ct or β-actin Ct greater than the Ct cutoff, the sample will be retested. If both replicates have β-actin Cts greater the Ct cutoff, the sample is marked as β-actin Ct outside of range and no result is given. If both replicates have MAGE-A3 Ct values greater than the MAGE-A3 Ct cutoff value, but MAGE-A3 expression is above the threshold, then the sample is labeled as MAGE-A3 Ct out of range and no result is given. This strategy for data analysis is consistent with the cross-validation studies performed for method correlation that are described in Section "Method correlation", below.

For the COBAS™ Taqman MAGE-A3 test, Human QPCR Human Reference Total RNA (UHR) from Stratagene may be implemented the Positive Control and set an expression threshold based on MAGE-A3 expression in this well characterized RNA. Diluted UHR may be tested with every run together with the GERL RNA controls to establish an appropriate expression threshold with the UHR Control.

Sample and Reagent Storage Conditions

All RNA and DNA including plasmids, P53 positive control DNA, clinical FFPET RNA, UHR, GERL, and STAC are stored at −80° C. All test reagents including Universal RNA Master Mix, primer/probe mix, co-factor blend, and sample diluent/negative control are stored at 2-8° C.

MAGE-A3 Exclusivity

Experimental Testing of Primers and Probes with DNA Plasmids Containing MAGE-A Family Members Purpose: To determine the ability of the test to specifically amplify the MAGE-A3 gene while excluding significant co-amplification/detection of other related genes.

Sample material: Plasmid DNA containing MAGE-A3 and related family members will be tested (for details of plasmids see Example 2, above).

Procedure: Experimental testing of the COBAS TaqMan MAGE-A3 Test using DNA plasmids containing MAGE-A family members to determine if related genes are amplified and detected in significant amounts.

Each plasmid DNA sample was tested in triplicate at four different DNA concentrations (20, 2, 0.2, 0.02 pg). Thermal Cycling profile shown in Table 10 was modified to remove the reverse transcription step at 60° C. for 20 minutes. Concentration of plasmid DNA was determined by Nanodrop analysis.

Analysis:

Ct values for MAGE-A3 plasmid were determined and compared with Ct values from MAGE-A1, MAGE-A2, MAGE-A4, MAGE-A6, MAGE-A8, MAGE-A9, MAGE-A10, MAGE-A11, and MAGE-A12 plasmids. Delta Ct was calculated by subtracting the MAGE-AX Ct (each related family member) by the MAGE-A3 Ct. Ct average values from four replicates was used for the calculations of Ct and delta Ct.

Acceptance Criteria:

Delta Ct Values must be greater than equal to 10 between MAGE-A3 and all other plasmids except MAGE-A6.

MAGE-A3 Exclusivity Results

In Tables and Figures herein, on some occasions the term "CURIE" is used in place of "MAGE"; however, the term "MAGE" is intended in all instances.

Figure 17:
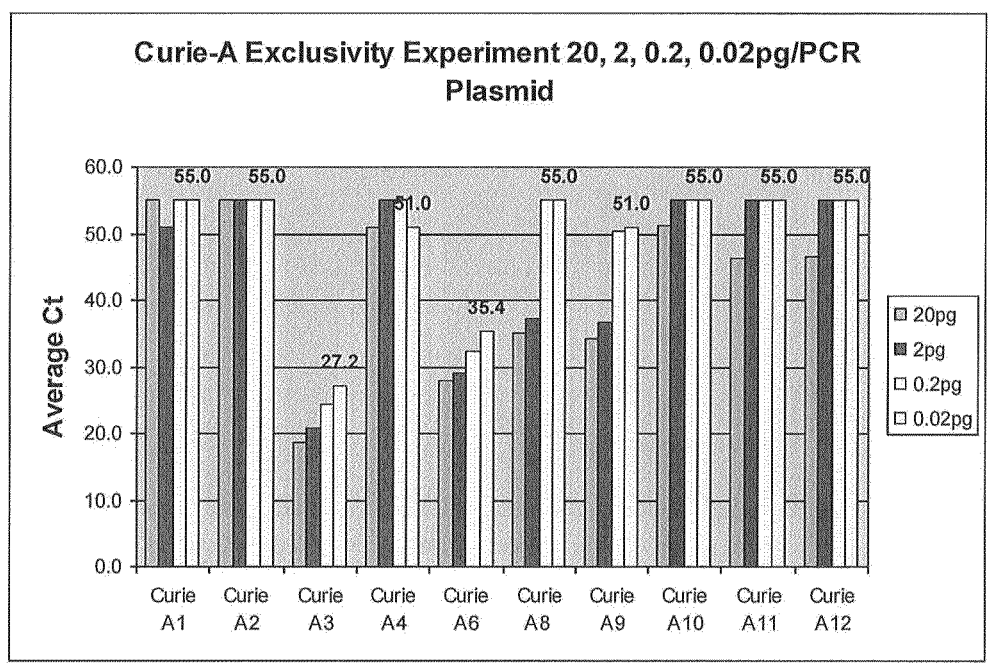
FIG. 17: Graphical Comparison of Ct values from MAGE-A Plasmids using 20, 2, 0.2 0.02 pg of DNA
Figure 18:
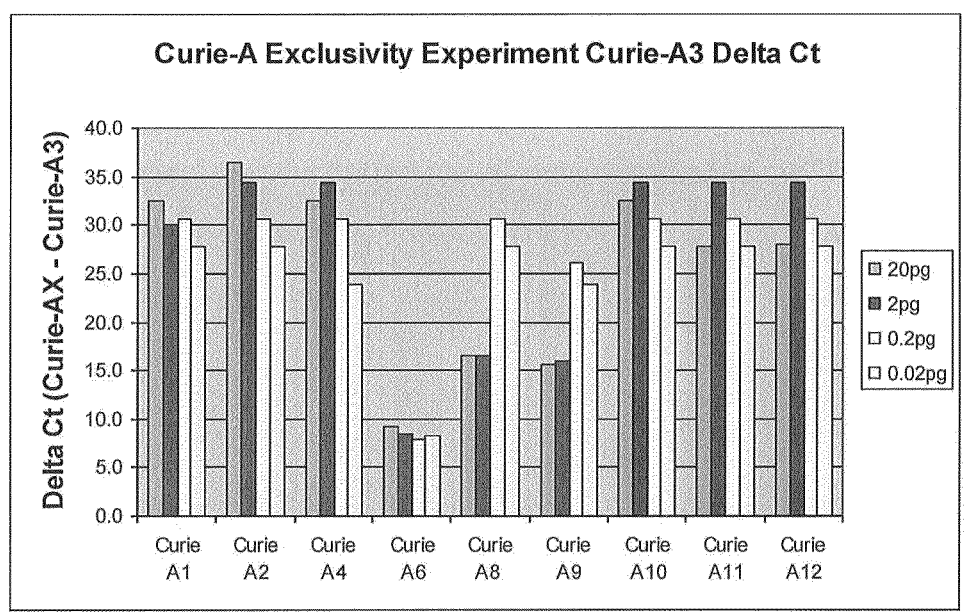
FIG. 18: Graphical Comparison of Delta Ct values Relative to MAGE-A3 for other MAGE-A Plasmids using 20, 2, 0.2 0.02 pg of DNA

Ct values are shown for all MAGE plasmids tested in Table 12 and FIG. 17 shown below. For plasmids where there was no amplification, a Ct value of 55 was assigned since there are 55 cycles in the thermal cycling profile. As expected, MAGE-A3 Cts are the earliest for all levels tested (Table 12 and FIG. 17). Delta Ct Values were greater than 10 cycles between MAGE-A3 and all other plasmids except MAGE-A6 (Table 13 and FIG. 18). A Delta Ct between MAGE-A3 and MAGE-A6 was not required since 95% of the patients that express MAGE-A6, also express MAGE-A3.

Delta Ct between MAGE-A3 and MAGE-A6 for 20 pg, 2 pg, 0.2 pg and 0.02 pg of plasmid DNA input was 9.3, 8.4, 7.8, and 8.2 cycles, respectively. Since most MAGE-A3 Ct values for RNA from FFPE samples was shown to be greater than 27.2 for FFPE samples tested, signal from MAGE-A6 will be minimal since a delay of 8.2 cycles would generate a Ct value outside of the range of the assay.

Acceptance Criteria for exclusivity were met.

Table 14 shows MAGE-A3 Exclusivity Experiment Validation; control Cts were within validated range. Experiment passed validation. Tables 15 and 16 show MAGE-A3 Exclusivity Experiment details.

Linearity and RT-PCR Efficiency

Purpose: To determine the linearity and reverse transcription efficiency of the Test.

Sample material: Serial dilutions of FFPE Xenograft GERL RNA were used for linearity and RT-PCR efficiencies studies.

Procedure: FFPE Xenograft GERL RNA was 2-fold serial diluted from 100 ng to 0.1 ng and tested using the COBAS TaqMan MAGE-A3 Test to determine the linear range of the assay. Ten replicates were tested at each concentration level.

Analysis:

Ct values for each replicate for both MAGE-A3 and β-actin were plotted versus log (base 2) of input concentration of RNA to calculate the slope of the line and the efficiencies of RT-PCR. RT-PCR amplification efficiency was calculated using the equation:

$$\text{Slope}=-1/\log(\text{base 2})*\text{Amplification Efficiency (AE)}.$$

Amplification Efficiency of 2 is equivalent to 100%. Delta Ct values (MAGE-A3 Ct−β-actin C0 for each replicate was plotted versus log (base 2) of input concentration of RNA to determine the Delta Ct slope. Averages, standard deviation and percent coefficient of variation (% CV) for MAGE-A3 Ct, β-actin Ct and Delta Ct were calculated from all ten replicates Acceptance Criteria Linearity:

Linear range of the assay was determined based on the following criteria:

MAGE-A3 Ct CV<5%

β-actin Ct CV<5%

Delta Ct CV<20%

−0.10<Delta Ct slope <0.10

R2>0.95

Acceptance Criteria RT-PCR Efficiency:

MAGE-A3 RT-PCR Amplification Efficiency >80%

β-actin RT-PCR Amplification Efficiency >80%

RT-PCR Amplification Efficiency difference between MAGE-A3 and β-actin within 10%

Linearity/RT-PCR Efficiency Results

Figure 20:
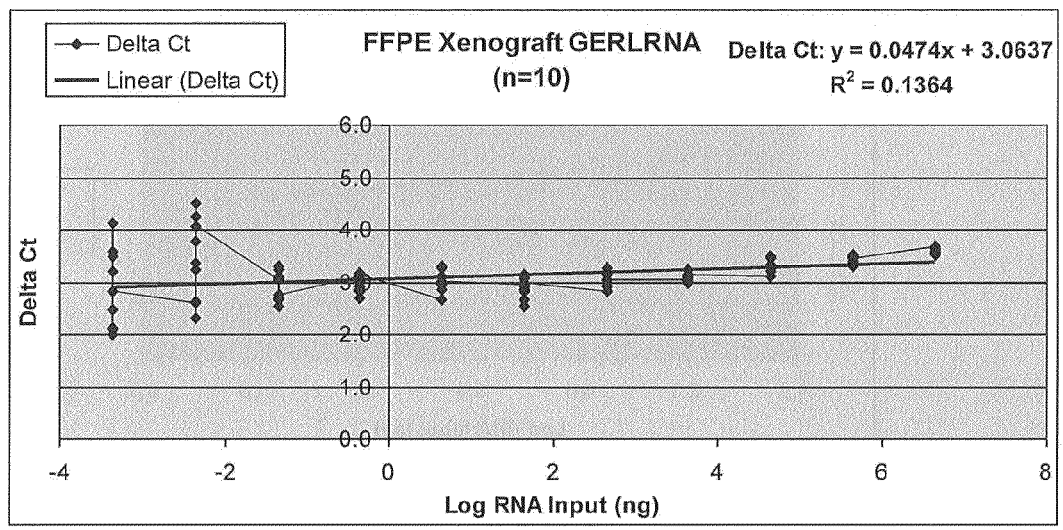
FIG. 20: shows a graph with log (base 2) of RNA input versus Delta Ct between MAGE-A3 and β-actin.

FIG. 20 shows a graph with log (base 2) of RNA input versus Ct values for MAGE-A3 and β-actin. The COBAS TaqMan MAGE-A3 Test is linear between input values of 100-0.1 ng of GERL RNA extracted from FFPE Xenograft using the QIAGEN method based on R2 values. R2 values were 0.983 for MAGE-A3 and 0.998 for β-actin. These values are above the specification of R2>0.95. In addition, both MAGE-A3 and β-actin Ct for all 10 replicates at each level tested are below the specification of CV<5% as shown in Table 17.

Figure 19:
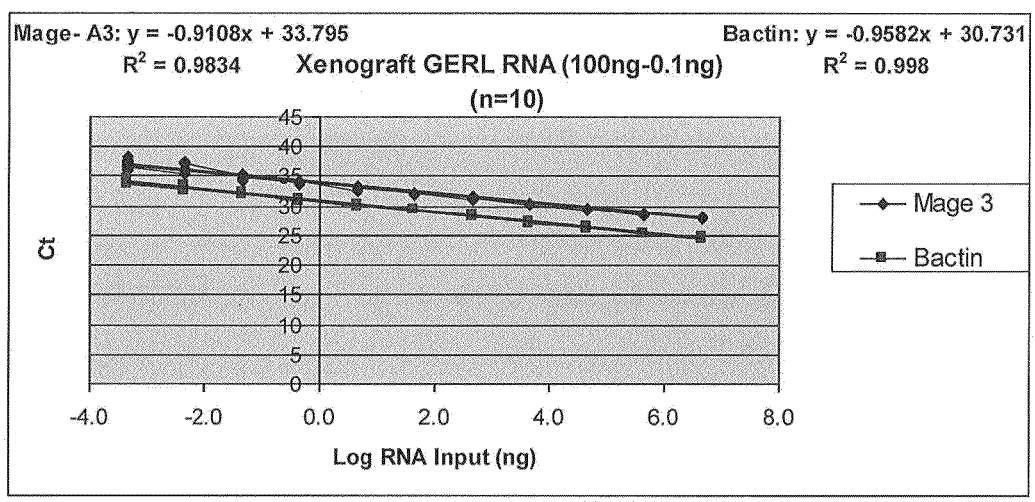
FIG. 19: Linearity of FFPE Xenograft GERL RNA-2-fold serial dilutions from 100 to 0.1 ng of RNA Input

The RT-PCR amplification efficiency of MAGE-A3 and β-actin was calculated from the slope of the line generated from plotting log (base 2) of RNA input versus Ct values for MAGE-A3 and β-actin shown in FIG. 19. The amplification efficiency of RT-PCR can be calculated using the following equation:

$$\text{Slope}=-1/\text{Log}(\text{base 2})*\text{Amplification Efficiency (AE)}.$$

Amplification efficiency for was 2.14 (107%) and 2.06 (103.1%) for MAGE-A3 and β-actin, respectively. AE was above the specification of 80% for MAGE-A3 and β-actin. The difference in AE between the two genes was 3.9%, which was also within the specification of +10%.

FIG. 20 shows a graph with log (base 2) of RNA input versus Delta Ct between MAGE-A3 and β-actin. Delta Ct slope is 0.0474, well within the slope specification of −0.10 to 0.10. At the two lowest levels of RNA input tested (0.2 & 0.1 ng), the % CV for Delta Ct was above the specification of 20%. As a result, the last two RNA input levels were not included in the linear range of the assay. The linear range of the assay using GERL Xenograft RNA is 100 ng-0.39 ng of RNA.

Based on these data, acceptance Criteria for linearity and RT-PCR efficiency were met.

Table 18 shows RT-PCR Amplification Efficiency of MAGE-A3 and β-actin; Table 19 is Linearity/RT-PCR Efficiency Experiment Validation Control Cts were within validated range. Experiment passed validation.

Tables 20, 21 and 22 Provide Linearity/RT-PCR Efficiency Experiment Details

Analytical Sensitivity (Limit of Detection)

Purpose: To establish the lowest concentration RNA where MAGE-A3 gene expression can be detected by the COBAS™ TaqMan MAGE-A3 Test at least 95% of the time.

Sample material: Analytical sensitivity was evaluated using RNA isolated from FFPE Xenograft tissue using the QIAGEN RNeasy FFPE Kit with additional DNase step. RNA was extracted from two FFPE xenografts derived from two different RNA cell lines. One Xenograft referred to as GERL expresses MAGE-A3. The other Xenograft referred to as STAC does not express MAGE-A3. RNA from these two Xenografts were used for mixture experiments in order to test 5% GERL RNA in a background of 95% STAC RNA, 1% GERL RNA in a background of 99% STAC RNA, and 0.5% GERL RNA in a background of 99.5% STAC RNA. These three different mixtures of GERL and STAC RNA were tested at four different total RNA levels.

Procedure: Twenty-four test results were generated from 4 independent dilutions series of GERL and STAC RNA mixtures. Four levels of RNA input were tested (100, 50, 25, and 12.5 ng). Six replicates for each level was tested.

Analysis: Determine of the level of RNA at which >95% positivity rate for MAGE-A3 is obtained based on Ct value within the validated range of the assay.

Acceptance Criteria: LOD<50 ng input Total RNA for detection of 1% GERL

Limit of Detection Results

Hit rate is defined as Ct value within the linear range of the assay based on linearity experiments described in this report. To determine the end of the Ct range, the MAGE-A3 and β-actin Cts from the 0.39 ng RNA input level from the linearity study (end of linear range) were averaged and 95% confidence limits were calculated for the MAGE-A3 and β-actin Cts. Based on these calculations, MAGE-A3 Ct must be less than or equal to 35.2 and β-actin Ct must be less than 32.1 for the sample to be considered a hit. Hit rates for MAGE-A3 and β-actin are shown in Table 23 and Table 25. Hit rate percentages for MAGE-A3 and β-actin are shown in Table 24 and Table 26.

Limit of Detection is 50 ng input RNA where 1% GERL RNA diluted in 99% STAC RNA is detected >95% of the time based on MAGE-A3 Ct falling within the validated range of the assay. Acceptance Criteria for Analytical Sensitivity (Limit of Detection) are met.

Limit of Detection Experiment Validation.

MAGE Gene FAM Control Cts are shown in Table 27; β-actin HEX Control Cts are shown in Table 28. Control Cts are within validated range. Experiment passed validation.

Table 29; Table 30; and Table 31 show Limit of Detection Experiment Details

Method Correlation

Purpose: To correlate and cross validate the COBAS™ TaqMan MAGE-A3 Test and a Prototype Assay on clinical FFPET samples.

Sample material: Approximately 120 clinical FFPET samples of adequate quality were analyzed using the COBAS TaqMan MAGE-A3 Test and using the Prototype Assay.

Procedure: RNA was extracted using the QIAGEN™ RNeasy FFPE Kit with additional DNase Step. One extraction was performed for each FFPET sample, the sample was split and one aliquot was tested by COBAS TaqMan MAGE-A3 Test and one aliquot was tested using the prototype assay. Identical controls were run for both assays to establish the MAGE-A3 expression threshold.

Analysis:

The MAGE-A3 call for each sample was reported as positive or negative based on the MAGE-A3 expression threshold generated by the GERL RNA controls. Results between the two assays were compared to establish the positive and negative by comparator percent agreement values of the RMS test.

For percent agreement calculations, results obtained previously using a two step RT-PCR assay for frozen tissue was used to resolve discordant results.

Positive by Comparator Percent Agreement=# of samples correctly called MAGE-*A3* expressor/# number of samples tested*100

Negative by Comparator Percent Agreement=# of samples correctly called MAGE-*A3* non-expressor/# number of samples tested*100

Acceptance Criteria:
Positive by Comparator Percent Agreement >85%
Negative by Comparator Percent Agreement >85%

Cross-validation of clinical specimens from a NSCLC clinical trial was performed to assess the positive and negative by comparator percent agreement of the COBAS TaqMan MAGE-A3 Test. The MAGE-A3 prototype RT-PCR assay was used as a comparator for these studies. In the event of discordance between results, previous results generated from the same sample as fresh frozen tissue that was not manually micro-dissected would be used for discordant result resolution.

Using the QIAGEN RNeasy FFPE method with the DNase I digestion step, RNA was extracted from 131 manually micro-dissected clinical FFPE specimens. Each sample was then divided equally between RMS and RGI for testing using the RMS COBAS TaqMan MAGE-A3 Test and the RGI prototype assay. Data analysis was performed as described in Section 3, in this report where MAGE-A3 expression threshold was determined based on the 1% GERL RNA control.

Method Correlation/Cross Validation Results

RNA samples were extracted from 131 NSCLC FFPE clinical specimens. Seven samples had genomic DNA contamination greater than 25% based on the RGI's RT control reaction. These samples were excluded from the positive and negative by comparator percent agreement calculations. Additionally, there were 6 indeterminate results from the COBAS assay and 15 from the prototype assay where either the sample did not have enough material based on β-actin Ct outside the linear range of the assay or MAGE-A3 expression for the sample was above the threshold, but the MAGE-A3 Ct was outside the linear range. As a result, there were 117 results from the COBAS assay and 108 results from the prototype assay with data that could be used for the cross-validation to compare the two different tests (Table 32). The overall concordance between the COBAS and prototype assays was 98/107 or 91.6% (Table 33). The positive by comparator percent agreement of the COBAS test using the prototype assay as the "gold standard" was 59/64 or 92.2%, while negative by comparator percent agreement was 39/43 or 90.7% (Table 33). In the case of discordant results between the COBAS and prototype assays, results generated by frozen tissue sample analysis were used to resolve discordance (Table 34).

Of the 9 samples with discordant results between the COBAS and prototype assays, 7 demonstrated concordance between the COBAS and frozen assays and 2 demonstrated concordance between the prototype and frozen assays. As a result when using the frozen result to resolve discordance, positive by comparator percent agreement of the COBAS assays increases to 63/64 or 98.4% and negative by comparator percent agreement increases to 42/43 or 97.7% (Table 34).

The Positive and Negative by Comparator Percent Agreement of the COBAS TaqMan MAGE-A3 Test exceeded the specifications of greater than or equal to 85%. The acceptance criteria for Positive and Negative by Comparator Percent Agreement were met.

Method Correlation/Cross Validation Control Validation

Experiment Control MAGE Gene Cts are shown in Table 30; Experiment Control β-actin Gene Cts are shown in Table 31. Control Cts are within validated range. Experiment passed validation.

Method Correlation/Cross Validation Experiment Details are shown in Tables 37, 38 and 39.

Reproducibility

Purpose: Demonstrate reproducibility and robustness of the test across data sets generated by multiple operators on multiple days with multiple reagent lots and multiple instruments.

Sample Material:

12 samples from manually microdissected NSCLC FFPE Clinical Samples were extracted using the QIAGEN RNeasy FFPE Kit with DNase I Digestion step and amplified/detected using the COBAS TaqMan MAGE-A3 Test.

Procedure:

The study consisted of two replicates per sample.

Two reagent lots were tested for QIAGEN sample preparation and TaqMan reagents.

Experiments were performed by two different operators on two different days using two different COBAS TaqMan 48 Analyzers.

Analysis:

MAGE-A3 expression for each clinical specimen was calculated from the average of two RT-PCR replicates. In addition, MAGE-A3 call was assessed for every replicate from each sample. Reproducibility was also based upon comparison of MAGE-A3 gene expression calculated from the Delta Ct value between MAGE-A3 and the β-actin gene. Comparison between MAGE-A3 expression for samples tested with different reagents lots, instruments, operators and on different days was performed using Pearson Correlation.

Acceptance Criteria:

>90% MAGE-A3 call concordance between samples that are at least 3× the Limit of Detection of the test (3% GERL) from run to run and within run replicates.

Pearson Correlation >90% between samples

Reproducibility Results

MAGE-A3 Expression Threshold is the cutoff level of MAGE-A3 expression that determines if a patient will receive a MAGE-A3 specific immunotherapy. Patients with MAGE-A3 expression equal to or above the threshold will have a MAGE-A3 positive call and receive treatment. Patients with MAGE-A3 expression below the threshold will have a MAGE-A3 negative call and not receive treatment. Reproducibility studies of the test were based on the MAGE-A3 expression call for each specimen using the following equations:

$$\text{MAGE-}A3 \text{ Expression Threshold} = 2^{\wedge}(\beta\text{-actin Ct of } 100\% \text{ GERL Control} - \text{MAGE-}A3 \text{ Ct 1\% GERL Control})$$

$$\text{MAGE-}A3 \text{ Expression for clinical specimen} = 2^{\wedge}(\beta\text{-actin Ct of specimen} - \text{MAGE-}A3 \text{ Ct of specimen})$$

In addition, assay reproducibility was assessed by comparing the correlation of MAGE-A3 expression between the two runs by Pearson Product-Moment Correlation Coefficient (r). Table 40 and Table 37 show the MAGE-A3 expression threshold generated from the GERL RNA controls tested with Run 1 and 2 based on delta Ct between β-actin and MAGE-A3. Table 41 and Table 43 show the MAGE-A3 call for each of the 12 specimens tested in Runs 1 and 2.

Table 42 shows Run 2—MAGE-A3 Expression Threshold from GERL RNA Controls; Table 43 shows Run 2—MAGE-A3 Expression Call for Reproducibility Specimens For all samples tested, there was 100% correlation for MAGE-A3 expression call between the two runs. In addition, assay reproducibility was assessed by comparing the correlation of MAGE-A3 expression between the two runs by Pearson Product-Moment Correlation Coefficient (r). Pearson Correlation Coefficient was 0.987 when comparing MAGE-A3 Expression between the two different runs. Acceptance Criteria for reproducibility were met.

Table 44 shows Reproducibility Validation; Control Cts are within validated range. Experiment passed validation.

Reproducibility Experiment Details are shown in Tables 45, 46 and 47

The invention claimed is:

1. A probe consisting of an isolated nucleotide molecule having a sequence selected from: (a) SEQ ID NO:17 having a fluorescent reporter dye at the 5' end and a non-fluorescent quencher at the 3' end, and (b) a sequence of 5'-ELFLLLF-FLQGLGALFLLFAGFAAGFLLFP (SEQ ID NO:53), where E=FAM reporter, F=5-methyl dC, Q=BHQ2 quencher, L=5-Propynyl dU, P=phosphate, and I=HEX Reporter.

2. A kit comprising (i) a primer consisting of SEQ ID NO:11, (ii) a primer consisting of SEQ ID NO:12; and (iii) a probe consisting of SEQ ID NO:17 having 6-carboxyfluorescein at the 5' end and a non-fluorescent quencher at the 3' end.

3. A kit comprising (i) a primer consisting of a nucleotide molecule consisting of SEQ ID NO:11, (ii) a primer consisting of a nucleotide molecule consisting of SEQ ID NO:12; and (iii) a probe consisting of a molecule having a sequence of 5'-ELFLLLFFLQGLGALFLLFAGFAAGFLLFP (SEQ ID NO:53), where E=FAM reporter, F=5-methyl dC, Q=BHQ2 quencher, L=5-Propynyl dU, P=phosphate, and I=HEX Reporter.

4. A method for determining the presence of MAGE-A3 in Formalin-Fixed Paraffin-Embedded (FFPE) tumour tissue, comprising:
  (a) obtaining isolated nucleotide sequences from a FFPE tumour tissue sample;
  (b) contacting said isolated nucleotide sequences, under conditions suitable for amplification, with a set of two primers, one consisting of SEQ ID NO:11, and one consisting of SEQ ID NO:12; and
  (c) detecting any amplification product resulting from step (b), using a probe according to claim 1.

5. A method of diagnosing a human patient as having a MAGE-A3 expressing tumor, comprising
  (a) obtaining isolated nucleotide sequences from a FFPE tumour tissue sample from said patient;

(b) contacting said isolated nucleotide sequences, under conditions suitable for amplification, with a primer consisting of SEQ ID NO:11 and a primer consisting of SEQ ID NO:12; and
(c) detecting any amplification product resulting from step (b), using a probe according to claim 1, wherein said primers amplify a MAGE-A3 polynucleotide fragment to which the probe binds, and where detection of MAGE-A3 expression in the sample diagnoses the patient as having a MAGE-A3 expressing tumor.

* * * * *

SEQUENCE LISTING

<160> NUMBER OF SEQ ID NOS: 57

<210> SEQ ID NO 1
<211> LENGTH: 19
<212> TYPE: DNA
<213> ORGANISM: Homo sapiens

<400> SEQUENCE: 1
tggaggacca gaggccccc                                                    19

<210> SEQ ID NO 2
<211> LENGTH: 22
<212> TYPE: DNA
<213> ORGANISM: Artificial Sequence
<220> FEATURE:
<223> OTHER INFORMATION: MAGE-A3 reverse primer

<400> SEQUENCE: 2
ggacgattat caggaggcct gc                                                22

<210> SEQ ID NO 3
<211> LENGTH: 21
<212> TYPE: DNA
<213> ORGANISM: homo sapiens

<400> SEQUENCE: 3
gtcgtcggaa attggcagta t                                                 21

<210> SEQ ID NO 4

```
<211> LENGTH: 19
<212> TYPE: DNA
<213> ORGANISM: Artificial Sequence
<220> FEATURE:
<223> OTHER INFORMATION: MAGE-A3 reverse primer

<400> SEQUENCE: 4
tggggtccac ttccatcag                                                    19

<210> SEQ ID NO 5
<211> LENGTH: 23
<212> TYPE: DNA
<213> ORGANISM: homo sapiens

<400> SEQUENCE: 5
taagcctttg ttagagcctc caa                                               23

<210> SEQ ID NO 6
<211> LENGTH: 21
<212> TYPE: DNA
<213> ORGANISM: Artificial Sequence
<220> FEATURE:
<223> OTHER INFORMATION: MAGE-A3 reverse primer

<400> SEQUENCE: 6
ggagagaggg agcatgtgag a                                                 21

<210> SEQ ID NO 7
<211> LENGTH: 22
<212> TYPE: DNA
<213> ORGANISM: Homo sapiens

<400> SEQUENCE: 7
tgctgggtga caatcagatc at                                                22

<210> SEQ ID NO 8
<211> LENGTH: 20
<212> TYPE: DNA
<213> ORGANISM: Artificial Sequence
<220> FEATURE:
<223> OTHER INFORMATION: MAGE-A3 reverse primer

<400> SEQUENCE: 8
cgccctctct tgcgattatg                                                   20

<210> SEQ ID NO 9
<211> LENGTH: 19
<212> TYPE: DNA
<213> ORGANISM: Homo sapiens

<400> SEQUENCE: 9
ccaacatttc gtgcaggaa                                                    19

<210> SEQ ID NO 10
<211> LENGTH: 18
<212> TYPE: DNA
<213> ORGANISM: Artificial Sequence
<220> FEATURE:
<223> OTHER INFORMATION: MAGE-A3 reverse primer

<400> SEQUENCE: 10
ccttggaccc cacaggaa                                                     18

<210> SEQ ID NO 11
<211> LENGTH: 22
```

```
<212> TYPE: DNA
<213> ORGANISM: Homo sapiens

<400> SEQUENCE: 11
tgtcgtcgga aattggcagt at                                            22

<210> SEQ ID NO 12
<211> LENGTH: 22
<212> TYPE: DNA
<213> ORGANISM: Artificial Sequence
<220> FEATURE:
<223> OTHER INFORMATION: MAGE-A3 reverse primer

<400> SEQUENCE: 12
caaagaccag ctgcaaggaa ct                                            22

<210> SEQ ID NO 13
<211> LENGTH: 17
<212> TYPE: DNA
<213> ORGANISM: Homo sapiens

<400> SEQUENCE: 13
aaagcttcca gttcctt                                                  17

<210> SEQ ID NO 14
<211> LENGTH: 17
<212> TYPE: DNA
<213> ORGANISM: Homo sapiens

<400> SEQUENCE: 14
ttccattcag tactcag                                                  17

<210> SEQ ID NO 15
<211> LENGTH: 15
<212> TYPE: DNA
<213> ORGANISM: Homo sapiens

<400> SEQUENCE: 15
caggaggcct gcctt                                                    15

<210> SEQ ID NO 16
<211> LENGTH: 20
<212> TYPE: DNA
<213> ORGANISM: Homo sapiens

<400> SEQUENCE: 16
ttcataacat gcaggatcac                                               20

<210> SEQ ID NO 17
<211> LENGTH: 18
<212> TYPE: DNA
<213> ORGANISM: Homo sapiens

<400> SEQUENCE: 17
cctgtgatct tcagcaaa                                                 18

<210> SEQ ID NO 18
<211> LENGTH: 19
<212> TYPE: DNA
<213> ORGANISM: Homo sapiens

<400> SEQUENCE: 18
ggcatcgtga tggactccg                                                19
```

<210> SEQ ID NO 19
<211> LENGTH: 19
<212> TYPE: DNA
<213> ORGANISM: Artificial Sequence
<220> FEATURE:
<223> OTHER INFORMATION: beta actin reverse primer

<400> SEQUENCE: 19
gctggaaggt ggacagcga                                               19

<210> SEQ ID NO 20
<211> LENGTH: 20
<212> TYPE: DNA
<213> ORGANISM: Homo sapiens

<400> SEQUENCE: 20
ctggaacggt gaaggtgaca                                              20

<210> SEQ ID NO 21
<211> LENGTH: 20
<212> TYPE: DNA
<213> ORGANISM: Artificial Sequence
<220> FEATURE:
<223> OTHER INFORMATION: beta actin reverse primer

<400> SEQUENCE: 21
cggccacatt gtgaactttg                                              20

<210> SEQ ID NO 22
<211> LENGTH: 14
<212> TYPE: DNA
<213> ORGANISM: Homo sapiens

<400> SEQUENCE: 22
tgctcgctcc aacc                                                    14

<210> SEQ ID NO 23
<211> LENGTH: 9
<212> TYPE: PRT
<213> ORGANISM: Homo sapiens

<400> SEQUENCE: 23

Phe Leu Trp Gly Pro Arg Ala Leu Val
1               5

<210> SEQ ID NO 24
<211> LENGTH: 10
<212> TYPE: PRT
<213> ORGANISM: Homo sapiens

<400> SEQUENCE: 24

Met Glu Val Asp Pro Ile Gly His Leu Tyr
1               5                   10

<210> SEQ ID NO 25
<211> LENGTH: 10
<212> TYPE: PRT
<213> ORGANISM: Homo sapiens

<400> SEQUENCE: 25

Val His Phe Leu Leu Leu Lys Tyr Arg Ala
1               5                   10

<210> SEQ ID NO 26

```
<211> LENGTH: 10
<212> TYPE: PRT
<213> ORGANISM: Homo sapiens

<400> SEQUENCE: 26

Leu Val His Phe Leu Leu Leu Lys Tyr Arg
1               5                   10

<210> SEQ ID NO 27
<211> LENGTH: 10
<212> TYPE: PRT
<213> ORGANISM: Homo sapiens

<400> SEQUENCE: 27

Leu Lys Tyr Arg Ala Arg Glu Pro Val Thr
1               5                   10

<210> SEQ ID NO 28
<211> LENGTH: 16
<212> TYPE: PRT
<213> ORGANISM: Homo sapiens

<400> SEQUENCE: 28

Ala Cys Tyr Glu Phe Leu Trp Gly Pro Arg Ala Leu Val Glu Thr Ser
1               5                   10                  15

<210> SEQ ID NO 29
<211> LENGTH: 12
<212> TYPE: PRT
<213> ORGANISM: Homo sapiens

<400> SEQUENCE: 29

Thr Gln His Phe Val Gln Glu Asn Tyr Leu Glu Tyr
1               5                   10

<210> SEQ ID NO 30
<211> LENGTH: 20
<212> TYPE: DNA
<213> ORGANISM: Artificial Sequence
<220> FEATURE:
<223> OTHER INFORMATION: CpG 1826

<400> SEQUENCE: 30
tccatgacgt tcctgacgtt                                          20

<210> SEQ ID NO 31
<211> LENGTH: 18
<212> TYPE: DNA
<213> ORGANISM: Artificial Sequence
<220> FEATURE:
<223> OTHER INFORMATION: CpG 1758

<400> SEQUENCE: 31
tctcccagcg tgcgccat                                            18

<210> SEQ ID NO 32
<211> LENGTH: 30
<212> TYPE: DNA
<213> ORGANISM: Artificial Sequence
<220> FEATURE:
<223> OTHER INFORMATION: CpG oligonucleotide

<400> SEQUENCE: 32
accgatgacg tcgccggtga cggcaccacg                               30
```

<210> SEQ ID NO 33
<211> LENGTH: 24
<212> TYPE: DNA
<213> ORGANISM: Artificial Sequence
<220> FEATURE:
<223> OTHER INFORMATION: CpG 2006, CpG 7909

<400> SEQUENCE: 33
tcgtcgtttt gtcgttttgt cgtt                                          24

<210> SEQ ID NO 34
<211> LENGTH: 20
<212> TYPE: DNA
<213> ORGANISM: Artificial Sequence
<220> FEATURE:
<223> OTHER INFORMATION: CpG 1668

<400> SEQUENCE: 34
tccatgacgt tcctgatgct                                               20

<210> SEQ ID NO 35
<211> LENGTH: 1353
<212> TYPE: DNA
<213> ORGANISM: Artificial Sequence
<220> FEATURE:
<223> OTHER INFORMATION: Nucleotide sequence encoding fusion protein of
      Protein D fragment, Mage 3 fragment, and histidine tail

<400> SEQUENCE: 35
atggatccaa aaactttagc cctttcttta ttagcagctg gcgtactagc aggttgtagc      60
agccattcat caaatatggc gaatacccaa atgaaatcag acaaaatcat tattgctcac     120
cgtggtgcta gcggttattt accagagcat acgttagaat ctaaagcact tgcgtttgca     180
caacaggctg attatttaga gcaagattta gcaatgacta aggatggtcg tttagtggtt     240
attcacgatc acttttttaga tggcttgact gatgttgcga aaaaattccc acatcgtcat     300
cgtaaagatg gccgttacta tgtcatcgac tttaccttaa aagaaattca agtttagaa      360 atgacagaaa actttgaaac catggatctg aacagcgta gtcagcactg caagcctgaa     420
gaaggccttg aggcccgagg agaggccctg ggcctggtgg gtgcgcaggc tcctgctact     480
gaggagcagg aggctgcctc ctcctcttct actctagttg aagtcaccct gggggaggtg     540
cctgctgccg agtcaccaga tcctccccag agtcctcagg gagcctccag cctccccact     600
accatgaact ccctctctg gagccaatcc tatgaggact ccagcaacca agaagaggag     660
gggccaagca ccttccctga cctggagtcc gagttccaag cagcactcag taggaaggtg     720
gccgaattgg ttcatttct gctcctcaag tatcgagcca gggagccggt cacaaaggca     780
gaaatgctgg ggagtgtcgt cggaaattgg cagtatttct ttcctgtgat cttcagcaaa     840
gcttccagtt ccttgcagct ggtctttggc atcgagctga tggaagtgga ccccatcggc     900
cacttgtaca tctttgccac ctgcctgggc ctctcctacg atggcctgct gggtgacaat     960
cagatcatgc ccaaggcagg cctcctgata atcgtcctgg ccataatcgc aagagagggc    1020
gactgtgccc ctgaggagaa aatctgggag gagctgagtg tgttagaggt gtttgagggg    1080
agggaagaca gtatcttggg ggatcccaag aagctgctca cccaacattt cgtgcaggaa    1140
aactacctgg agtaccggca ggtccccggc agtgatcctg catgttatga attcctgtgg    1200
ggtccaaggg ccctcgttga aaccagctat gtgaaagtcc tgcaccatat ggtaaagatc    1260
agtggaggac ctcacatttc ctacccaccc ctgcatgagt gggttttgag agaggggaa    1320 gagggcggtc atcaccatca ccatcaccat taa                                1353

<210> SEQ ID NO 36
<211> LENGTH: 450
<212> TYPE: PRT
<213> ORGANISM: Artificial Sequence
<220> FEATURE:
<223> OTHER INFORMATION: Amino acid sequence of fusion protein of
      Protein D fragment, Mage3 fragment, and histidine tail

<400> SEQUENCE: 36

```
Met Asp Pro Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Met
        115                 120                 125

Asp Leu Glu Gln Arg Ser Gln His Cys Lys Pro Glu Glu Gly Leu Glu
    130                 135                 140

Ala Arg Gly Glu Ala Leu Gly Leu Val Gly Ala Gln Ala Pro Ala Thr
145                 150                 155                 160

Glu Glu Gln Glu Ala Ala Ser Ser Ser Thr Leu Val Glu Val Thr
                165                 170                 175

Leu Gly Glu Val Pro Ala Ala Glu Ser Pro Asp Pro Pro Gln Ser Pro
            180                 185                 190

Gln Gly Ala Ser Ser Leu Pro Thr Thr Met Asn Tyr Pro Leu Trp Ser
        195                 200                 205

Gln Ser Tyr Glu Asp Ser Ser Asn Gln Glu Glu Glu Gly Pro Ser Thr
    210                 215                 220

Phe Pro Asp Leu Glu Ser Glu Phe Gln Ala Ala Leu Ser Arg Lys Val
225                 230                 235                 240

Ala Glu Leu Val His Phe Leu Leu Leu Lys Tyr Arg Ala Arg Glu Pro
                245                 250                 255

Val Thr Lys Ala Glu Met Leu Gly Ser Val Val Gly Asn Trp Gln Tyr
            260                 265                 270

Phe Phe Pro Val Ile Phe Ser Lys Ala Ser Ser Ser Leu Gln Leu Val
        275                 280                 285

Phe Gly Ile Glu Leu Met Glu Val Asp Pro Ile Gly His Leu Tyr Ile
    290                 295                 300

Phe Ala Thr Cys Leu Gly Leu Ser Tyr Asp Gly Leu Leu Gly Asp Asn
305                 310                 315                 320

Gln Ile Met Pro Lys Ala Gly Leu Leu Ile Ile Val Leu Ala Ile Ile
                325                 330                 335

Ala Arg Glu Gly Asp Cys Ala Pro Glu Glu Lys Ile Trp Glu Glu Leu
            340                 345                 350

Ser Val Leu Glu Val Phe Glu Gly Arg Glu Asp Ser Ile Leu Gly Asp
```

```
                355                 360                 365
Pro Lys Lys Leu Leu Thr Gln His Phe Val Gln Glu Asn Tyr Leu Glu
            370                 375                 380

Tyr Arg Gln Val Pro Gly Ser Asp Pro Ala Cys Tyr Glu Phe Leu Trp
385                 390                 395                 400

Gly Pro Arg Ala Leu Val Glu Thr Ser Tyr Val Lys Val Leu His His
                    405                 410                 415

Met Val Lys Ile Ser Gly Gly Pro His Ile Ser Tyr Pro Pro Leu His
                420                 425                 430

Glu Trp Val Leu Arg Glu Gly Glu Glu Gly His His His His His His
            435                 440                 445

His His
    450

<210> SEQ ID NO 37
<211> LENGTH: 403
<212> TYPE: PRT
<213> ORGANISM: Artificial Sequence
<220> FEATURE:
<223> OTHER INFORMATION: Amino acid sequence of fusion protein of
      NS1-Mage3 and histidine tail

<400> SEQUENCE: 37

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Asp Leu Glu Gln Arg Ser Gln His Cys Lys Pro Glu Glu Gly Leu
                85                  90                  95

Glu Ala Arg Gly Glu Ala Leu Gly Leu Val Gly Ala Gln Ala Pro Ala
            100                 105                 110

Thr Glu Glu Gln Glu Ala Ala Ser Ser Ser Thr Leu Val Glu Val
        115                 120                 125

Thr Leu Gly Glu Val Pro Ala Ala Glu Ser Pro Asp Pro Pro Gln Ser
    130                 135                 140

Pro Gln Gly Ala Ser Ser Leu Pro Thr Thr Met Asn Tyr Pro Leu Trp
145                 150                 155                 160

Ser Gln Ser Tyr Glu Asp Ser Ser Asn Gln Glu Glu Glu Gly Pro Ser
                165                 170                 175

Thr Phe Pro Asp Leu Glu Ser Glu Phe Gln Ala Ala Leu Ser Arg Lys
            180                 185                 190

Val Ala Glu Leu Val His Phe Leu Leu Leu Lys Tyr Arg Ala Arg Glu
        195                 200                 205

Pro Val Thr Lys Ala Glu Met Leu Gly Ser Val Val Gly Asn Trp Gln
    210                 215                 220

Tyr Phe Phe Pro Val Ile Phe Ser Lys Ala Ser Ser Ser Leu Gln Leu
225                 230                 235                 240

Val Phe Gly Ile Glu Leu Met Glu Val Asp Pro Ile Gly His Leu Tyr
                245                 250                 255
```

```
Ile Phe Ala Thr Cys Leu Gly Leu Ser Tyr Asp Gly Leu Gly Asp
            260                 265                 270
Asn Gln Ile Met Pro Lys Ala Gly Leu Leu Ile Ile Val Leu Ala Ile
        275                 280                 285
Ile Ala Arg Glu Gly Asp Cys Ala Pro Glu Glu Lys Ile Trp Glu Glu
    290                 295                 300
Leu Ser Val Leu Glu Val Phe Glu Gly Arg Glu Asp Ser Ile Leu Gly
305                 310                 315                 320
Asp Pro Lys Lys Leu Thr Gln His Phe Val Gln Glu Asn Tyr Leu
                325                 330                 335
Glu Tyr Arg Gln Val Pro Gly Ser Asp Pro Ala Cys Tyr Glu Phe Leu
            340                 345                 350
Trp Gly Pro Arg Ala Leu Val Glu Thr Ser Tyr Val Lys Val Leu His
        355                 360                 365
His Met Val Lys Ile Ser Gly Gly Pro His Ile Ser Tyr Pro Pro Leu
    370                 375                 380
His Glu Trp Val Leu Arg Glu Gly Glu Glu Gly Gly His His His
385                 390                 395                 400
His His His

<210> SEQ ID NO 38
<211> LENGTH: 1212
<212> TYPE: DNA
<213> ORGANISM: Artificial Sequence
<220> FEATURE:
<223> OTHER INFORMATION: nucleotide sequence encoding fusion protein of
      NS1-Mage3 and histidine tail

<400> SEQUENCE: 38
atggatccaa acactgtgtc aagctttcag gtagattgct ttctttggca tgtccgcaaa        60
cgagttgcag accaagaact aggtgatgcc ccattccttg atcggcttcg ccgagatcag       120
aaatccctaa gaggaagggg cagcactctt ggtctggaca tcgagacagc cacacgtgct       180
ggaaagcaga tagtggagcg gattctgaaa gaagaatccg atgaggcact aaaaatgacc       240
atggatctgg aacagcgtag tcagcactgc aagcctgaag aaggccttga ggcccgagga       300
gaggccctgg gcctggtggg tgcgcaggct cctgctactg aggagcagga ggctgcctcc       360
tcctcttcta ctctagttga agtcaccctg ggggaggtgc ctgctgccga gtcaccagat       420
cctcccagaa gtcctcaggg agcctccagc ctccccacta ccatgaacta ccctctctgg       480
agccaatcct atgaggactc cagcaaccaa gaagaggagg ggccaagcac cttccctgac       540
ctggagtccg agttccaagc agcactcagt aggaaggtgg ccgaattggt tcattttctg       600
ctcctcaagt atcgagccag ggagccggtc acaaaggcag aaatgctggg gagtgtcgtc       660
ggaaattggc agtatttctt cctgtgatc ttcagcaaag cttccagttc cttgcagctg       720
gtctttggca tcgagctgat ggaagtggac cccatcggcc acttgtacat ctttgccacc       780
tgcctgggcc tctcctacga tggcctgctg ggtgacaatc agatcatgcc caaggcaggc       840
ctcctgataa tcgtcctggc cataatcgca agagagggcg actgtgcccc tgaggagaaa       900
atctgggagg agctgagtgt gttagaggtg tttgagggga gggaagacag tatcttgggg       960
gatcccaaga agctgctcac ccaacatttc gtgcaggaaa actacctgga gtaccggcag      1020
gtccccggca gtgatcctgc atgttatgaa ttcctgtggg gtccaagggc cctcgttgaa      1080
accagctatg tgaaagtcct gcaccatatg gtaaagatca gtggaggacc tcacatttcc      1140
tacccacccc tgcatgagtg ggttttgaga gagggggaag agggcggtca tcaccatcac      1200
```
catcaccatt aa                                                           1212

<210> SEQ ID NO 39
<211> LENGTH: 453
<212> TYPE: PRT
<213> ORGANISM: Artificial Sequence
<220> FEATURE:
<223> OTHER INFORMATION: amino acid sequence of fusion protein of
      CLytA-Mage3 and histidine tail

<400> SEQUENCE: 39

```
Met Lys Gly Gly Ile Val His Ser Asp Gly Ser Tyr Pro Lys Asp Lys
1               5                   10                  15

Phe Glu Lys Ile Asn Gly Thr Trp Tyr Tyr Phe Asp Ser Ser Gly Tyr
                20                  25                  30

Met Leu Ala Asp Arg Trp Arg Lys His Thr Asp Gly Asn Trp Tyr Trp
            35                  40                  45

Phe Asp Asn Ser Gly Glu Met Ala Thr Gly Trp Lys Lys Ile Ala Asp
        50                  55                  60

Lys Trp Tyr Tyr Phe Asn Glu Glu Gly Ala Met Lys Thr Gly Trp Val
65                  70                  75                  80

Lys Tyr Lys Asp Thr Trp Tyr Tyr Leu Asp Ala Lys Glu Gly Ala Met
                85                  90                  95

Val Ser Asn Ala Phe Ile Gln Ser Ala Asp Gly Thr Gly Trp Tyr Tyr
                100                 105                 110

Leu Lys Pro Asp Gly Thr Leu Ala Asp Arg Pro Glu Leu Ala Ser Met
            115                 120                 125

Leu Asp Met Asp Leu Glu Gln Arg Ser Gln His Cys Lys Pro Glu Glu
        130                 135                 140

Gly Leu Glu Ala Arg Gly Glu Ala Leu Gly Leu Val Gly Ala Gln Ala
145                 150                 155                 160

Pro Ala Thr Glu Glu Gln Glu Ala Ala Ser Ser Ser Thr Leu Val
                165                 170                 175

Glu Val Thr Leu Gly Glu Val Pro Ala Ala Glu Ser Pro Asp Pro Pro
            180                 185                 190

Gln Ser Pro Gln Gly Ala Ser Ser Leu Pro Thr Thr Met Asn Tyr Pro
        195                 200                 205

Leu Trp Ser Gln Ser Tyr Glu Asp Ser Ser Asn Gln Glu Glu Glu Gly
    210                 215                 220

Pro Ser Thr Phe Pro Asp Leu Glu Ser Glu Phe Gln Ala Ala Leu Ser
225                 230                 235                 240

Arg Lys Val Ala Lys Leu Val His Phe Leu Leu Lys Tyr Arg Ala
                245                 250                 255

Arg Glu Pro Val Thr Lys Ala Glu Met Leu Gly Ser Val Val Gly Asn
            260                 265                 270

Trp Gln Tyr Phe Phe Pro Val Ile Phe Ser Lys Ala Ser Asp Ser Leu
        275                 280                 285

Gln Leu Val Phe Gly Ile Glu Leu Met Glu Val Asp Pro Ile Gly His
    290                 295                 300

Val Tyr Ile Phe Ala Thr Cys Leu Gly Leu Ser Tyr Asp Gly Leu Leu
305                 310                 315                 320

Gly Asp Asn Gln Ile Met Pro Lys Thr Gly Phe Leu Ile Ile Ile Leu
                325                 330                 335

Ala Ile Ile Ala Lys Glu Gly Asp Cys Ala Pro Glu Glu Lys Ile Trp
            340                 345                 350
```

Glu Glu Leu Ser Val Leu Glu Val Phe Glu Gly Arg Glu Asp Ser Ile
            355                 360                 365

Phe Gly Asp Pro Lys Lys Leu Thr Gln Tyr Phe Val Gln Glu Asn
    370                 375                 380

Tyr Leu Glu Tyr Arg Gln Val Pro Gly Ser Asp Pro Ala Cys Tyr Glu
385                 390                 395                 400

Phe Leu Trp Gly Pro Arg Ala Leu Ile Glu Thr Ser Tyr Val Lys Val
                405                 410                 415

Leu His His Met Val Lys Ile Ser Gly Gly Pro Arg Ile Ser Tyr Pro
                420                 425                 430

Leu Leu His Glu Trp Ala Leu Arg Glu Gly Glu Gly Gly His His
            435                 440                 445

His His His His His
    450

<210> SEQ ID NO 40
<211> LENGTH: 1362
<212> TYPE: DNA
<213> ORGANISM: Artificial Sequence
<220> FEATURE:
<223> OTHER INFORMATION: nucleotide sequence encoding fusion protein of
      CLytA-Mage3 and histidine tail

<400> SEQUENCE: 40

```
atgaaagggg gaattgtaca ttcagacggc tcttatccaa agacaagtt tgagaaaatc      60 aatggcactt gtactactt tgacagttca ggctatatgc ttgcagaccg ctggaggaag     120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca aaccagacgg aacactggca    360
gacaggccag aattggccag catgctggac atggatctgg aacagcgtag tcagcactgc    420
aagcctgaag aaggccttga ggcccgagga gaggccctgg gcctggtggg tgcgcaggct    480
cctgctactg aggagcagga ggctgcctcc tcctcttcta ctctagttga agtcaccctg    540
ggggaggtgc ctgctgccga gtcaccagat cctccccaga gtcctcaggg agcctccagc    600
ctccccacta ccatgaacta ccctctctgg agccaatcct atgaggactc cagcaaccaa    660
gaagaggagg ggccaagcac cttccctgac ctggagtctg agttccaagc agcactcagt    720
aggaaggtgg ccaagttggt tcatttcctg ctcctcaagt atcgagccag ggagccggtc    780
acaaaggcag aaatgctggg gagtgtcgtc ggaaattggc agtacttctt cctgtgatc    840 ttcagcaaag cttccgattc cttgcagctg gtctttggca tcgagctgat ggaagtggac    900
cccatcggcc acgtgtacat ctttgccacc tgcctgggcc tctcctacga tggcctgctg    960
ggtgacaatc agatcatgcc caagacaggc ttcctgataa tcatcctggc cataatcgca   1020
aaagagggcg actgtgcccc tgaggagaaa atctgggagg agctgagtgt gttagaggtg   1080
tttgagggga gggaagacag tatcttcggg gatcccaaga gctgctcac ccaatatttc   1140 gtgcaggaaa actacctgga gtaccggcag gtccccggca gtgatcctgc atgctatgag   1200
ttcctgtggg gtccaagggc cctcattgaa accagctatg tgaaagtcct gcaccatatg   1260
gtaaagatca gtggaggacc tcgcatttcc tacccactcc tgcatgagtg ggctttgaga   1320
gagggggaag agggcggtca tcaccatcac catcaccatt aa                      1362
```

<210> SEQ ID NO 41
<211> LENGTH: 100
<212> TYPE: DNA
<213> ORGANISM: Homo sapiens

<400> SEQUENCE: 41
gtcatcaaaa attacaagcg ctgctttcct gtgatcttcg gcaaagcctc cgagtccctg    60
aagatgatct ttggcattga cgtgaaggaa gtggacccca                         100

<210> SEQ ID NO 42
<211> LENGTH: 100
<212> TYPE: DNA
<213> ORGANISM: Homo sapiens

<400> SEQUENCE: 42
gtcataaaaa attatgaaga ccacttccct ttgttgttta gtgaagcctc cgagtgcatg    60
ctgctggtct ttggcattga tgtaaaggaa gtggatccca                         100

<210> SEQ ID NO 43
<211> LENGTH: 100
<212> TYPE: DNA
<213> ORGANISM: Homo sapiens

<400> SEQUENCE: 43
gtcatcaaaa attatgagga ctactttcct gagatattta gggaagcctc tgtatgcatg    60
caactgctct ttggcattga tgtgaaggaa gtggacccca                         100

<210> SEQ ID NO 44
<211> LENGTH: 101
<212> TYPE: DNA
<213> ORGANISM: Homo sapiens

<400> SEQUENCE: 44
gtcatcagaa attttccagg acttctttcc tgtgatcttc agcaaagcct ccgagtactt    60
gcagctggtc tttggcatcg aggtggtgga agtggtccgc a                       101

<210> SEQ ID NO 45
<211> LENGTH: 100
<212> TYPE: DNA
<213> ORGANISM: Homo sapiens

<400> SEQUENCE: 45
gtcctcagaa attgccagga cttctttccc gtgatcttca gcaaagcctc cgagtacttg    60
cagctggtct ttggcatcga ggtggtggaa gtggtcccca                         100

<210> SEQ ID NO 46
<211> LENGTH: 100
<212> TYPE: DNA
<213> ORGANISM: Homo sapiens

<400> SEQUENCE: 46
gtcatcaaaa attacaagcg ctgctttcct gtgatcttcg gcaaagcctc cgagtccctg    60
aagatgatct ttggcattga cgtgaaggaa gtggaccccg                         100

<210> SEQ ID NO 47
<211> LENGTH: 101
<212> TYPE: DNA
<213> ORGANISM: Homo sapiens

<400> SEQUENCE: 47

```
gtcatcaaaa attacaagca ctagtttcct tgtgatctat ggcaaagcct cagagtgcat    60
gcaggtgatg tttggcattg acatgaagga agtggacccc g                       101

<210> SEQ ID NO 48
<211> LENGTH: 100
<212> TYPE: DNA
<213> ORGANISM: Homo sapiens

<400> SEQUENCE: 48
gtcatcaaaa attacaagaa ccactttcct gatatcttca gcaaagcctc tgagtgcatg    60
caggtgatct ttggcattga tgtgaaggaa gtggaccctg                         100

<210> SEQ ID NO 49
<211> LENGTH: 100
<212> TYPE: DNA
<213> ORGANISM: Homo sapiens

<400> SEQUENCE: 49
gtcgtcggaa attggcagta cttctttcct gtgatcttca gcaaagcttc cgattccttg    60
cagctggtct ttggcatcga gctgatggaa gtggacccca                         100

<210> SEQ ID NO 50
<211> LENGTH: 100
<212> TYPE: DNA
<213> ORGANISM: Homo sapiens

<400> SEQUENCE: 50
gtcgtcggaa attggcagta tttctttcct gtgatcttca gcaaagcttc cagttccttg    60
cagctggtct ttggcatcga gctgatggaa gtggacccca                         100

<210> SEQ ID NO 51
<211> LENGTH: 599
<212> TYPE: DNA
<213> ORGANISM: Homo sapiens

<400> SEQUENCE: 51
ccaagcagca ctcagtagga aggtggccga gttggttcat tttctgctcc tcaagtatcg    60
agccagggag ccggtcacaa aggcagaaat gctggggagt gtcgtcggaa attggcagta   120
tttctttcct gtgatcttca gcaaagcttc cagttcctgc agctggtctt tggcatcgag   180
ctgatggaag tggaccccat cggccacttg tacatctttg ccacctgcct gggcctctcc   240
tacgatggcc tgctgggtga caatcagatc atgcccaagg caggcctcct gataatcgtc   300
ctggccataa tcgcaagaga gggcgactgt gcccctgagg agaaaatctg ggaggagctg   360
agtgtgttag aggtgtttga ggggagggaa gacagtatct tgggggatcc aagaagctg   420 ctcacccaac atttcgtgca ggaaaactac ctggagtacc ggcaggtccc cggcagtgat   480
cctgcatgtt atgaattcct gtggggtcca agggccctcg ttgaaaccag ctatgtgaaa   540
gtcctgcacc atatggtaaa gatcagtgga ggacctcaca tttcctaccc acccctgca   599

<210> SEQ ID NO 52
<211> LENGTH: 600
<212> TYPE: DNA
<213> ORGANISM: Homo sapiens

<400> SEQUENCE: 52
ccaagcagca ctcagtagga aggtggccaa gttggttcat tttctgctcc tcaagtatcg    60
```

| | | |
|---|---|---|
| agccagggag ccggtcacaa aggcagaaat gctggggagt gtcgtcggaa attggcagta | 120 | |
| cttctttcct gtgatcttca gcaaagcttc cgattccttg cagctggtct ttggcatcga | 180 | |
| gctgatggaa gtggacccca tcggccacgt gtacatcttt gccacctgcc tgggcctctc | 240 | |
| ctacgatggc ctgctgggtg acaatcagat catgcccaag acaggcttcc tgataatcat | 300 | |
| cctggccata atcgcaaaag agggcgactg tgcccctgag gagaaaatct gggaggagct | 360 | |
| gagtgtgtta gaggtgtttg aggggaggga agacagtatc ttcggggatc ccaagaagct | 420 | |
| gctcacccaa tatttcgtgc aggaaaacta cctggagtac cggcaggtcc ccggcagtga | 480 | |
| tcctgcatgc tatgagttcc tgtggggtcc aagggccctc attgaaacca gctatgtgaa | 540 | |
| agtcctgcac catatggtaa agatcagtgg aggacctcgc atttcctacc cactcctgca | 600 | |

```
<210> SEQ ID NO 53
<211> LENGTH: 28
<212> TYPE: DNA
<213> ORGANISM: Artificial Sequence
<220> FEATURE:
<223> OTHER INFORMATION: Modified MAGE-A3 probe with 5' FAM Reporter
      dye, internal quencher and 3' phosphate
<220> FEATURE:
<221> NAME/KEY: misc_feature
<222> LOCATION: (1)..(1)
<223> OTHER INFORMATION: N = 5-propynyl dU
<220> FEATURE:
<221> NAME/KEY: misc_feature
<222> LOCATION: (2)..(2)
<223> OTHER INFORMATION: N = 5-methyl dC
<220> FEATURE:
<221> NAME/KEY: misc_feature
<222> LOCATION: (3)..(5)
<223> OTHER INFORMATION: N = 5-propynyl dU
<220> FEATURE:
<221> NAME/KEY: misc_feature
<222> LOCATION: (6)..(7)
<223> OTHER INFORMATION: N = 5-methyl dC
<220> FEATURE:
<221> NAME/KEY: misc_feature
<222> LOCATION: (8)..(8)
<223> OTHER INFORMATION: N = 5-propynyl dU
<220> FEATURE:
<221> NAME/KEY: misc_feature
<222> LOCATION: (10)..(10)
<223> OTHER INFORMATION: N = 5-propynyl dU
<220> FEATURE:
<221> NAME/KEY: misc_feature
<222> LOCATION: (13)..(13)
<223> OTHER INFORMATION: N = 5-propynyl dU
<220> FEATURE:
<221> NAME/KEY: misc_feature
<222> LOCATION: (14)..(14)
<223> OTHER INFORMATION: N = 5-methyl dC
<220> FEATURE:
<221> NAME/KEY: misc_feature
<222> LOCATION: (15)..(16)
<223> OTHER INFORMATION: N = 5-propynyl dU
<220> FEATURE:
<221> NAME/KEY: misc_feature
<222> LOCATION: (17)..(17)
<223> OTHER INFORMATION: N = 5-methyl dC
<220> FEATURE:
<221> NAME/KEY: misc_feature
<222> LOCATION: (20)..(20)
<223> OTHER INFORMATION: N = 5-methyl dC
<220> FEATURE:
<221> NAME/KEY: misc_feature
<222> LOCATION: (25)..(25)
<223> OTHER INFORMATION: N = 5-methyl dC
<220> FEATURE:
<221> NAME/KEY: misc_feature
<222> LOCATION: (26)..(27)
<223> OTHER INFORMATION: N = 5-propynyl dU
<220> FEATURE:
```

```
<221> NAME/KEY: misc_feature
<222> LOCATION: (28)..(28)
<223> OTHER INFORMATION: N = 5-methyl dC

<400> SEQUENCE: 53
nnnnnnnngn gannnnnagn aaagnnnn                                         28

<210> SEQ ID NO 54
<211> LENGTH: 28
<212> TYPE: DNA
<213> ORGANISM: Artificial Sequence
<220> FEATURE:
<223> OTHER INFORMATION: equivalent unmodified nucleotides to the
      modified nucleotides contained in MAGEA3F-646MOD probe sequence

<400> SEQUENCE: 54
tctttcctgt gatcttcagc aaagcttc                                         28

<210> SEQ ID NO 55
<211> LENGTH: 17
<212> TYPE: DNA
<213> ORGANISM: Homo sapiens

<400> SEQUENCE: 55
gagcgcggct acagctt                                                     17

<210> SEQ ID NO 56
<211> LENGTH: 22
<212> TYPE: DNA
<213> ORGANISM: Artificial Sequence
<220> FEATURE:
<223> OTHER INFORMATION: reverse primer sequence for Homo sapiens
      beta-actin gene

<400> SEQUENCE: 56
tccttaatgt cacgcacgat tt                                               22

<210> SEQ ID NO 57
<211> LENGTH: 18
<212> TYPE: DNA
<213> ORGANISM: Artificial Sequence
<220> FEATURE:
<223> OTHER INFORMATION: probe sequence for Homo sapiens beta-actin
      gene, which the dyes have been removed

<400> SEQUENCE: 57
accaccacgg ccgagcgg                                                    18
```